US012746034B2

(12) United States Patent
Moskowitz et al.

(10) Patent No.: US 12,746,034 B2
(45) Date of Patent: Sep. 29, 2026

(54) TACTILE SENSING AND GUIDANCE SYSTEM

(71) Applicant: IntuiTap Medical, Inc., Houston, TX (US)

(72) Inventors: Nicole C. Moskowitz, Monsey, NY (US); Jessica Traver, Sierra Madre, CA (US); Xavier Garcia-Rojas, The Woodlands, TX (US); Yashar Ganjeh, Chicago, IL (US); Matthew Cruz, Chicago, IL (US); Jonathan Rae Plumb, Halstead (GB); Jack Alexander Lowe, Leeds (GB); Alexander Keith Gomer Pratten Jones, Cambridge (GB); Geoffrey Hutchins, Park Ridge, IL (US); Ann Graff, Chicago, IL (US); Mahesh Vaidyanathan, Houston, TX (US)

(73) Assignee: IntuiTap Medical, Inc., Houston, TX (US)

( * ) Notice: Subject to any disclaimer, the term of this patent is extended or adjusted under 35 U.S.C. 154(b) by 880 days.

(21) Appl. No.: 17/890,970

(22) Filed: Aug. 18, 2022

(65) Prior Publication Data

US 2023/0067892 A1 Mar. 2, 2023

Related U.S. Application Data

(63) Continuation of application No. PCT/US2021/018881, filed on Feb. 19, 2021.

(Continued)

(51) Int. Cl.

*A61B 17/34* (2006.01)
*A61B 17/00* (2006.01)

(Continued)

(52) U.S. Cl.

CPC ...... *A61B 17/3403* (2013.01); *A61B 17/3401* (2013.01); *A61M 5/427* (2013.01);

(Continued)

(58) Field of Classification Search

CPC ............ A61B 17/3401; A61B 17/3403; A61B 2017/00128; A61B 2017/3407;

(Continued)

(56) References Cited

U.S. PATENT DOCUMENTS

| | | | |
|---|---|---|---|
| 4,919,653 | A | 4/1990 | Martinez et al. |
| 5,097,842 | A | 3/1992 | Bonn |

(Continued)

FOREIGN PATENT DOCUMENTS

| | | | |
|---|---|---|---|
| CN | 101877192 | A | 11/2010 |
| CN | 102133096 | A | 7/2011 |

(Continued)

OTHER PUBLICATIONS

EP21757254.4 Extended European Search Report dated Jan. 18, 2024.

(Continued)

*Primary Examiner* — Robert A Lynch

(74) *Attorney, Agent, or Firm* — Wilson Sonsini Goodrich & Rosati

(57) ABSTRACT

Provided are systems and methods for tactile sensing of a target tissue region of a patient in need thereof.

4 Claims, 24 Drawing Sheets

Related U.S. Application Data

(60) Provisional application No. 63/132,960, filed on Dec. 31, 2020, provisional application No. 62/980,085, filed on Feb. 21, 2020.

(51) Int. Cl.
*A61B 90/00* (2016.01)
*A61M 5/42* (2006.01)

(52) U.S. Cl.
CPC ............... *A61B 2017/00128* (2013.01); *A61B 2017/3407* (2013.01); *A61B 2017/3409* (2013.01); *A61B 2090/061* (2016.02); *A61B 2090/064* (2016.02); *A61M 2205/3327* (2013.01); *A61M 2205/3344* (2013.01); *A61M 2205/502* (2013.01)

(58) Field of Classification Search
CPC ...... A61B 2017/3409; A61B 2090/061; A61B 2090/064; A61B 5/6848; A61B 5/6885; A61M 5/427; A61M 2205/3327; A61M 2205/3344; A61M 2205/502
See application file for complete search history.

(56) References Cited

U.S. PATENT DOCUMENTS

| | | | | |
|---|---|---|---|---|
| 5,163,901 | A | 11/1992 | Eldor | |
| 5,706,815 | A | 1/1998 | Sarvazyan et al. | |
| 5,733,262 | A | 3/1998 | Paul | |
| 5,785,663 | A | 7/1998 | Sarvazyan | |
| 5,795,307 | A | 8/1998 | Krueger | |
| 5,833,633 | A | 11/1998 | Sarvazyan | |
| 5,833,634 | A | 11/1998 | Laird et al. | |
| 6,063,031 | A | 5/2000 | Cundari et al. | |
| 6,142,959 | A | 11/2000 | Sarvazyan et al. | |
| 6,251,686 | B1 | 6/2001 | Studer et al. | |
| 6,468,215 | B1 | 10/2002 | Sarvazyan et al. | |
| 6,468,231 | B2 | 10/2002 | Sarvazyan et al. | |
| 6,500,119 | B1 | 12/2002 | West et al. | |
| 6,569,108 | B2 | 5/2003 | Sarvazyan et al. | |
| 6,595,933 | B2 | 7/2003 | Sarvazyan et al. | |
| 6,620,115 | B2 | 9/2003 | Sarvazyan et al. | |
| 7,291,109 | B1 | 11/2007 | Sarvazyan | |
| 7,819,824 | B2 | 10/2010 | Sarvazyan et al. | |
| 7,878,075 | B2 | 2/2011 | Johansson et al. | |
| 7,922,674 | B2 | 4/2011 | Sarvazyan et al. | |
| 7,955,278 | B1 | 6/2011 | Sarvazyan | |
| 8,016,777 | B1 | 9/2011 | Egorov et al. | |
| 8,052,622 | B2 | 11/2011 | Egorov et al. | |
| 8,069,735 | B1 | 12/2011 | Egorov et al. | |
| 8,142,368 | B2 | 3/2012 | Egorov et al. | |
| 8,187,208 | B2 | 5/2012 | Egorov et al. | |
| 8,419,659 | B2 | 4/2013 | Egorov et al. | |
| 8,480,404 | B2 | 7/2013 | Savitsky | |
| 8,814,807 | B2 | 8/2014 | Hulvershorn et al. | |
| 8,840,571 | B2 | 9/2014 | Egorov et al. | |
| 9,179,875 | B2 | 11/2015 | Hua | |
| 10,004,450 | B2 | 6/2018 | Moskowitz et al. | |
| 10,383,610 | B2 * | 8/2019 | Moskowitz | A61B 17/3403 |
| 11,000,311 | B2 * | 5/2021 | Moskowitz | A61B 17/3401 |
| 11,179,097 | B2 | 11/2021 | Moskowitz et al. | |
| 11,357,405 | B2 | 6/2022 | Puppels et al. | |
| 2004/0010204 | A1 | 1/2004 | Weber et al. | |
| 2004/0254503 | A1 | 12/2004 | Sarvazyan et al. | |
| 2004/0267121 | A1 | 12/2004 | Sarvazyan et al. | |
| 2004/0267165 | A1 | 12/2004 | Sarvazyan et al. | |
| 2005/0075665 | A1 | 4/2005 | Brenzel et al. | |
| 2006/0122555 | A1 | 6/2006 | Hochman | |
| 2006/0195043 | A1 | 8/2006 | Rutherford et al. | |
| 2006/0206118 | A1 | 9/2006 | Kim et al. | |
| 2006/0206178 | A1 | 9/2006 | Kim | |
| 2008/0015420 | A1 | 1/2008 | Zan et al. | |
| 2008/0154154 | A1 | 6/2008 | Sarvazyan et al. | |
| 2009/0018507 | A1 | 1/2009 | Schmitz et al. | |
| 2009/0131832 | A1 | 5/2009 | Sacristan et al. | |
| 2009/0143656 | A1 | 6/2009 | Manwaring et al. | |
| 2009/0157044 | A1 | 6/2009 | Liyanagama et al. | |
| 2009/0270759 | A1 | 10/2009 | Wilson et al. | |
| 2010/0256483 | A1 | 10/2010 | Wall et al. | |
| 2011/0054353 | A1 | 3/2011 | Hulvershorn et al. | |
| 2011/0066078 | A1 | 3/2011 | Sarvazyan et al. | |
| 2011/0071419 | A1 | 3/2011 | Liu et al. | |
| 2011/0092818 | A1 | 4/2011 | Sarvazyan | |
| 2011/0166442 | A1 | 7/2011 | Sarvazyan | |
| 2012/0046531 | A1 | 2/2012 | Hua | |
| 2012/0143029 | A1 | 6/2012 | Silverstein et al. | |
| 2012/0296213 | A1 * | 11/2012 | Mauldin, Jr. | A61B 8/42 600/443 |
| 2013/0023880 | A1 | 1/2013 | Tramboo et al. | |
| 2013/0085413 | A1 | 4/2013 | Tsamir et al. | |
| 2014/0046186 | A1 | 2/2014 | Mauldin, Jr. et al. | |
| 2014/0276925 | A1 | 9/2014 | Alves et al. | |
| 2014/0277045 | A1 | 9/2014 | Fazio et al. | |
| 2014/0288408 | A1 | 9/2014 | Deutsch | |
| 2014/0288427 | A1 | 9/2014 | Wall | |
| 2014/0303494 | A1 | 10/2014 | Janicki et al. | |
| 2015/0025363 | A1 | 1/2015 | Hulvershorn et al. | |
| 2015/0173667 | A1 | 6/2015 | Ben Shalom et al. | |
| 2015/0245809 | A1 | 9/2015 | Hagy et al. | |
| 2015/0342635 | A1 | 12/2015 | Tsamir et al. | |
| 2015/0359563 | A1 | 12/2015 | Kume et al. | |
| 2016/0008007 | A1 | 1/2016 | Taha | |
| 2016/0157816 | A1 | 6/2016 | Denny | |
| 2016/0270810 | A1 | 9/2016 | Vardi et al. | |
| 2017/0020540 | A1 | 1/2017 | Chou et al. | |
| 2017/0311978 | A1 * | 11/2017 | Chieng | A61B 34/30 |
| 2020/0397399 | A1 | 12/2020 | Adams et al. | |
| 2022/0039740 | A1 | 2/2022 | Moskowitz et al. | |
| 2022/0079619 | A1 | 3/2022 | Moskowitz et al. | |

FOREIGN PATENT DOCUMENTS

| | | | | |
|---|---|---|---|---|
| CN | 104140066 | A | 11/2014 | |
| CN | 104523297 | A | 4/2015 | |
| CN | 204318870 | U | 5/2015 | |
| EP | 0303824 | A2 | 2/1989 | |
| EP | 0413588 | A2 | 2/1991 | |
| EP | 2223662 | A1 | 9/2010 | |
| JP | S62281927 | A | 12/1987 | |
| JP | 2019522503 | A | 8/2019 | |
| WO | WO-9215256 | A1 | 9/1992 | |
| WO | WO-2007022599 | A1 | 3/2007 | |
| WO | WO-2007024399 | A2 | 3/2007 | |
| WO | WO-2009009621 | A2 | 1/2009 | |
| WO | WO-2009066972 | A1 | 5/2009 | |
| WO | WO-2010018536 | A2 | 2/2010 | |
| WO | WO-2010056538 | A1 | 5/2010 | |
| WO | WO-2011084788 | A2 | 7/2011 | |
| WO | WO-2011158227 | A2 | 12/2011 | |
| WO | WO-2013054165 | A1 | 4/2013 | |
| WO | WO-2013056243 | A1 | 4/2013 | |
| WO | WO-2014097301 | A1 | 6/2014 | |
| WO | WO-2015031481 | A1 | 3/2015 | |
| WO | WO-2015200712 | A1 | 12/2015 | |
| WO | WO-2016007527 | A1 | 1/2016 | |
| WO | WO-2016034910 | A1 | 3/2016 | |
| WO | WO-2017111576 | A1 * | 6/2017 | A61B 5/1455 |
| WO | WO-2017120477 | A1 | 7/2017 | |
| WO | WO-2017192596 | A1 | 11/2017 | |
| WO | WO-2018148456 | A1 | 8/2018 | |
| WO | WO-2019084502 | A1 | 5/2019 | |
| WO | WO-2021168329 | A1 | 8/2021 | |

OTHER PUBLICATIONS

European Patent Application No. 17793167.2 Extended European Search Report dated Oct. 31, 2019.
European Patent Application No. EP 18870639 Extended European Search Report dated Jun. 23, 2021.
International Application No. PCT/US2018/057860 International Preliminary Report on Patentability with Written Opinion dated May 7, 2020.

(56) References Cited

OTHER PUBLICATIONS

International Application No. PCT/US2018/057860 International Search Report and Written Opinion dated Mar. 11, 2019.
PCT/US2017/030650 International Search Report and Written Opinion dated Sep. 21, 2017.
PCT/US2018/017487 International Search Report and Written Opinion dated May 21, 2018.
PCT/US2021/018881 International Search Report and Written Opinion dated May 5, 2021.
U.S. Appl. No. 15/927,664 Final Office Action dated Apr. 16, 2021.
U.S. Appl. No. 15/584,875 First Action Interview Office Action Summary dated Oct. 12, 2017.
U.S. Appl. No. 15/584,875 First Action Interview Pilot Program, Pre-Interview Communication dated Jul. 17, 2017.
U.S. Appl. No. 15/927,664 Office Action dated Nov. 30, 2020.
U.S. Appl. No. 16/379,695 Office Action dated Sep. 22, 2020.
U.S. Appl. No. 17/239,109 Office Action dated Dec. 8, 2023.
U.S. Appl. No. 17/239,109 Office Action dated Sep. 12, 2024.

* cited by examiner

FIG. 6A
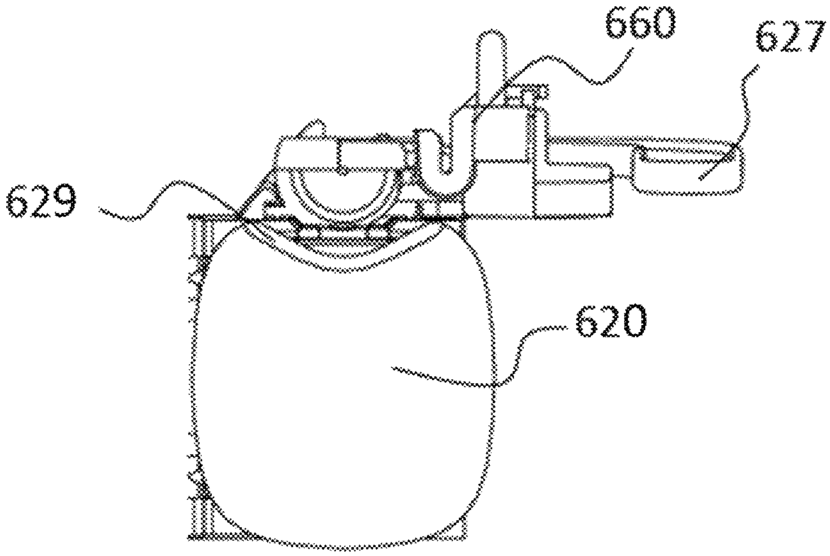
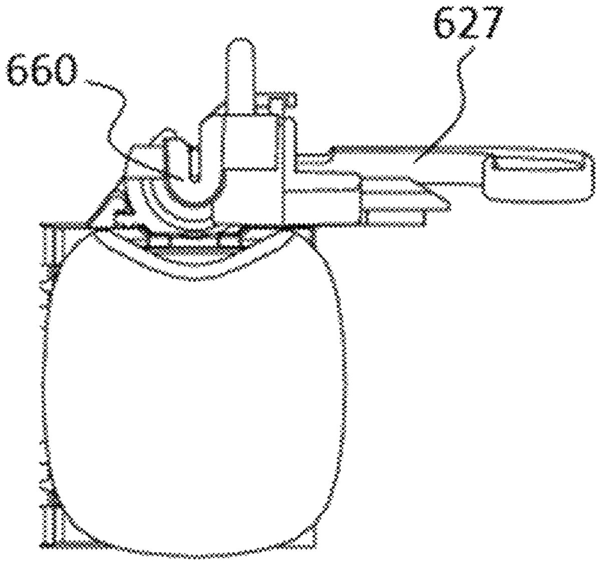
FIG. 6B
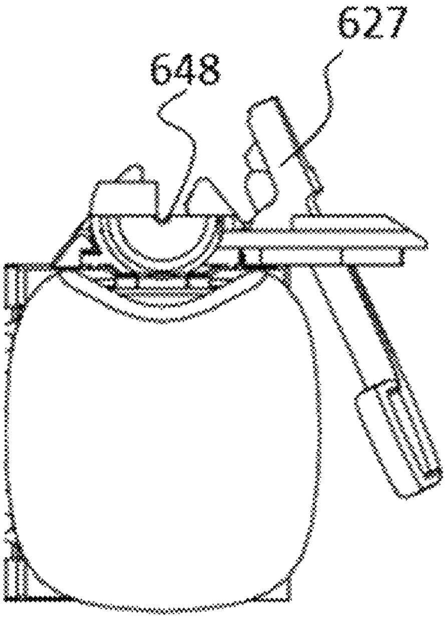
FIG. 6C

TACTILE SENSING AND GUIDANCE SYSTEM

CROSS-REFERENCE

This application is a continuation of International Application No. PCT/US2021/018881, filed Feb. 19, 2021, which claims the benefit of U.S. Provisional Application No. 63/132,960, filed Dec. 31, 2020, and U.S. Provisional Application No. 62/980,085 filed Feb. 21, 2020, which applications are incorporated herein by reference.

STATEMENT AS TO FEDERALLY SPONSORED RESEARCH

This invention was made with government support under grant number 1834481 awarded by the National Science Foundation. The government has certain rights in the invention.

SUMMARY

Provided herein are embodiments of a tactile sensing device comprising a base comprising: a scanning track; a carriage configured to slide along the scanning track; a scanhead mounted to the carriage; a sensor array attached to the scanhead, the sensor array comprising one or more pressure sensors, each pressure sensor configured to output a voltage signal in response to a change in pressure.

In some embodiments, the carriage comprises an alignment guide. In some embodiments the tactile sensing device further comprises a needle guide configured to reversibly attach to the carriage. In some embodiments, the needle guide further comprises a removal tab. In some embodiments, the tactile sensing device further comprises a needle release gate configured to reversibly attach to the carriage. In some embodiments, the needle release gate is configured to reversibly secure a needle to the carriage in a position concentric with the needle guide. In some embodiments, the scanhead further comprises a scanning knob on its proximal side. In some embodiments, the base comprises at least one restrictor guide configured to restrict an insertion depth of an injection needle. In some embodiments, the scanning knob comprises at least one restrictor guide. In some embodiments, the scanning knob comprises two or more restrictor guides configured to restrict the insertion depth of an injection needle, and wherein the scanning knob rotates to align one of said two or more restrictor guides with the alignment guide.

In some embodiments, the tactile sensing device further comprises a bottom pad forming a distal surface of the tactile sensing device. In some embodiments, the bottom pad is configured to rest on a skin surface of a patient. In some embodiments, the bottom pad is provided with a concave curvature having radius of approximately 1 meter. In some embodiments, the bottom pad comprises a hardness of approximately 20 Shore A to 30 Shore A.

In some embodiments, the scanhead is moveable relative to the carriage. In some embodiments, the scanhead is biased toward a proximal side of the device. In some embodiments, the scanhead is biased by a spring. In some embodiments, the carriage comprises a spring guide. In some embodiments, wherein the scanning knob comprises a spring protrusion, and wherein the carriage comprises spring guide, wherein the spring guide and the spring protrusion are configured to center the spring relative to the scanhead and the carriage.

In some embodiments, the sensor array is a matrix array. In some embodiments, the sensor array is a flexible sensor array. In some embodiments, the sensor array is attached to a sensor array attachment area. In some embodiments, the sensor array is adhered to a distal surface of the tactile sensing device.

In some embodiments, the base further comprises a handle. In some embodiments, the handle comprises a grip feature. In some embodiments, the needle guide further comprises a connector plate. In some embodiments, the device further comprising a connector coupled to a depth restrictor, wherein the connector removably attaches to the connector plate of the needle guide, thereby allowing the depth restrictor to be placed in a first position in alignment with the needle guide and a second position out of alignment with the needle guide. In some embodiments, the connector is coupled to the depth restrictor to allow the depth restrictor to be positioned at an upper position away from the needle guide or at a lower position proximal to the needle guide. In some embodiments, the upper position is configured for placement of a 5 inch needle. In some embodiments, the upper position limits the depth of a 5 inch needle from about 0.5 centimeters to about 5 centimeters. In some embodiments, the lower position is configured for placement of a 3.5 inch needle. In some embodiments, the upper position limits the depth of a 3.5 inch needle from about 1 centimeter to about 3.5 centimeters. In some embodiments, the device further comprising a needle release gate configured to reversibly attach to the carriage.

The tactile sensing device of some embodiments, wherein the needle release gate is configured to reversibly secure a needle to the carriage in a position concentric with the needle guide In some embodiments, the tactile sensing device further comprises a locking mechanism which prevents the carriage from sliding along the scanning track when the scanhead is depressed. In some embodiments, the locking mechanism comprises one or more locking tabs having a pointed protrusion which engage with an elastomeric strip when the scanhead is depressed. In some embodiments, the base further comprises a position sensor.

In some embodiments, the tactile sensing device further comprises a monitor device, comprising: a display screen operatively coupled to the sensor array, the display screen configured to display: a pressure map representing a target tissue location in an individual based upon the voltage signals output by the one or more pressure sensors; and a computing device comprising a processor operatively coupled to the sensor unit and the monitor device, and a non-transitory computer readable storage medium with a computer program including instructions executable by the processor causing the processor to: i) convert the voltage signals from the sensor array into the pressure map and display the pressure map on the display screen and ii) output an alignment guide location on the display screen.

In some embodiments, the base further comprises an interface configured to receive the monitor device. In some embodiments, the interface comprises an electrical coupling such that the sensor array is in electrical communication with the monitor device when the monitor device is received by the interface. In some embodiments, the sensor array is electrically coupled to the interface by a flexible printed circuit board. In some embodiments, the monitor device is coupled to the sensor array via a flexible printed circuit board. In some embodiments, the monitor device comprises a printed circuit board.

In some embodiments, the tactile sensing device further comprises a sleeve configured for receiving the monitor device. In some embodiments, the tactile sensing device comprises a power source. In some embodiments, the power source is a battery located within the monitor device. In some embodiments, the sensor unit and the monitor device are reversibly connected.

In some embodiments, the tactile sensing device comprises a wireless transmitter, the wireless transmitter operatively connected to the sensor array, for remotely transmitting the voltage signals output by the plurality of sensors. In some embodiments, the processor is configured with instructions to display the target tissue location and the alignment guide location on the display screen. on the display screen in real time. In some embodiments, the processor is configured with instructions to display a force being applied to the target tissue location in real time.

In some embodiments, the base further comprises a midline indicator. In some embodiments, a distance between a distal surface of the base and a distal surface of the scanhead is approximately 0.1 cm to 5 cm. In some embodiments, a distance between a distal surface of the base and a distal surface of the scanhead is approximately 0.2 cm. In some embodiments, an active area of the sensor array is approximately 350 $mm^2$. In some embodiments, the distal surface of the scan head is curved. In some embodiments, the radius of curvature of the scan head is about 37.5 millimeters.

In some embodiments, the device further comprises a depth lock to lock a position of the scanhead at a depth relative to the carriage. In some embodiments, the device further comprises a button to release the scan head from a locked position relative to the carriage. In some embodiments, the flexible printed circuit board electrically connects a position sensor to the monitor device. In some embodiments, the position sensor is operatively coupled to the processor of the computing device, and wherein the computing device receives a position of the sensor array from the position sensor, and wherein the position of the sensor array is utilized to generate the pressure map.

In some embodiments, an active area of the sensor array is approximately 350 $mm^2$. In some embodiments, the scanhead further comprises a scanning knob on its proximal side. In some embodiments, the base comprises at least one restrictor guide configured to restrict an insertion depth of a needle. In some embodiments, the scanning knob comprises at least one restrictor guide. In some embodiments, the scanning knob comprises two or more restrictor guides configured to restrict the insertion depth of a needle, and wherein the scanning knob rotates to align one of said two or more restrictor guides with the alignment guide.

Provided herein are embodiments of a tactile sensing system, comprising a base, comprising: a scanning track; a carriage configured to slide along the scanning track; a scanhead mounted to the carriage; and a sensor array attached to the scanhead, the sensor array comprising one or more pressure sensors, each pressure sensor configured to output a voltage signal in response to a change in pressure; and a monitor device, comprising: a display screen operatively coupled to the sensor array, the display screen configured to display: a pressure map representing a target tissue location in an individual based upon the voltage signals output by the one or more pressure sensors; and a computing device comprising a processor operatively coupled to the sensor unit and the monitor device, and a non-transitory computer readable storage medium with a computer program including instructions executable by the processor causing the processor to: i) convert the voltage signals from the sensor array into the pressure map and display the pressure map on the display screen and ii) output an alignment guide location on the display screen.

In some embodiments, the base further comprises an interface configured to receive the monitor device. In some embodiments, wherein in the interface comprises an electrical coupling such that the sensor array is in electrical communication with the monitor device when the monitor device is received by the interface. In some embodiments, the sensor array is electrically coupled to the interface by a flexible printed circuit board.

In some embodiments, the base further comprises a position sensor. In some embodiments, the carriage comprises an alignment guide. In some embodiments, the tactile sensing system further comprises a needle guide configured to reversibly attach to the carriage. In some embodiments, the needle guide further comprises a removal tab. In some embodiments, the tactile sensing system further comprises a needle release gate configured to reversibly attach to the carriage. In some embodiments, the needle release gate is configured to reversibly secure an injection needle to the carriage in a position concentric with the needle guide.

In some embodiments, the scanhead further comprises a scanning knob on its proximal side. In some embodiments, the scanning knob comprises at least one restrictor guide configured to restrict an insertion depth of an injection needle. In some embodiments, the scanning knob comprises two or more restrictor guides configured to restrict the insertion depth of an injection needle, and wherein the scanning knob rotates to align one of said two or more restrictor guides with the alignment guide.

In some embodiments, the base further comprises a midline indicator. In some embodiments, a distance between a distal surface of the base and a distal surface of the scanhead is approximately 0.1 cm to 5 cm. In some embodiments, a distance between a distal surface of the base and a distal surface of the scanhead is approximately 0.2 cm. In some embodiments, an active area of the sensor array is approximately 350 $mm^2$.

In some embodiments, the tactile sensing device further comprises a bottom pad forming a distal surface of the tactile sensing system. In some embodiments, the bottom pad is configured to rest on a skin surface of a patient. In some embodiments, wherein the bottom pad is provided with a concave curvature having radius of approximately 1 meter. In some embodiments, the bottom pad comprises a hardness of approximately 20 Shore A to 35 Shore A.

In some embodiments, the scanhead is moveable relative to the carriage. In some embodiments, wherein the scanhead is biased toward a proximal side of the system. In some embodiments, the scanhead is biased by a spring. In some embodiments, the scanhead comprises a spring protrusion, and wherein the spring guide and the spring protrusion are configured to center the spring relative to the scanhead and the carriage. In some embodiments, the sensor array is a matrix array. In some embodiments, the sensor array is a flexible sensor array. In some embodiments, the sensor array is attached to a sensor array attachment area. In some embodiments, the sensor array is adhered to a distal surface of the scanhead.

In some embodiments, the base further comprises a handle. In some embodiments, the handle comprises a grip feature. In some embodiments, the tactile sensing system further comprises a locking mechanism which prevents the carriage from sliding along the scanning track when the scanhead is depressed. In some embodiments, wherein locking mechanism comprises one or more locking tabs having a pointed protrusion which engage with an elastomeric strip when the scanhead is depressed.

In some embodiments, the monitor device is coupled to the sensor array via a flexible printed circuit board. In some embodiments, the monitor device comprises a printed circuit board. In some embodiments, the tactile sensing system further comprises a sleeve configured for receiving the monitor device. In some embodiments, the tactile sensing system further comprises a power source. In some embodiments, the power source is a battery located within the monitor device.

In some embodiments, the sensor unit and the monitor device are reversibly connected. In some embodiments, the tactile sensing system comprises a wireless transmitter, the wireless transmitter operatively connected to the sensor array, for remotely transmitting the voltage signals output by the plurality of sensors. In some embodiments, the processor is configured with instructions to display the target tissue location and the alignment guide location on the display screen in real time. In some embodiments, the processor is configured with instructions to display a force being applied to the target tissue location in real time.

In some embodiments, a method of locating an insertion site using the system comprises: sliding the carriage over a target tissue location; depressing the scanhead into the target tissue location to capture a pressure map image on the display screen; reading an applied force measurement from a force indicator; releasing the scanhead; sliding the carriage toward an unmapped area of the target tissue location; and repeating the steps until a pressure map is displayed across the target tissue location.

In some embodiments, the position sensor is operatively coupled to the processor of the computing device, and wherein the computing device receives a position of the sensor array from the position sensor, and wherein the position of the sensor array is utilized to generate the pressure map. In some embodiments, the position sensor is electrically coupled to the interface via a flexible printed circuit board.

In some embodiments, method of marking an insertion site using the system comprises: sliding the carriage over a target tissue location; depressing the scanhead into the target tissue location to capture a pressure map image on the display screen; reading an applied force measurement from a force indicator; releasing the scanhead; sliding the carriage toward an unmapped area of the target tissue location; repeating the prior steps until a pressure map is displayed across the target tissue location; identifying an insertion site, placing the alignment guide at the location of the insertion site on the pressure map; placing a marking utensil through the alignment guide; and marking the insertion site on a skin surface of a patient.

In some embodiments, a method of guiding a needle into an insertion site using the system comprises: sliding the carriage over a target tissue location; depressing the scanhead into the target tissue location to capture a pressure map image on the display screen; releasing the scanhead; sliding the carriage toward an unmapped area of the target tissue location; and repeating steps until a pressure map is displayed across the target tissue location; placing the alignment guide location at the insertion site on the pressure map; placing a needle through the needle guide; and depressing the scan head to guide the needle into the insertion site. In some embodiments, the method further comprises a step of removing the system while retaining the needle in the insertion site.

In some embodiments, the method further comprises reading an applied force measurement from a force indicator. In some embodiments, method of guiding a needle into an insertion and treating a patient site using the system comprises: sliding the carriage over a target tissue location; depressing the scanhead into the target tissue location to capture a pressure map image on the display screen; reading an applied force measurement from a force indicator; releasing the scanhead; sliding the carriage toward an unmapped area of the target tissue location; repeating the prior steps until a pressure map is displayed across the target tissue location; placing the alignment guide location at the insertion site on the pressure map; placing a needle through the needle guide; and inserting the needle into the insertion site. In some embodiments, the needle is a local anesthetic needle and the method further comprises a step of injecting a local anesthesia into the insertion site. In some embodiments, the method further comprises a step of removing the local anesthetic needle; placing a spinal anesthesia needle through the needle guide; and inserting the spinal anesthesia needle into the insertion site. In some embodiments, the method further comprises a step of removing the local anesthetic needle; placing an introducer needle through the needle guide; and inserting the introducer needle into the insertion site. In some embodiments the method further comprises a step of removing the system. In some embodiments, the step of removing the system further comprises opening the release gate. In some embodiments, the method further comprises a step of proceeding with a method of treatment after the step of removing the system. The method of some embodiments, further comprising a step of unlocking a release gate prior to the step of removing the system.

In some embodiments, the needle is a local anesthetic needle and the method further comprises a step of injecting a local anesthesia into the insertion site. In some embodiments, the method further comprises a step of removing the local anesthetic needle; placing a spinal anesthesia needle through the needle guide; and inserting the spinal anesthesia needle into the insertion site. In some embodiments, the method further comprises a step of removing the local anesthetic needle; placing an introducer needle through the needle guide; and inserting the introducer needle into the insertion site. In some embodiments, the method further comprises a step of removing the system. In some embodiments, the step of removing the system comprises opening the release gate. In some embodiments, the method further comprises a step of proceeding with a method of treatment after the step of removing the system.

In some embodiments, the needle is an introducer. In some embodiments, the method further comprises a step of configuring a depth restrictor prior to the step of placing the needle through the needle guide. In some embodiments, the step of configured the depth restrictor comprises setting a height of the depth restrictor. In some embodiments, wherein setting the height of the depth restrictor comprises setting the depth restrictor to a lower position.

In some embodiments, the method further comprises locking the depth restrictor in the lower position. In some embodiments, setting the height of the depth restrictor comprises setting the depth restrictor to an upper position. In some embodiments, the method further comprises locking the depth restrictor in the upper position.

In some embodiments, provided herein are methods of locating an insertion site using a tactile sensing device, the tactile sensing device comprising: a base comprising: a scanning track; a carriage configured to slide along the scanning track, the carriage comprising an alignment guide;

a scanhead mounted to the carriage; a sensor array attached to the scanhead, the sensor array comprising one or more pressure sensors, each pressure sensor configured to output a voltage signal in response to a change in pressure; and a monitor device, comprising: a display screen operatively coupled to the sensor array, the display screen configured to display: a pressure map representing a target tissue location in an individual based upon the voltage signals output by the one or more pressure sensors; and a computing device comprising a processor operatively coupled to the sensor unit and the monitor device, and a non-transitory computer readable storage medium with a computer program including instructions executable by the processor causing the processor to: i) convert the voltage signals from the sensor array into the pressure map and display the pressure map on the display screen and ii) output an alignment guide location on the display screen; and the method comprising: (a) sliding the carriage over a target tissue location; (b) depressing the scanhead into the target tissue location to capture a pressure map image on the display screen; (c) releasing the scanhead; (d) sliding the carriage toward an unmapped area of the target tissue location; and (e) repeating steps (b) to (d) until a pressure map is displayed across the target tissue location.

In some embodiments, the method further comprises identifying an insertion site; and placing the alignment guide location at the insertion site. In some embodiments, the method further comprises placing a needle through the needle guide; and inserting the needle into the insertion site. In some embodiments, the method further comprises placing a marking utensil through the alignment guide; and marking the insertion site on a skin surface of a patient. In some embodiments, the method further comprises a step of removing the system while retaining the needle in the insertion site. In some embodiments, the method further comprises a step of unlocking a release gate prior to the step of removing the system.

In some embodiments, the needle is a local anesthetic needle and the method further comprises a step of injecting a local anesthesia into the insertion site. In some embodiments, the method further comprises a step of removing the local anesthetic needle; placing a spinal anesthesia needle through the needle guide; and inserting the spinal anesthesia needle into the insertion site. In some embodiments, the method further comprises a step of removing the local anesthetic needle; placing an introducer needle through the needle guide; and inserting the introducer needle into the insertion site. In some embodiments, the method further comprises a step of removing the system. In some embodiments, the step of removing the system comprises opening the release gate. In some embodiments, the method further comprises a step of proceeding with a method of treatment after the step of removing the system.

In some embodiments, the needle is an introducer. In some embodiments, the method further comprises a step of configuring a depth restrictor prior to the step of placing the needle through the needle guide. In some embodiments, the step of configured the depth restrictor comprises setting a height of the depth restrictor. In some embodiments, setting the height of the depth restrictor comprises setting the depth restrictor to a lower position. In some embodiments, the method further comprises locking the depth restrictor in the lower position. In some embodiments, setting the height of the depth restrictor comprises setting the depth restrictor to an upper position. In some embodiments, the method further comprises locking the depth restrictor in the upper position.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A shows needle guide subassembly and release gate component coupled to a carriage component of a tactile sensing and guidance system, according to some embodiments;

FIG. 6B shows needle guide component and release gate component coupled to a carriage component of a tactile sensing and guidance system, according to some embodiments;

FIG. 6C shows needle guide component and release gate component coupled to a carriage component of a tactile sensing and guidance system, according to some embodiments;

DETAILED DESCRIPTION

Provided herein are embodiments of a tactile sensing and needle guidance system. In some embodiments the tactile sensing and needle guidance system is a sliding system comprising a scanhead mounted to a carriage to facilitate movement along a scanning track. In some embodiments the tactile sensing and needle guidance system further comprises a monitoring device which displays a pressure map and alignment guide indicator to facilitate marking and/or insertion of a needle into a target location of a patient in need thereof.

I. SLIDING TACTILE SENSING AND NEEDLE GUIDANCE SYSTEM

According to some embodiments, the tactile sensing device is a sliding tactile sensing system. A sliding tactile sensing system and relevant components are depicted in FIGS. 1-8B. In some embodiments, the tactile sensing system includes historical and real time image visualization thereby requiring a smaller sensor array to build an image for display of the anatomy of a subject as compared to a non-sliding tactile sensing device.

Figure 1:
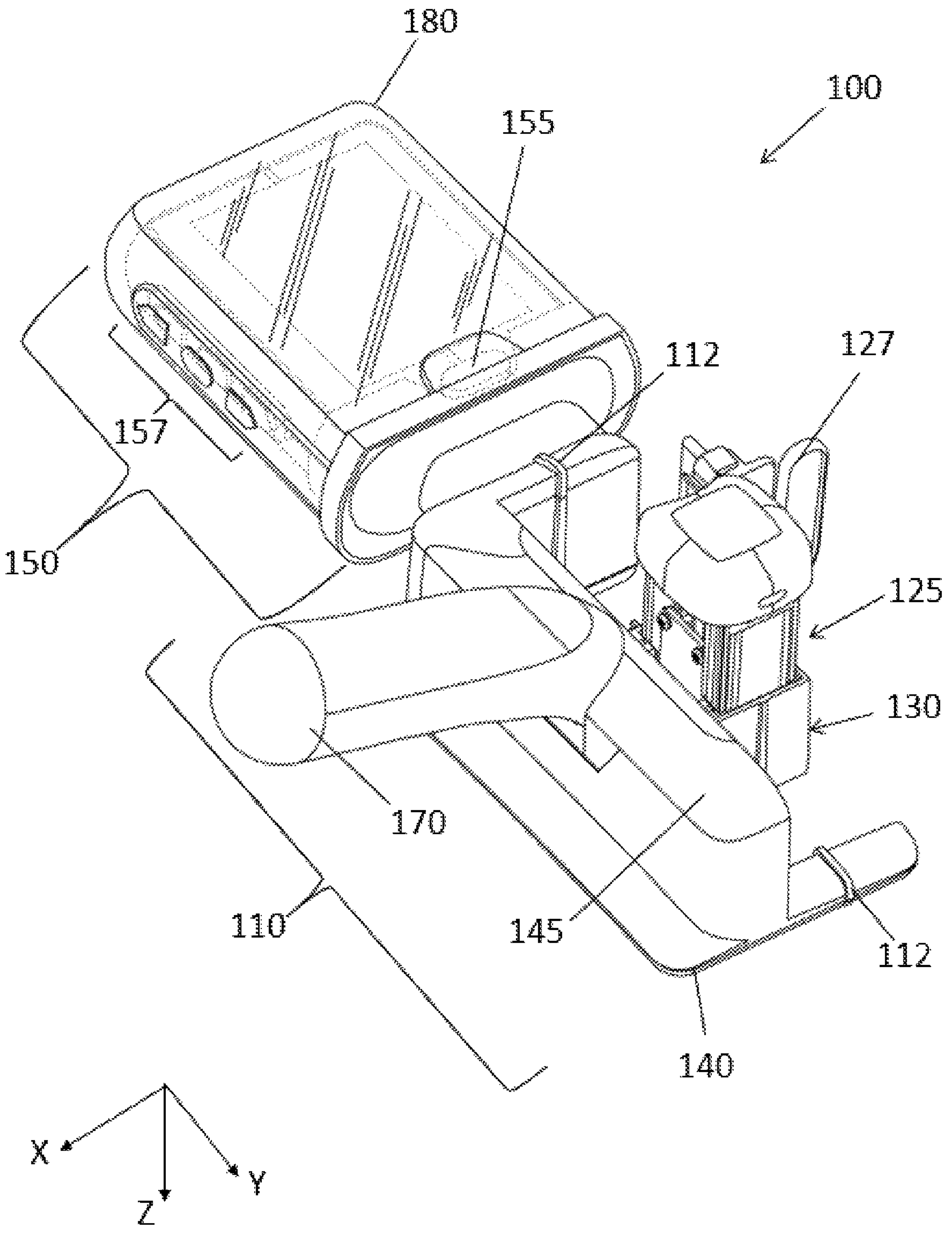
FIG. 1 shows a tactile sensing and guidance system, according to some embodiments.

FIG. 1 depicts a tactile sensing system 100, according to some embodiments. In some embodiments, the tactile sensing system 100 comprises a monitor device 150 which is detachable from the base 110. In some embodiments, the slider tactile sensing device 100 comprises a scanhead subassembly comprising a scanhead 125 and carriage 130. In some embodiments, the scanhead 125 mates with the carriage 130 configured to enable the user to depress the scanhead 125 and press a sensor array (e.g. sensor array 435 as depicted in FIG. 4) onto a skin surface a patient. In some embodiments, the base 110 comprises a scanning track 145. In some embodiments, the scanning track is configured to translate the scanhead subassembly along a distance (e.g., along the vertebrae of a patient).

In some embodiments, the carriage 130 allows the scanhead 125 and the sensor array to be translated over a distance (e.g., along a 3 inch distance along the vertebrae). In some embodiments, the scanhead 125 is translated over a distance of about 0.5 inches (in.) to about 10 in. In some embodiments, the scanhead 125 is translated over a distance of at least about 0.5 in. In some embodiments, the scanhead 125 is translated over a distance of at most about 10 in. In some embodiments, the scanhead 125 is translated over a distance of about 0.5 in. to about 1 in., about 0.5 in. to about 2 in., about 0.5 in. to about 3 in., about 0.5 in. to about 4 in., about 0.5 in. to about 5 in., about 0.5 in. to about 6 in., about 0.5 in. to about 7 in., about 0.5 in. to about 8 in., about 0.5 in. to about 9 in., about 0.5 in. to about 10 in., about 1 in. to about 2 in., about 1 in. to about 3 in., about 1 in. to about 4 in., about 1 in. to about 5 in., about 1 in. to about 6 in., about 1 in. to about 7 in., about 1 in. to about 8 in., about 1 in. to about 9 in., about 1 in. to about 10 in., about 2 in. to about 3 in., about 2 in. to about 4 in., about 2 in. to about 5 in., about 2 in. to about 6 in., about 2 in. to about 7 in., about 2 in. to about 8 in., about 2 in. to about 9 in., about 2 in. to about 10 in., about 3 in. to about 4 in., about 3 in. to about 5 in., about 3 in. to about 6 in., about 3 in. to about 7 in., about 3 in. to about 8 in., about 3 in. to about 9 in., about 3 in. to about 10 in., about 4 in. to about 5 in., about 4 in. to about 6 in., about 4 in. to about 7 in., about 4 in. to about 8 in., about 4 in. to about 9 in., about 4 in. to about 10 in., about 5 in. to about 6 in., about 5 in. to about 7 in., about 5 in. to about 8 in., about 5 in. to about 9 in., about 5 in. to about 10 in., about 6 in. to about 7 in., about 6 in. to about 8 in., about 6 in. to about 9 in., about 6 in. to about 10 in., about 7 in. to about 8 in., about 7 in. to about 9 in., about 7 in. to about 10 in., about 8 in. to about 9 in., about 8 in. to about 10 in., or about 9 in. to about 10 in. In some embodiments, the scanhead 125 is translated over a distance of about 0.5 in., about 1 in., about 2 in., about 3 in., about 4 in., about 5 in., about 6 in., about 7 in., about 8 in., about 9 in., or about 10 in.

In some embodiments, the surface of the distal side, with respect to the user (i.e., the bottom surface), of the scanhead 125 comprises a sensor array. In some embodiments, the scanhead 125 is configured to receive the scanning knob 120. In some embodiments, the sensor array (e.g. sensor array 435 as depicted in FIG. 4) is mounted on the bottom surface of the scanhead 120. In some embodiments, a bottom or distal surface of the scanhead 125, on which the sensor array is provided, has a size and curvature designed to mimic palpation and optimize vertebral resolution of a pressure map generated from the sensing elements or sensors of the sensor array. In some embodiments, the bottom surface of the scanhead is about 30 millimeters (mm) in length and about 21 mm in width. In some embodiments, the bottom surface of the scanhead has a radius of curvature of approximately 37.5 mm. In some embodiments, the scanhead 125 may be depressed, such that the scanhead moves relative to the carriage (i.e. along the Z-axis) toward a bottom surface of the base 110.

As shown in FIG. 1, the base 110 of the tactile sensing system 100 may comprise a grip feature 170. In some embodiments, the grip feature 170 is reversibly attachable to the base 110. In some embodiments, the user grasps the grip feature 170 to stabilize the device against a patient. In some embodiments, the grip feature 170 is an ergonomic handle: extending to one side of the base 110, similar to a bicycle grip. In some embodiments, the grip feature 170 extends to the left side of the base to allowing the user to grip the grip feature 170 with their left hand while engaging the scanhead 125 with their right hand. In another embodiment, the grip feature 170 extends to the right side of the base to allowing the user to grip the grip feature 170 with their right hand while engaging the scanhead 125 with their left hand.

In some embodiments, the base 110 of the tactile sensing device comprises a support 140. In some embodiments, the support 140 comprises an indicator for the midline 112 of the tactile sensing device to facilitate alignment with the spine. In some embodiments, the indicator for the midline 112 is provided on the body of the base 110. In some embodiments the indicator for the midline 112 of the tactile sensing device further comprises an alignment guide. In some embodiments, the indicator is a colored notch. In some embodiments, a midline indicator 112 is provided on the carriage 130. In some embodiments, a midline indicator is provided on the scanning knob 120.

In some embodiments, a scanhead subassembly comprises a scanhead 125, a scanning knob 120, and a carriage 130. In some embodiments, the tactile sensing device 100 comprises a scanning track 145 (also see 245 in FIG. 2A). In some embodiments, the scanning track 145 is part of the base 110. In some embodiments the scanning track 145 is a removable part that is assembled with the base 110. In some embodiments, the scanning track 145 comprises a track 145 that is configured to translate the carriage 130 and scanhead 125 along the skin surface of the patient. In some embodiments, the scanning track 145 is configured to receive the carriage 130. In some embodiments, the carriage 130 snaps into the scanning track 145. In some embodiments, the scanning track 145 comprises an elastomeric strip which interfaces with protrusions of the carriage 130 when the scanhead 125 is depressed relative to the carriage and locks the carriage in the current position along the scanning track.

In some embodiments, the scanning track 145 is about 2.5 inches to about 3 inches and allows travel of the carriage 130 travel along the track. In some embodiments, the length of the scanning track is based on the distance between the top and bottom of consecutive spinous processes. In some embodiments, the scanning track 145 has a length of about 1 cm to about 10 cm. In some embodiments, the scanning track 145 has a length of at least about 1 cm. In some embodiments, the scanning track 145 allows for a scanhead travel distance of at most about 10 cm. In some embodiments, the scanning track 145 has a length of about 1 cm to about 2 cm, about 1 cm to about 3 cm, about 1 cm to about 4 cm, about 1 cm to about 5 cm, about 1 cm to about 6 cm, about 1 cm to about 7 cm, about 1 cm to about 8 cm, about 1 cm to about 9 cm, about 1 cm to about 10 cm, about 2 cm to about 3 cm, about 2 cm to about 4 cm, about 2 cm to about 5 cm, about 2 cm to about 6 cm, about 2 cm to about 7 cm, about 2 cm to about 8 cm, about 2 cm to about 9 cm, about 2 cm to about 10 cm, about 3 cm to about 4 cm, about 3 cm to about 5 cm, about 3 cm to about 6 cm, about 3 cm to about 7 cm, about 3 cm to about 8 cm, about 3 cm to about 9 cm, about 3 cm to about 10 cm, about 4 cm to about 5 cm, about 4 cm to about 6 cm, about 4 cm to about 7 cm, about 4 cm to about 8 cm, about 4 cm to about 9 cm, about 4 cm to about 10 cm, about 5 cm to about 6 cm, about 5 cm to about 7 cm, about 5 cm to about 8 cm, about 5 cm to about 9 cm, about 5 cm to about 10 cm, about 6 cm to about 7 cm, about 6 cm to about 8 cm, about 6 cm to about 9 cm, about 6 cm to about 10 cm, about 7 cm to about 8 cm, about 7 cm to about 9 cm, about 7 cm to about 10 cm, about 8 cm to about 9 cm, about 8 cm to about 10 cm, or about 9 cm to about 10 cm. In some embodiments, the scanning track 145 has a length of about 1 cm, about 2 cm, about 3 cm, about 4 cm, about 5 cm, about 6 cm, about 7 cm, about 8 cm, about 9 cm, or about 10 cm.

In some embodiments, the scanhead 130 is biased toward the proximal side of the tactile sensing device 100, away from the bottom surface of the support 140, such that a clearance distance is provided between the bottom surface of the support and the sensor array 135 provided on the distal surface of the scanhead 130. In some embodiments, the clearance distance is about 1.8 millimeters. In some embodiments, the clearance distance between the support and the distal surface of the scanhead is about 0.1 cm to about 5 cm. In some embodiments, the clearance distance between the support and the distal surface of the scanhead is about 0.1 cm to about 0.5 cm, about 0.1 cm to about 1 cm, about 0.1 cm to about 1.5 cm, about 0.1 cm to about 2 cm, about 0.1 cm to about 2.5 cm, about 0.1 cm to about 3 cm, about 0.1 cm to about 3.5 cm, about 0.1 cm to about 4 cm, about 0.1 cm to about 4.5 cm, about 0.1 cm to about 5 cm, about 0.5 cm to about 1 cm, about 0.5 cm to about 1.5 cm, about 0.5 cm to about 2 cm, about 0.5 cm to about 2.5 cm, about 0.5 cm to about 3 cm, about 0.5 cm to about 3.5 cm, about 0.5 cm to about 4 cm, about 0.5 cm to about 4.5 cm, about 0.5 cm to about 5 cm, about 1 cm to about 1.5 cm, about 1 cm to about 2 cm, about 1 cm to about 2.5 cm, about 1 cm to about 3 cm, about 1 cm to about 3.5 cm, about 1 cm to about 4 cm, about 1 cm to about 4.5 cm, about 1 cm to about 5 cm, about 1.5 cm to about 2 cm, about 1.5 cm to about 2.5 cm, about 1.5 cm to about 3 cm, about 1.5 cm to about 3.5 cm, about 1.5 cm to about 4 cm, about 1.5 cm to about 4.5 cm, about 1.5 cm to about 5 cm, about 2 cm to about 2.5 cm, about 2 cm to about 3 cm, about 2 cm to about 3.5 cm, about 2 cm to about 4 cm, about 2 cm to about 4.5 cm, about 2 cm to about 5 cm, about 2.5 cm to about 3 cm, about 2.5 cm to about 3.5 cm, about 2.5 cm to about 4 cm, about 2.5 cm to about 4.5 cm, about 2.5 cm to about 5 cm, about 3 cm to about 3.5 cm, about 3 cm to about 4 cm, about 3 cm to about 4.5 cm, about 3 cm to about 5 cm, about 3.5 cm to about 4 cm, about 3.5 cm to about 4.5 cm, about 3.5 cm to about 5 cm, about 4 cm to about 4.5 cm, about 4 cm to about 5 cm, or about 4.5 cm to about 5 cm. In some embodiments, the clearance distance between the support and the distal surface of the scanhead is about 0.1 cm, about 0.5 cm, about 1 cm, about 1.5 cm, about 2 cm, about 2.5 cm, about 3 cm, about 3.5 cm, about 4 cm, about 4.5 cm, or about 5 cm. In some embodiments, the clearance distance between the support and the distal surface of the scanhead is at least about 0.1 cm, about 0.5 cm, about 1 cm, about 1.5 cm, about 2 cm, about 2.5 cm, about 3 cm, about 3.5 cm, about 4 cm, or about 4.5 cm. In some embodiments, the clearance distance between the support and the distal surface of the scanhead is at most about 0.5 cm, about 1 cm, about 1.5 cm, about 2 cm, about 2.5 cm, about 3 cm, about 3.5 cm, about 4 cm, about 4.5 cm, or about 5 cm.

Figure 2A:
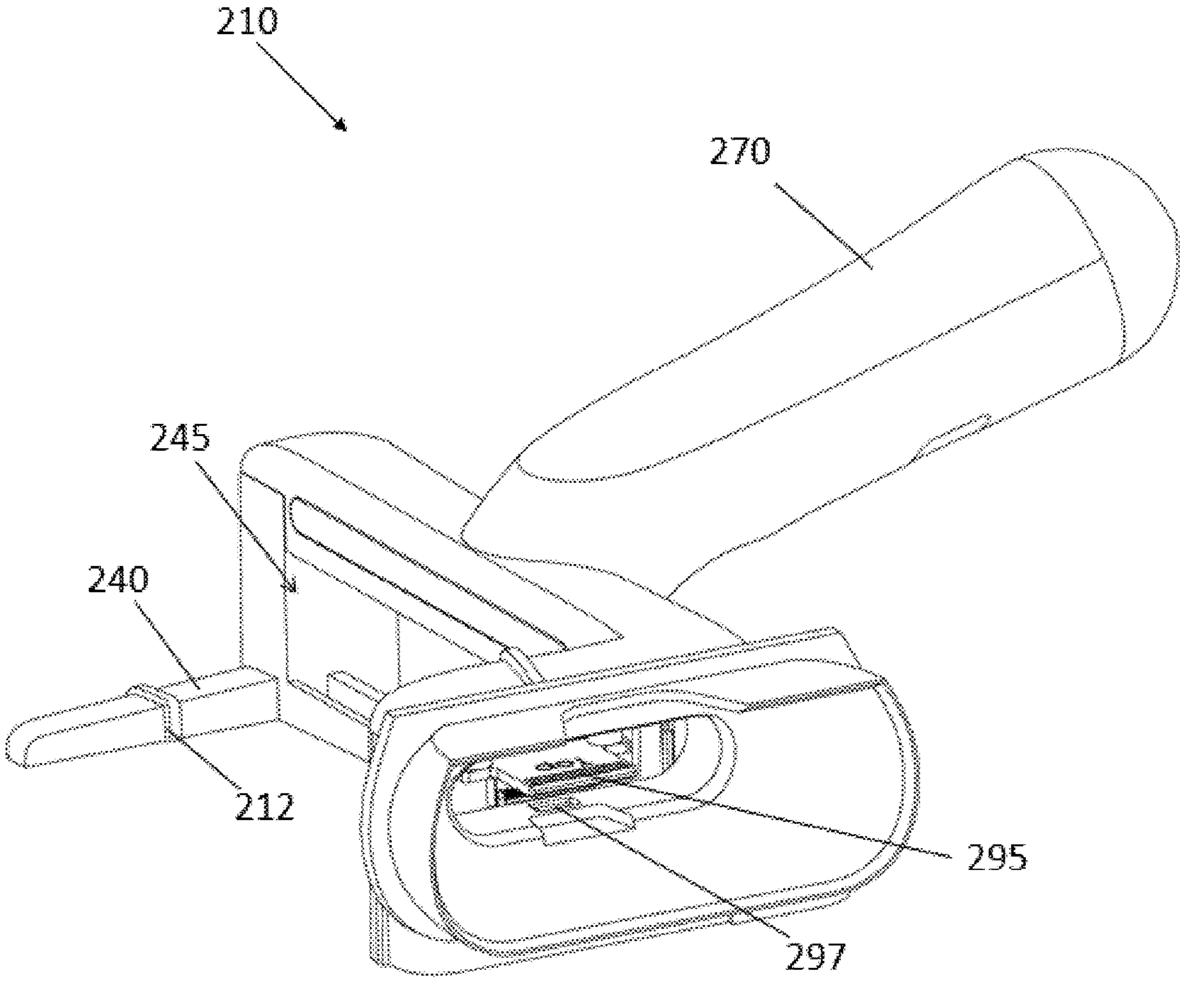
FIG. 2A shows a base component of a tactile sensing and guidance system, according to some embodiments.
Figure 2B:
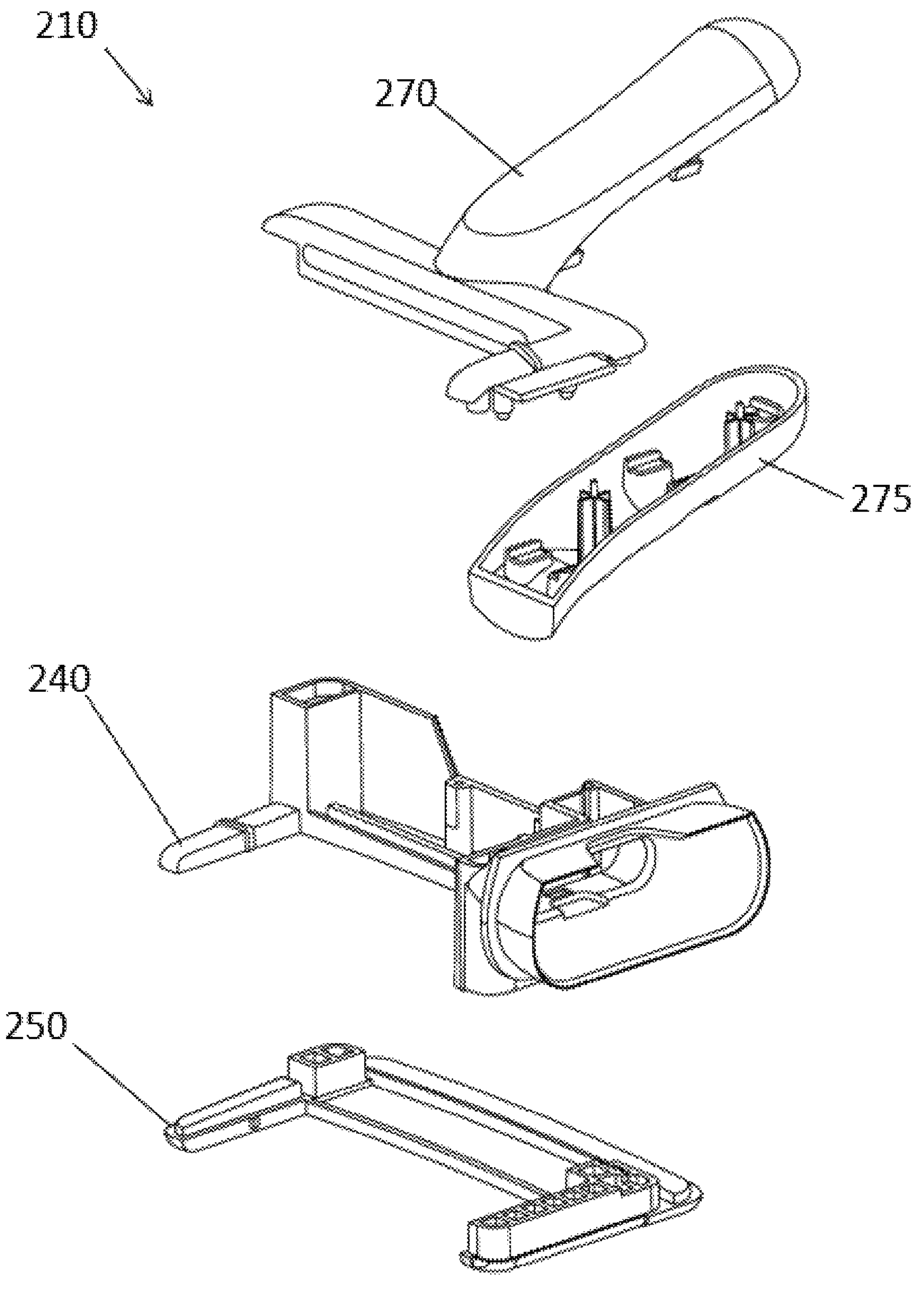
FIG. 2B shows a base component of a tactile sensing and guidance system, according to some embodiments.

FIGS. 2A and 2B depict embodiments of the base component 210. In some embodiments, the base 210 is reusable. In some embodiments, the base 210 is disposable. In some embodiments, the base 210 is made of medical-grade, injection-molded plastic. In some embodiments, the base 210 is comprised of four parts. In some embodiments, the base 210 comprises a handle 270. In some embodiments, the second component forms the bottom of the handle 275. In some embodiments, the base further comprises the support 240. In some embodiments, the support 240 houses the flexible printed circuit board and interface 295 for electrically connecting the sensor array and/or position sensor to the monitoring device, as further disclosed herein. In some embodiments, the support comprises a midline indicator 212. Components of the base may mate via a press fit. Components of the base may be secured together with adhesive or via one or more fastening devices such as screws.

In some embodiments, the support 240 comprises a patient-contacting mechanism on the bottom surface. In some embodiments, the patient-contacting mechanism is configured for device placement and stabilization. In some embodiments, the patient-contacting mechanism is configured to prevent slippage of the device during use. In some embodiments, the patient-contacting mechanism employs a vacuum, an adhesive, tacky substrate, bottom pad, or a belt mechanism.

In some embodiments, a bottom pad 250 forms a surface of the base 210 which contacts the patient. In some embodiments, the bottom pad 250 has a hardness of about 25 to 35 Shore A. In some embodiments, the bottom pad 250 has a hardness of about 10 Shore A to about 40 Shore A. In some embodiments, the bottom surface of the support 240 has a hardness of about 10 Shore A to about 15 Shore A, about 10 Shore A to about 20 Shore A, about 10 Shore A to about 25 Shore A, about 10 Shore A to about 30 Shore A, about 10 Shore A to about 35 Shore A, about 10 Shore A to about 40 Shore A, about 15 Shore A to about 20 Shore A, about 15 Shore A to about 25 Shore A, about 15 Shore A to about 30 Shore A, about 15 Shore A to about 35 Shore A, about 15 Shore A to about 40 Shore A, about 20 Shore A to about 25 Shore A, about 20 Shore A to about 30 Shore A, about 20 Shore A to about 35 Shore A, about 20 Shore A to about 40 Shore A, about 25 Shore A to about 30 Shore A, about 25 Shore A to about 35 Shore A, about 25 Shore A to about 40 Shore A, about 30 Shore A to about 35 Shore A, about 30 Shore A to about 40 Shore A, or about 35 Shore A to about 40 Shore A. In some embodiments, the bottom surface of the support 240 has a hardness of about 10 Shore A, about 15 Shore A, about 20 Shore A, about 25 Shore A, about 30 Shore A, about 35 Shore A, or about 40 Shore A. In some embodiments, the bottom surface of the support 240 has a hardness of at least about 10 Shore A, about 15 Shore A, about 20 Shore A, about 25 Shore A, about 30 Shore A, or about 35 Shore A. In some embodiments, the bottom surface of the support 240 has a hardness of at most about 15 Shore A, about 20 Shore A, about 25 Shore A, about 30 Shore A, about 35 Shore A, or about 40 Shore A. In some embodiments, the bottom pad is an elastomeric base. In some embodiments, the bottom pad comprises a length of about 132 millimeters.

In some embodiments, the support 240 of the base 110 is curved. In some embodiments, the patient-contacting surface of the support 240 has a downward concave curvature to conform to one or more vertebrae in flexion. In some embodiments, the radius of downward concave curvature in the longitudinal direction (parallel to the direction of the scanning track) is approximately one meter.

In some embodiments, the patient-contacting surface of the support 240 has an upward concave curvature to conform to the tissue between the thoracolumbar fascia. In some embodiments, the patient-contacting surface of the support 240 has an M-shaped curvature to optimize conformance in the mediolateral direction.

In some embodiments, the support 240 comprises a grip area for the user's non-dominant hand. In some embodiments, the grip area is on the left side of the support 240 when viewed from the front. In some embodiments, the grip area is rounded. In some embodiments the grip area comprises multiple materials. In some embodiments, the grip area comprises an undercut to improve purchase. In some embodiments, the grip area is a removable palm pad that is assembled with the support 240. In some embodiments, removable palm pads are available in different sizes and grips.

A. Carriage

Figure 3A:
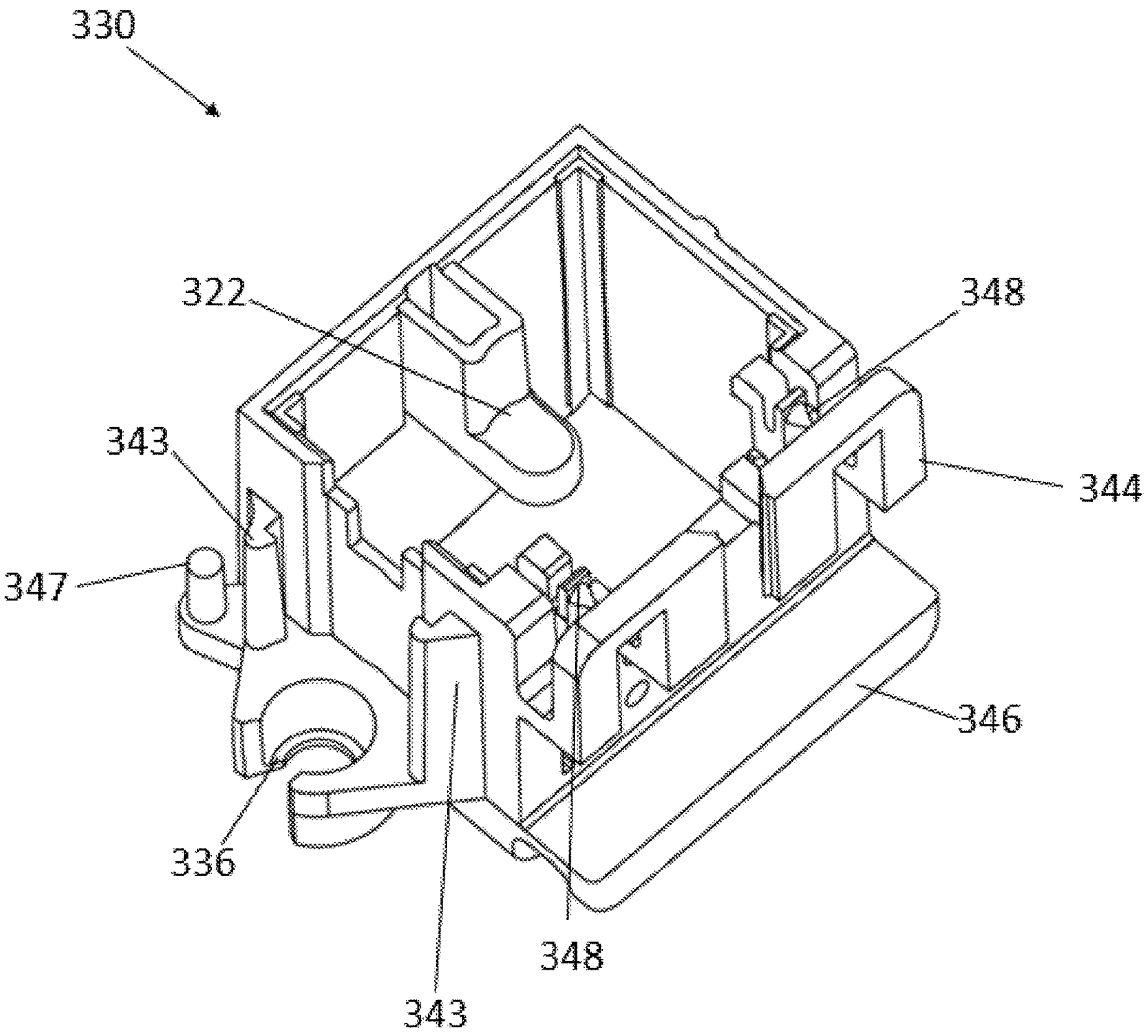
FIG. 3A shows a carriage component of a tactile sensing and guidance system, according to some embodiments.

In some embodiments, the tactile sensing device comprises a carriage 330. With reference to FIG. 3A, an embodiment of the carriage 330 is depicted. In some embodiments, the carriage 330 comprises an alignment guide 336. In some embodiments, the alignment guide is provided on the anterior side of the carriage and is fixed to the carriage. In other embodiments, the alignment guide may be removably attached to the carriage, located on the posterior side of the carriage, and/or located on the side of the carriage opposite of the scanning track. The alignment guide 336 may be configured as a guide for a syringe needle combination. The alignment guide 336 may be configured as a guide to assist in marking a target location with a marking utensil.

In some embodiments, the carriage 330 comprises one or more protrusions 344, 346 to engage with the scanning track. In some embodiments, the protrusions 344 comprise a ledge to engage with an inner surface of the scanning track. In some embodiments, the coupling of the carriage with the scanning track provides a friction force. The frictional force may prevent movement of the carriage relative to the scanning track when the device is operated positioned at an angle. In some embodiments, a force of approximately 0.5 to 0.8 pounds (lbs) is required to move the carriage along the scanning track.

In some embodiments, the carriage 330 comprises one or more locking tabs 348 configured to engage an elastomeric strip and prevent movement of the carriage along the scanning track when the scanhead is being depressed. In some embodiments, the locking tabs 348 are provided with one or more pointed protrusions which engage into the elastomeric strip.

In some embodiments, the carriage 330 further comprises one or more needle guide tabs 343 configured to reversibly receive a needle guide attachment. The carriage may further comprise one or more release gate attachment protrusions 347 to receive a release gate.

In some embodiments, the carriage 330 comprises a spring guide 322 configured to guide a spring which biases the scanhead toward the proximal side of the tactile sensing device. In some embodiments, the spring guide comprises a top surface to contact one end of a spring and a sidewall to help retain the spring. The sidewall and/or top surface of the spring guide 322 may comprise a concave or indented surface to better retain the spring.

B. Scanhead Subassembly

Figure 3B:
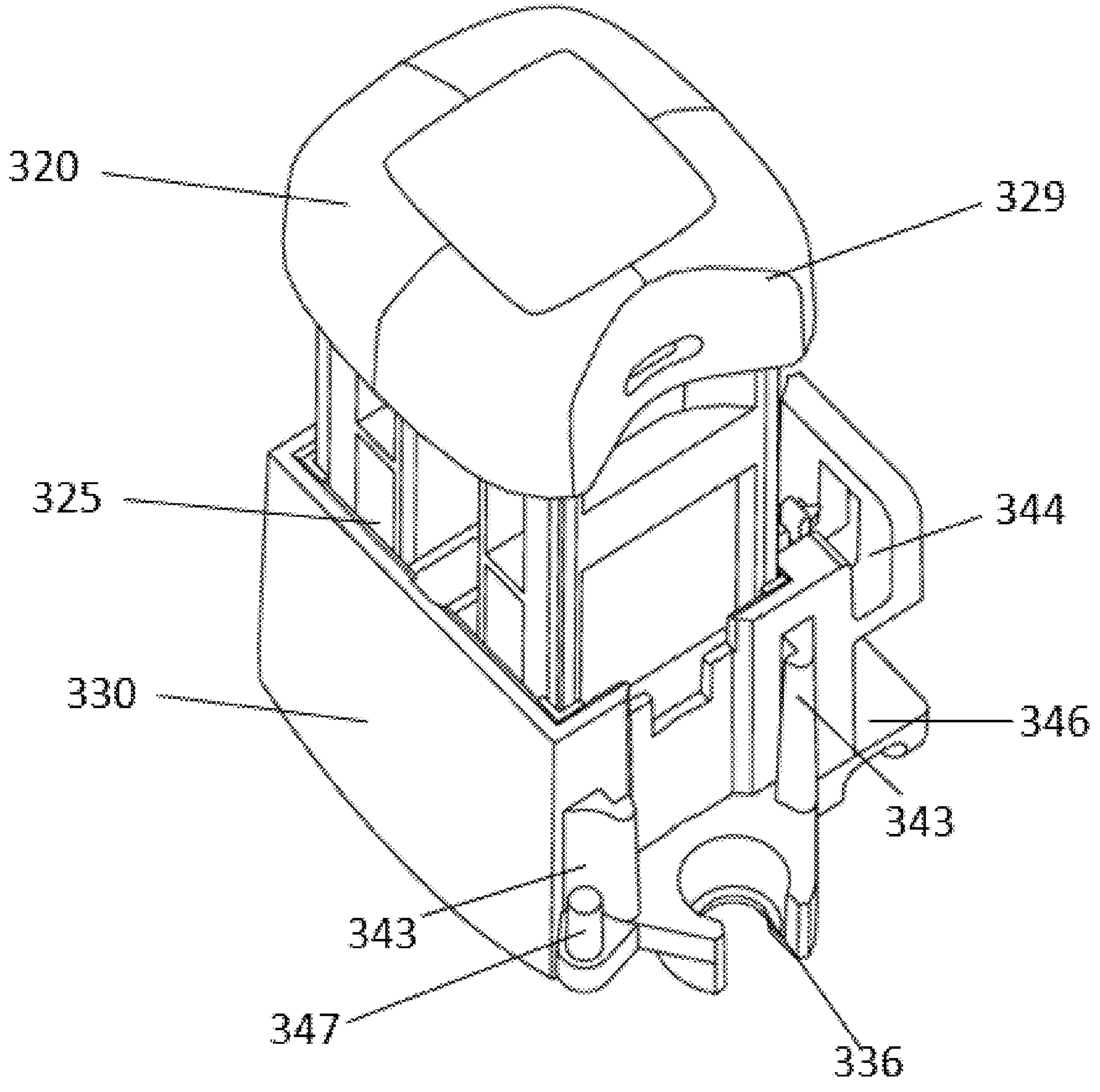
FIG. 3B shows a scanhead subassembly component of a tactile sensing and guidance system, according to some embodiments.

In some embodiments, as depicted in FIG. 3B, the scanhead subassembly comprises a carriage 330 and a scanhead 325. The scanhead subassembly may further comprise a sensor array and a flexible sensor printed circuit board. In some embodiments, the scanhead further comprises a scanning cap or knob 320 having a surface for a user to depress the scanhead into a skin surface of a patient. In some embodiments, the carriage 330 is reversibly secured around one or more sides of the scanhead 325.

According to some embodiments, the scanhead subassembly comprises the body of the scanhead, onto which the sensor and sensor printed circuit board (PCB) are mounted. The length of the scanhead can be adjusted via the integrated spring to allow for up to approximately 2.5 cm of tissue penetration relative to the unloaded position. Additionally, in the resting position, the bottom surface of the scanhead is at an elevated position to provide clearance for scanning.

Figure 3C:
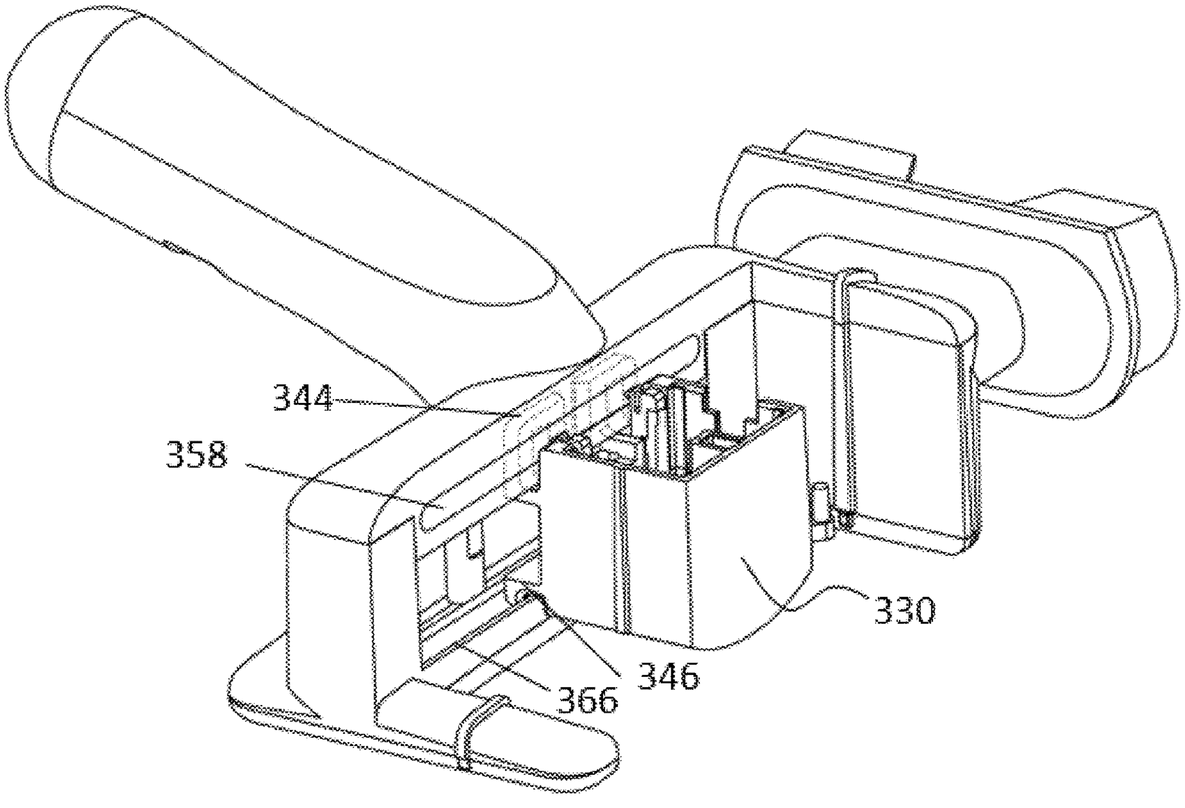
FIG. 3C shows a carriage component coupled to a base component of a tactile sensing and guidance system, according to some embodiments.
Figure 3D:
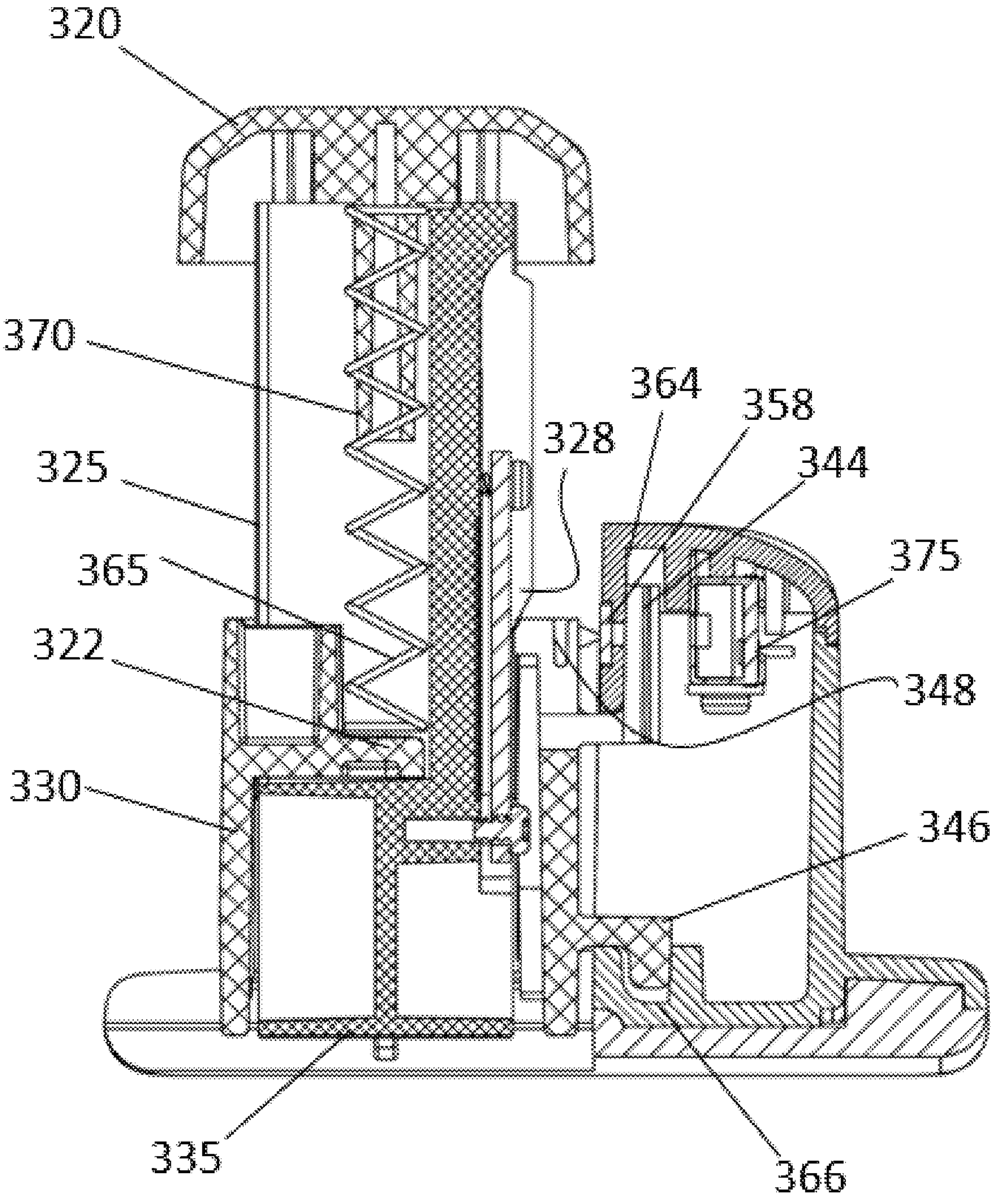
FIG. 3D shows a cross-section view of a scanhead subassembly component coupled to a base component of a tactile sensing and guidance system, according to some embodiments.
Figure 3E:
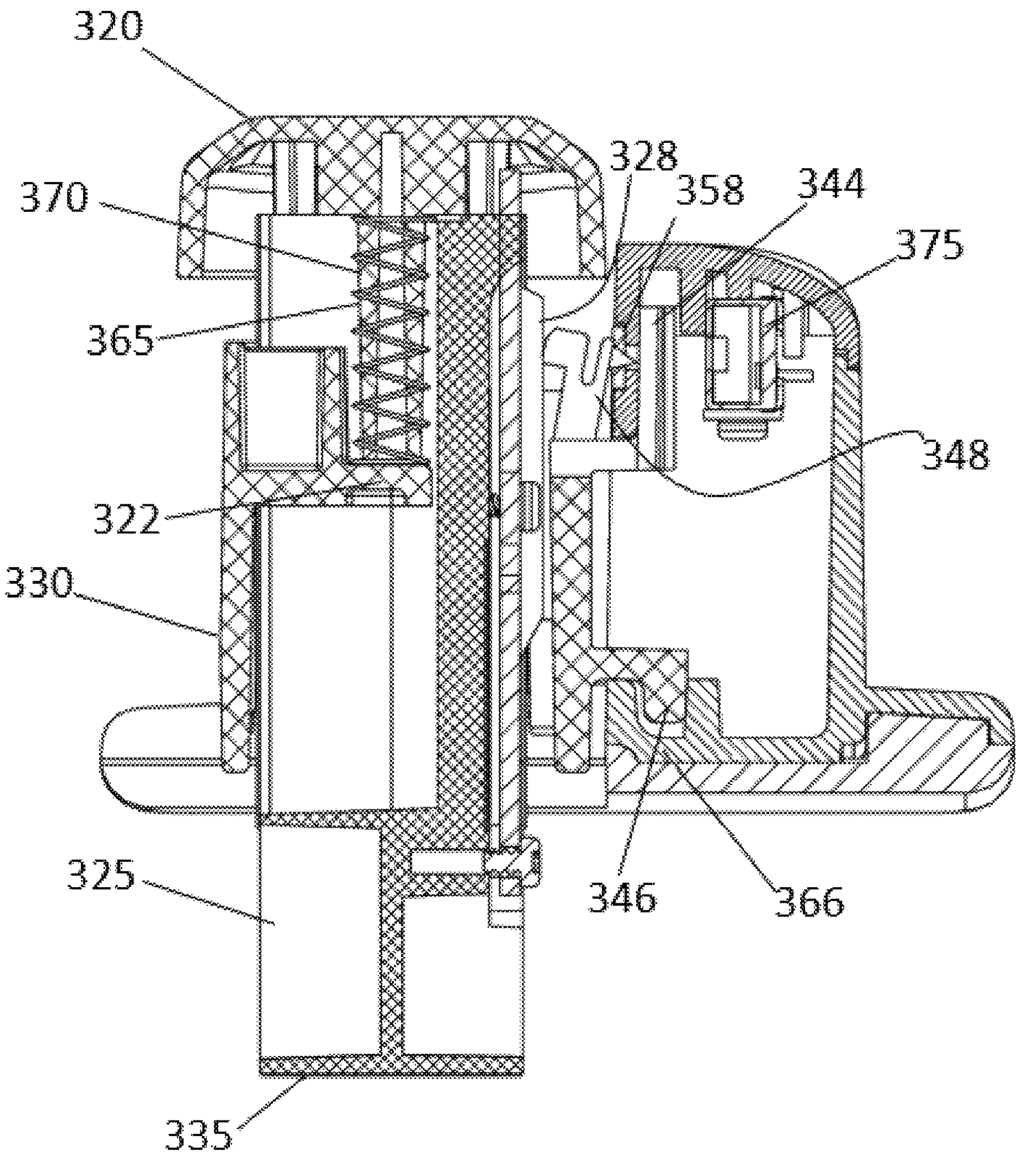
FIG. 3E shows a cross-section view of a scanhead subassembly component coupled to a base component of a tactile sensing and guidance system, according to some embodiments.

With reference to FIG. 3C-3E, in some embodiments, the carriage 330 mates with the scanning track, thereby enabling the scanhead 325 to be translated along the scanning track. In some embodiments, the carriage 330 is inserted into the scanning track and used to traverse a scanhead 325 along the spine. In some embodiments, the carriage is magnetically mated to the track. In some embodiments, mating of the carriage 330 with the scanning track is further bolstered through the use of pre-compressed springs. In some embodiments, silicone or other materials are used on the sliding surface between the carriage 330 and scanning track to provide friction and support mating.

In some embodiments, an upper protrusion 344 of the carriage fits within an upper track 364 of the base. In some embodiments, a lower protrusion 346 of the carriage fits within a lower track 366 of the base. Mating of the upper and lower protrusions with the tracks may allow for stabilization of the carriage 330 while still allowing the carriage to translate along the scanning track.

FIGS. 3D and 3E depict cross-sections of the tactile sensing device, according to some embodiments. According to some embodiments, FIG. 3D depicts a scanhead 325 with no force being applied onto the proximal end (with respect to the user). In contrast, FIG. 3E shows a cut away view of the tactile sensing device while a force is being applied onto the proximal end (with respect to the user), according to some embodiments. In other words, FIG. 3E shows the tactile sensing device as a user presses down onto the scanning knob 320 and depresses the scanhead 325 and attached sensor array 335 (e.g., onto the surface of the skin of a patient), according to some embodiments. In other words, FIG. 3E shows the scanhead subassembly at a lower position or depth along the Z-axis compared to the initial position or depth along the Z-axis of the scanhead subassembly that is shown in FIG. 3D, according to some embodiments. The lower position may be referred to as a depressed position.

In some embodiments, the carriage comprises one or more locking tabs 348 configured to engage an elastomeric strip 358 and prevent movement of the carriage along the scanning track when the scanhead is being depressed. In some embodiments, the locking tabs 348 are provided with one or more pointed protrusions or pintles which engage into the elastomeric strip 358. In some embodiments, the scanhead 325 comprises an angled ledge 328 which engages the locking tabs 348, thereby pushing the pointed protrusions into the elastomeric strip and preventing movement of the carriage and scanhead in an anterior or posterior direction, or a proximal or distal direction (i.e. along the Y-axis shown in FIG. 1) as depicted in FIG. 3E.

In some embodiments, the device comprises a depth lock. In some embodiments, the depth lock allows a position of the scanhead to be locked at a depth relative to the carriage. In some embodiments, the scanning knob comprises a button that is configured to release the scanhead from its locked position relative to the carriage. In some embodiments, the scanning knob comprises a button that is configured to release the carriage from its locked position along the track. In some embodiments, an indicator exists to alert to locking of the scanhead in its position along the track or relative to the carriage. In some embodiments, movement of the scanhead is automated. In some embodiments, movement of the scanhead is non-automated and controlled by a user. In some embodiments, movement of the scanhead is controlled by a user via buttons. In some embodiments, movement in the proximal and distal direction is controlled by a mechanism located at the top of the scanning knob. In some embodiments, movement along the scanning track is controlled by a mechanism located on the side of the scanning knob. In some embodiments, movement along the scanning track is controlled by a user via push buttons.

In some embodiments, the tactile sensing device comprises a position sensor 375 (575 depicted in FIG. 3D). In some embodiments, the position sensor tracks the position of the carriage 330 relative to the scanning track. In some embodiments the position sensor is a magnetic linear encoder, such as, but not limited to a Hall-effect sensor. In some embodiments, the position sensor is a potentiometer, with a wiper contact connected to a linear or rotational shaft, which forms an adjustable voltage divider relative to two end connections, and outputs a resistance proportional to wiper position along the shaft. In some embodiments, a reference voltage is applied across the fixed end connections, and the output voltage is taken from the wiper contact as it moves along the shaft. In some embodiments, the output voltage is inputted to a PCBA in the monitoring device. In some embodiments, the output voltage travels from the position sensor to the PCBA of the monitoring device via a flexible printed circuit board (e.g. flexible PCB 470 as depicted in FIG. 4B).

In some embodiments, the tactile sensing device comprises a computer program that converts the output voltage to a relative wiper position. In some embodiments the position sensor 375 is a slide potentiometer, which is integrated into the base parallel to the scanning track, with the wiper inserted into a cut in the scanhead 325, such that the output voltage is proportional to the position of the scanhead 325 during scanning. In some embodiments, the calculated position is displayed or reflected in the real-time pressure map displayed on the monitoring device and is used to support the construction of a pressure map during the scanning process. In some embodiments, the position sensor is a linear potentiometer with a separate wiper attached to the scanhead 325. In some embodiments, the position sensor is a magnetic linear encoder, with one or more Hall-effect sensors in the frame. In some embodiments, the position sensor is an optical linear encoder. In some embodiments, the position sensor is a time-of-flight sensor.

In some embodiments as further depicted in FIGS. 3D and 3E, the tactile sensing device comprises a position sensor 375. In some embodiments, the position sensor tracks the position of the carriage relative to the scanning track. In some embodiments, the position sensor is a potentiometer, with a wiper contact connected to a linear or rotational shaft, which forms an adjustable voltage divider relative to two end connections, and outputs a resistance proportional to wiper position along the shaft. In some embodiments, a reference voltage is applied across the fixed end connections, and the output voltage is taken from the wiper contact as it moves along the shaft.

In some embodiments, the tactile sensing device comprises a computer program that converts the output voltage to a relative wiper position. In some embodiments the position sensor 375 is a slide potentiometer, which is integrated into the base parallel to the scanning track, with the wiper inserted into a cut in the scanhead 325, such that the output voltage is proportional to the position of the scanhead 325 during scanning. In some embodiments, the calculated position is displayed or reflected in the real-time pressure map displayed on the monitoring device. In some embodiments, the position sensor is a linear potentiometer with a separate wiper attached to the scanhead carriage. In some embodiments, the position sensor is a magnetic linear encoder, with one or more Hall-effect sensors in the frame. In some embodiments, the position sensor is an optical linear encoder. In some embodiments, the position sensor is a time-of-flight sensor.

With further reference to FIGS. 3D and 3E, a spring 365 is placed between the scanhead 325 and the carriage 330. In some embodiments, the carriage 330 comprises a spring guide 322 configured to guide a spring which biases the scanhead toward the proximal side of the tactile sensing device. In some embodiments, the spring 365 is received by a protrusion 370 extending from a surface of the scanhead 325. In some embodiments, the protrusion may extend from a surface of the scanning knob 320. In some embodiments, the depth at which the scanhead 325 travels, relative to the conditions, is determined by the distance between protrusion 370 and guide 322. In some embodiments, travel of the scanhead 325 is limited as the protrusion 370 contacts the guide 322.

In some embodiments, the spring facilitates a range of about 2.5 centimeters (cm) of scanhead depression into the tissue. In some embodiments, the scanhead is depressed by applying downward pressure to the top of the scanhead or scanning knob. In some embodiments, the scanhead is moved along the scanning track by applying anterior or posterior pressure to the scanhead.

C. Sensor Array

Figure 4A:
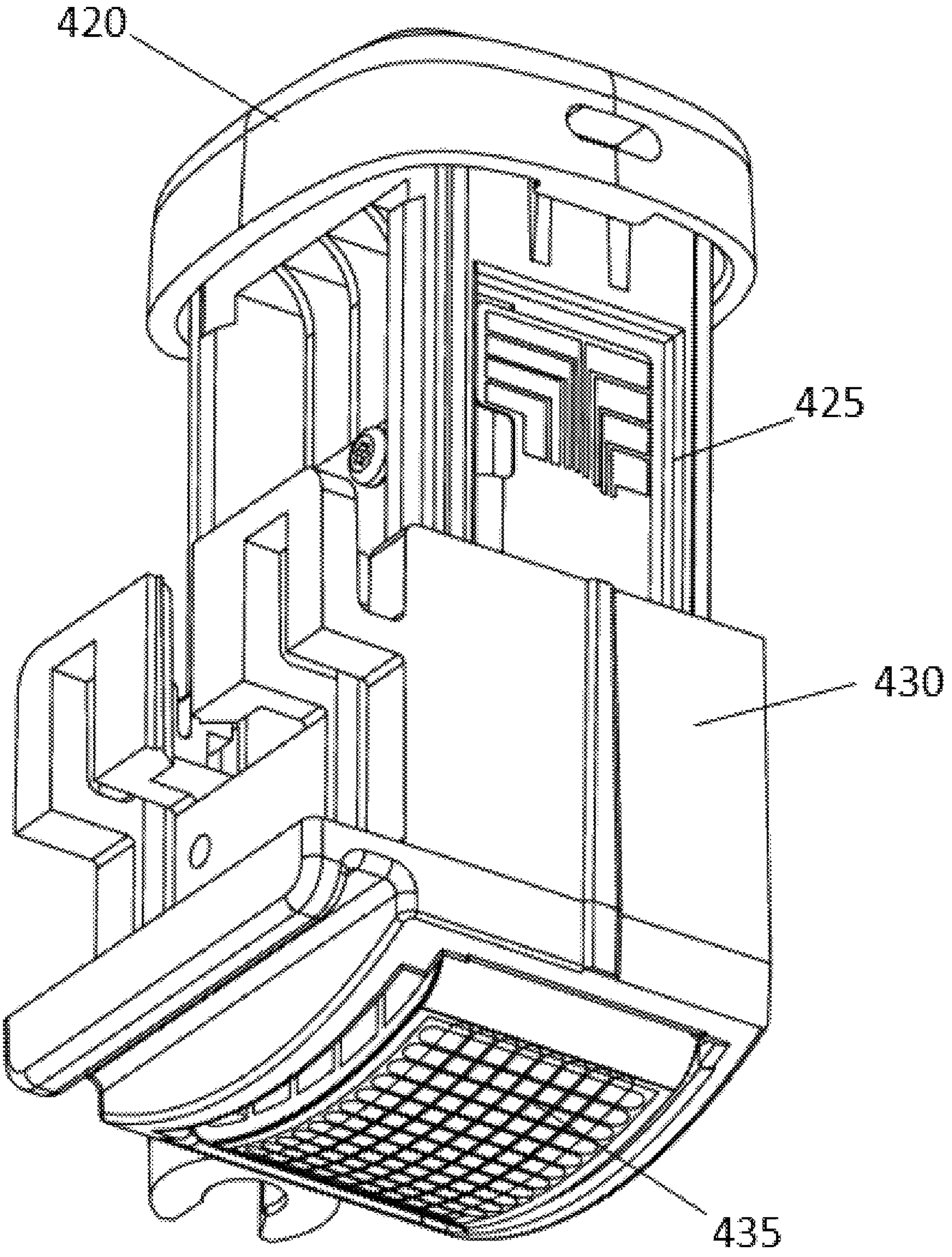
FIG. 4A shows a scanhead subassembly of a tactile sensing and guidance system, according to some embodiments.
Figure 4B:
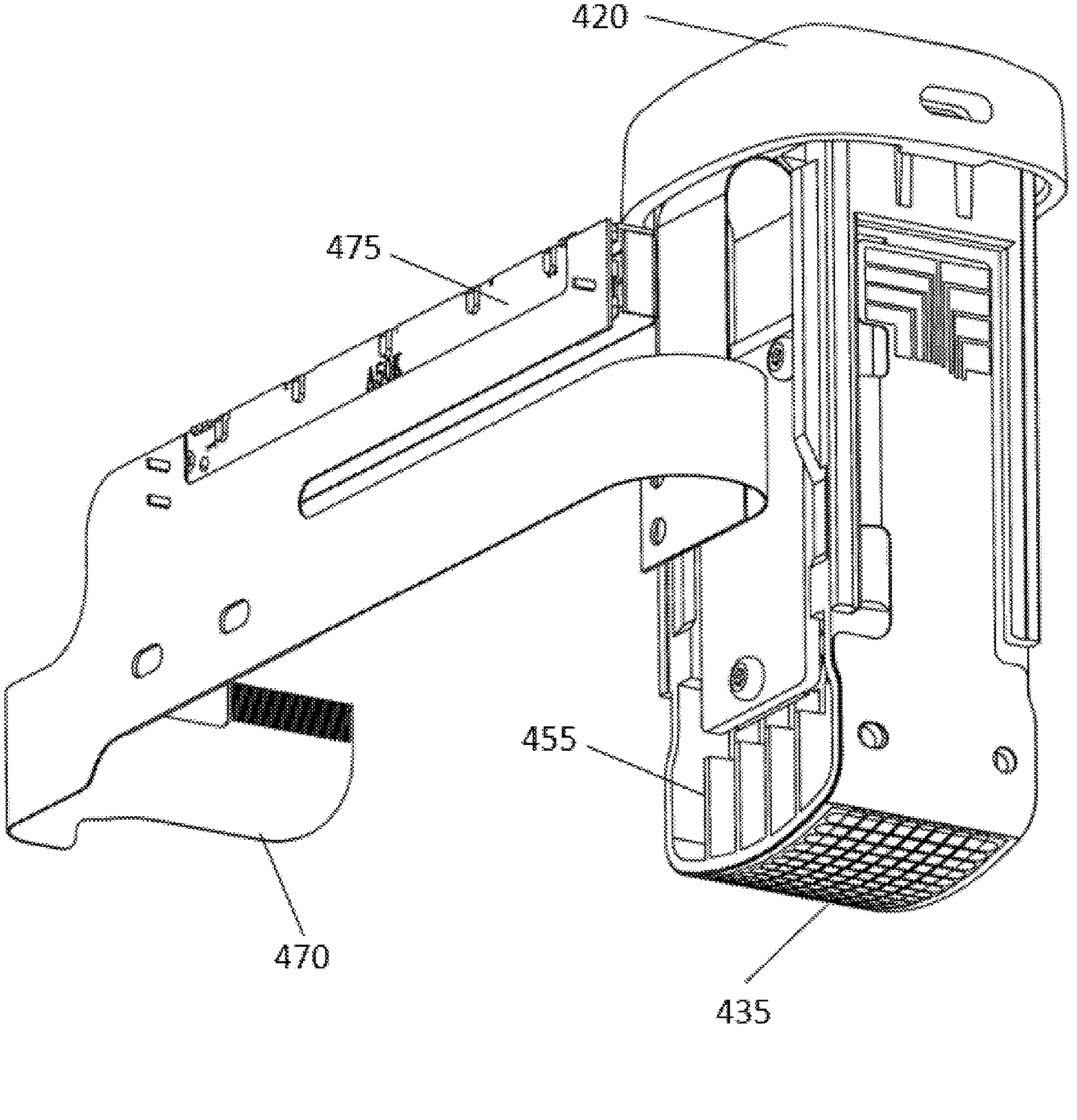
FIG. 4B shows a scanhead component of a tactile sensing and guidance system, according to some embodiments.

FIG. 4A depicts a scanhead subassembly comprising a sensor array 435 provided on a scanhead 425 which is mated with a carriage 430, according to some embodiments. In some embodiments, the anterior and posterior edges of the scanhead are rounded to allow the scanhead to traverse more smoothly along the skin surface. In some embodiments, the anterior and posterior edges of the bottom of the scanhead are filleted with a diameter of about 8 mm, to allow the scanhead to traverse more smoothly along the skin surface. In some embodiments, edge softeners with fillets of about 10 mm in diameter are connected to the anterior and posterior edges of the bottom surface of the scanhead. In some embodiments, the sensor array is mounted to the bottom surface of the scanhead via an adhesive. In some embodiments, the tails of the sensor are tucked into clips on the side of the carriage. In some embodiments, the tails of the sensor are aligned with registration holes on the interior or exterior anterior and posterior faces of the scanhead.

In some embodiments, the user applies a force on or presses down on the scanning knob 420 in order to depress the scanhead relative to the carriage 430. In some embodiments, the user applies a force or presses down on the scanning knob 420 in order to change the position of the scanhead to a lower position or depth.

In some embodiments, the user controls the depth of the scanhead subassembly along the Z-axis by varying the amount of force that she or he applies to the scanning knob 420. In some embodiments, the depth of travel for the scanhead subassembly ranges from about 0 centimeters (cm) to about 10 cm. In some embodiments, the depth of travel of the scanhead subassembly ranges from at least about 0 cm. In some embodiments, the depth of the scanhead subassembly ranges from at most about 10 cm. In some embodiments, the depth of the scanhead subassembly ranges from about 0 cm to about 1 cm, about 0 cm to about 2 cm, about 0 cm to about 3 cm, about 0 cm to about 4 cm, about 0 cm to about 5 cm, about 0 cm to about 6 cm, about 0 cm to about 7 cm, about 0 cm to about 8 cm, about 0 cm to about 9 cm, about 0 cm to about 10 cm, about 1 cm to about 2 cm, about 1 cm to about 3 cm, about 1 cm to about 4 cm, about 1 cm to about 5 cm, about 1 cm to about 6 cm, about 1 cm to about 7 cm, about 1 cm to about 8 cm, about 1 cm to about 9 cm, about 1 cm to about 10 cm, about 2 cm to about 3 cm, about 2 cm to about 4 cm, about 2 cm to about 5 cm, about 2 cm to about 6 cm, about 2 cm to about 7 cm, about 2 cm to about 8 cm, about 2 cm to about 9 cm, about 2 cm to about 10 cm, about 3 cm to about 4 cm, about 3 cm to about 5 cm, about 3 cm to about 6 cm, about 3 cm to about 7 cm, about 3 cm to about 8 cm, about 3 cm to about 9 cm, about 3 cm to about 10 cm, about 4 cm to about 5 cm, about 4 cm to about 6 cm, about 4 cm to about 7 cm, about 4 cm to about 8 cm, about 4 cm to about 9 cm, about 4 cm to about 10 cm, about 5 cm to about 6 cm, about 5 cm to about 7 cm, about 5 cm to about 8 cm, about 5 cm to about 9 cm, about 5 cm to about 10 cm, about 6 cm to about 7 cm, about 6 cm to about 8 cm, about 6 cm to about 9 cm, about 6 cm to about 10 cm, about 7 cm to about 8 cm, about 7 cm to about 9 cm, about 7 cm to about 10 cm, about 8 cm to about 9 cm, about 8 cm to about 10 cm, or about 9 cm to about 10 cm. In some embodiments, the depth 73 of the scanhead subassembly ranges from about 0 cm, about 1 cm, about 2 cm, about 3 cm, about 4 cm, about 5 cm, about 6 cm, about 7 cm, about 8 cm, about 9 cm, or about 10 cm.

In some embodiments the sensor array 435 is a calibrated, custom screen-printed sensor array which allows for pressure sensing. The array may be comprised of two thin, polyester sheets, with conductive silver traces deposited in row and column patterns on the inner surface of each sheet, respectively. Each intersection of the columns and rows forms a sensing element, which acts as a variable resistor, whose resistance varies inversely with applied load. A signal can be routed through a row and into the columns. Current can be measured from a given sensing element through its column by exciting one row and grounding the rest. Current can be converted to a voltage representative of the resistance of the sensing element. Sequential scanning of these sensing elements allows for 2D mapping of the pressure distribution over the vertebrae or other surface which the tactile sensing device is placed on. In some embodiments, spacing between adjacent sensors of the sensors array is measured from the center of a first sensor to the center of an adjacent sensor, or center-to-center spacing. In some embodiments, the center-to-center spacing is about 1.9 mm, which effectively resolves the lowest extreme of observed interspinous spaces. In some embodiments, the censors are calibrated to a mean application pressure of 20 psi, which effectively resolves bony landmarks in obese patients. The array is mounted on the bottom surface of the scanhead via an adhesive layer spanning its active area.

In some embodiments, the bottom surface of the scanhead serves as a platform for a sensor array. In some embodiments, the sensor array has 11 rows and 9 columns of sensors, with a 1.9 mm spacing. In some embodiments, the sensor array has 12 rows and 8 columns of sensors, with 1.9 mm spacing. In some embodiments, the bottom surface of the scanhead is curved. In some embodiments, the bottom surface of the scanhead has a curvature with a radius of about 75 mm opposite that of the vertebrae. In some embodiments, the bottom surface of the scanhead is about 20×16 mm. In some embodiments, the bottom surface of the scanhead is about 30 mm×21 mm. In some embodiments, the active sensing area of the sensor array is about 22 mm (12 rows)×15 mm (8 columns). In some embodiments, the active sensing area of the sensor array is approximately 350 $mm^2$. In some embodiments, the surface area of the sensor array provided on the distal surface of the scanhead is approximately 650 $mm^2$.

FIG. 4B depicts a scanhead subassembly comprising a sensor array 435 provided on a scanhead 425, according to some embodiments. FIG. 4B further depicts a flexible printed circuit board (PCB) 470, according to some embodiments. In some embodiments, as depicted in FIG. 4B, the tactile sensing device further comprises a flex printed circuit board (PCB) 470. In some embodiments, the flex PCB 470 is mounted to the scanhead 425 and connected to the sensor array 435 at a sensor terminal, allowing the sensor to interface with downstream electronics, including the multiplexer circuitry at the interface of the base and the monitor device. In some embodiments the sensor array is connected to the flexible PCB with anisotropic, conductive adhesive. In some embodiments, the flexible PCB allows it to move freely along the y- and z-axes, thereby supporting sliding and pushing of the scanner. FIG. 4B also depicts a position sensor 475, according to some embodiments. In some embodiments, position sensor 475 is a slide potentiometer, which is integrated into the base parallel to the direction which the carriage translates along the scanning track, with the wiper inserted into a cut in the scanhead 425, such that the output voltage is proportional to the position of the scanhead 425 during scanning. In some embodiments, the calculated position is displayed or reflected in the real-time pressure map displayed on the monitoring device and is used to support the construction of a pressure map during the scanning process. In some embodiments, the position sensor is a linear potentiometer with a separate wiper attached to the scanhead 425. In some embodiments, the position sensor is a magnetic linear encoder, with one or more Hall-effect sensors in the frame. In some embodiments, the position sensor is an optical linear encoder. In some embodiments, the position sensor is a time-of-flight sensor.

D. Needle Guide and Restrictor

Figure 5A:
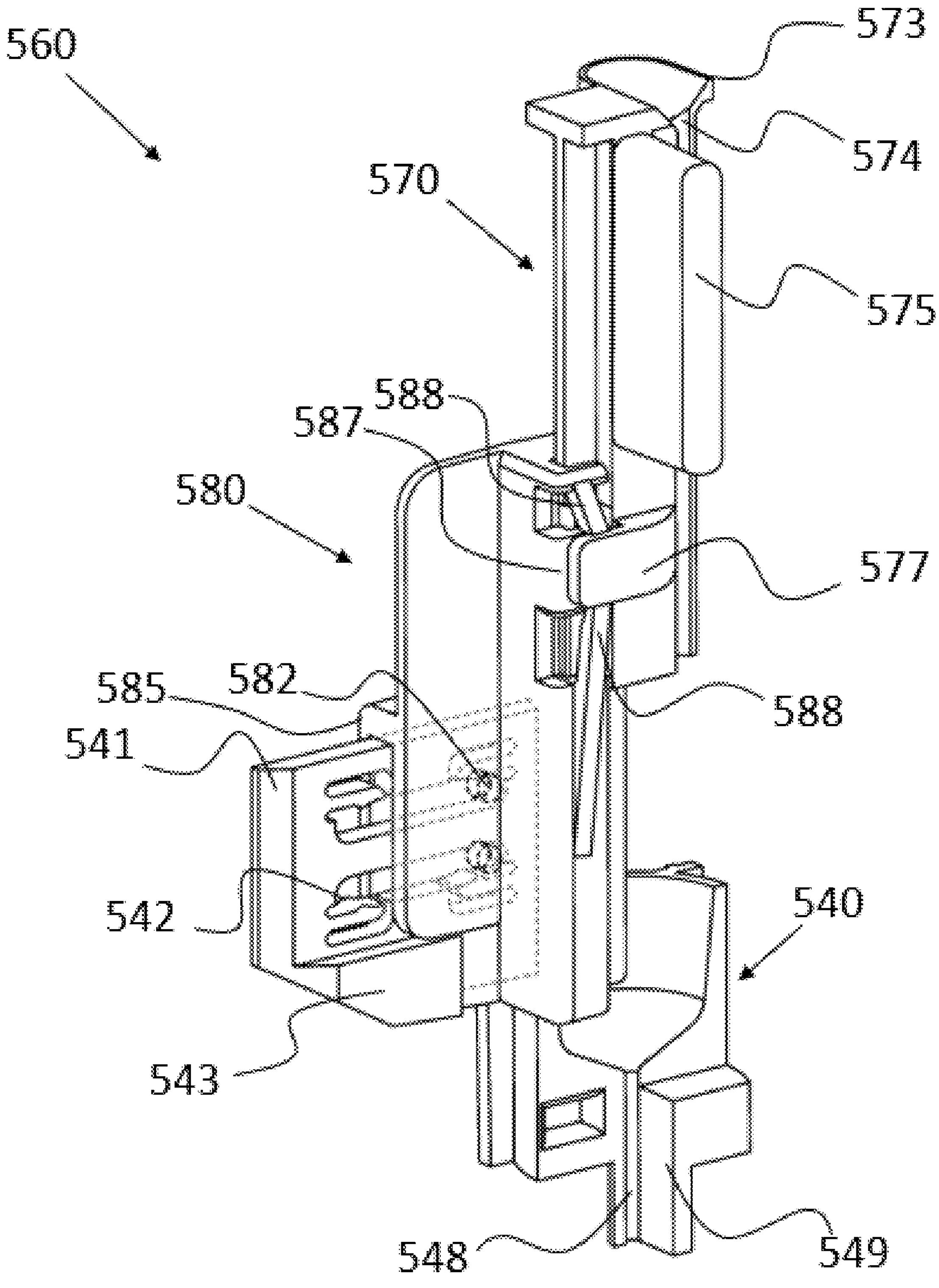
FIG. 5A shows a needle guide subassembly of a tactile sensing and guidance system, according to some embodiments.
Figure 5B:
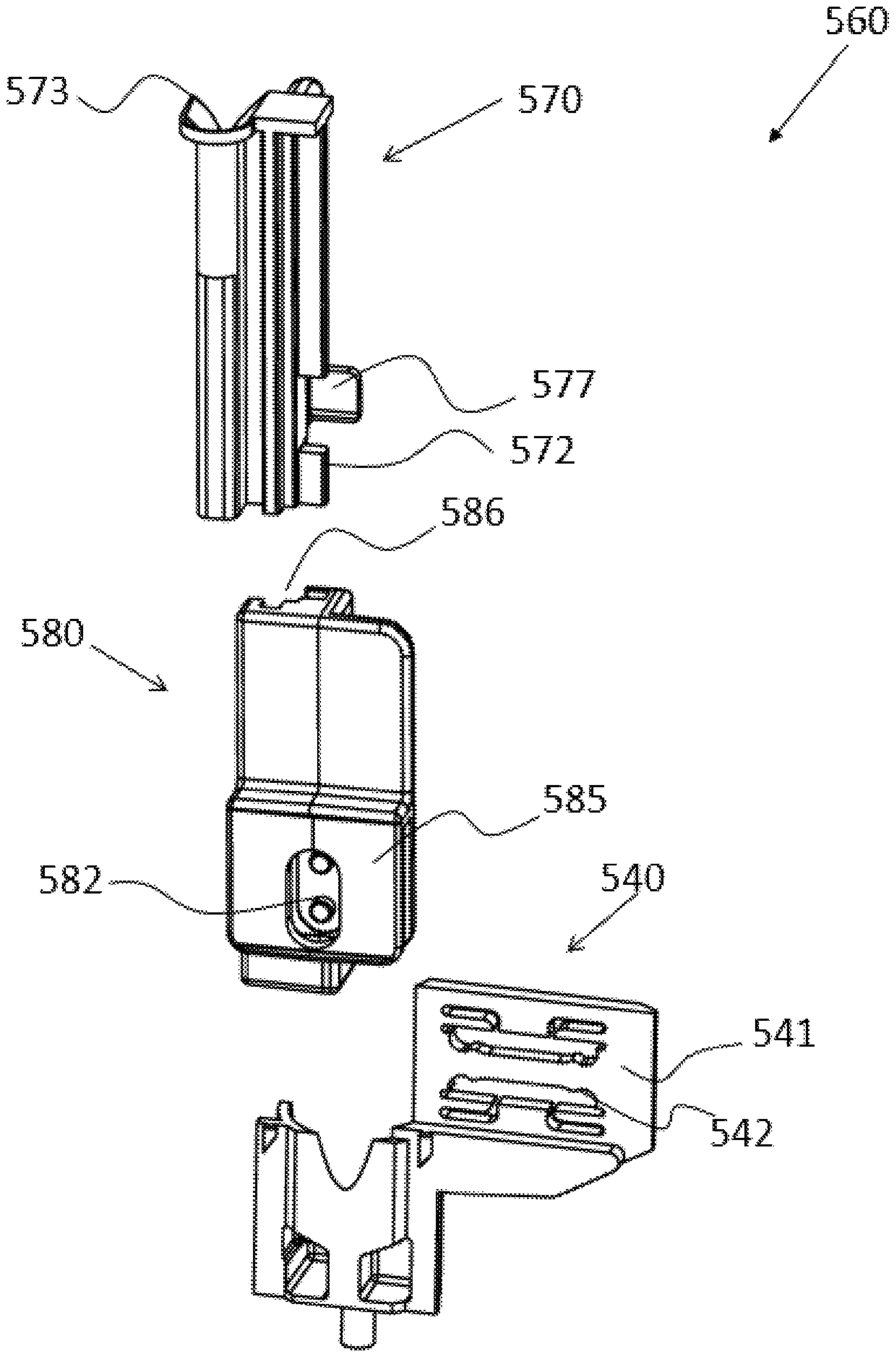
FIG. 5B shows a needle guide subassembly of a tactile sensing and guidance system, according to some embodiments.
Figure 5C:
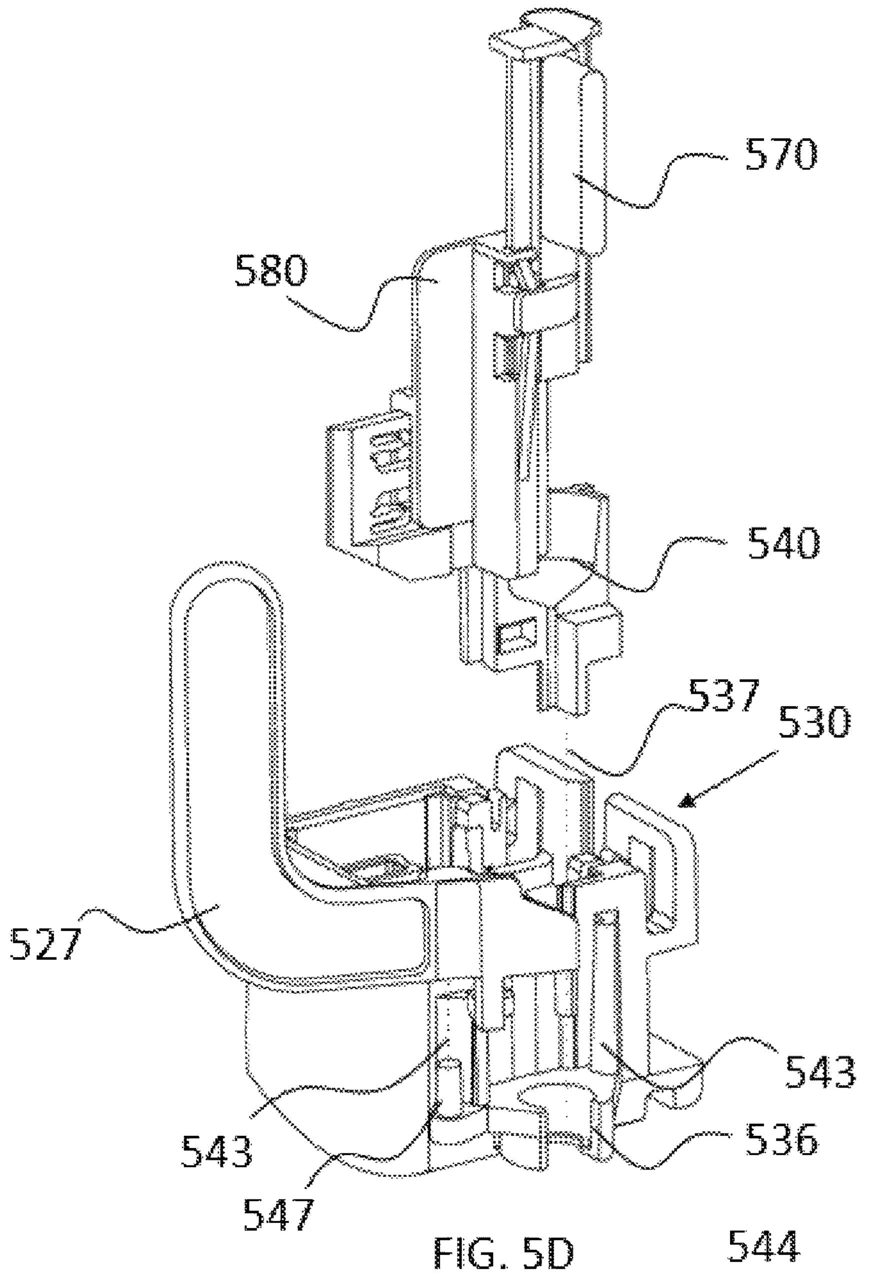
FIG. 5C shows a needle guide subassembly coupled to a carriage component of a tactile sensing and guidance system, according to some embodiments.
Figure 5D:
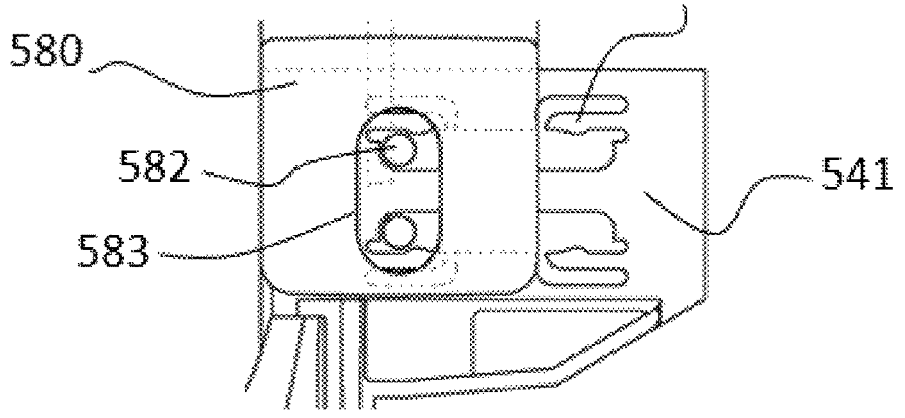
FIG. 5D shows a needle guide subassembly of a tactile sensing and guidance system, according to some embodiments.

FIGS. 5A-5E depict a needle guide and needle depth restrictor subassembly 560 which is removably attachable to the carriage of the tactile sensing device, according to some embodiments. In some embodiments, the needle guide subassembly 560 comprises a needle guide 540, a depth restrictor 570, and a connector 580. In some embodiments, a needle guide 540 is removably attached to the carriage 530. The needle guide may be used as a standalone component without additional components of the needle guide subassembly 560 (as depicted in FIG. 5D). In some embodiments, the needle guide is received by one or more needle guide tabs 543 (also see 343 in FIGS. 3A and 3B), wherein the needle guide is slid onto the carriage and held in place by said needle guide tabs 543.

In some embodiments, a portion of the needle guide 540 is inserted into the alignment guide 536 of the carriage 530. In some embodiments, at least a portion of slot 548 of the needle guide 540 is inserted into the alignment guide 536. In some embodiments, when the needle guide 540 is coupled to the carriage, the needle guide and the alignment guide will share a common center axis 537. In some embodiments, the depth restrictor 570 will also share a common center axis with the alignment guide and/or needle guide. In some embodiments, the needle guide will share a common center axis with the sensor array. In some embodiments, the design is such that a crosshair or target depicted on the monitor will accurately represent the a center axis of the alignment guide and a center axis of the needle guide (when inserted coupled to the carriage), such that the a crosshair displayed on the monitoring device will accurately portray a target site or an insertion when the needle guide or depth restrictor is utilized. In some embodiments, the center of the alignment guide is at a fixed distance from the center of the sensor array. In some embodiments, the center of the alignment guide is located about 24 mm from the center of the sensor array. The alignment guide 536 without the needle guide inserted may act as a marker guide to guide a surgical marker or other marker to mark a target or insertion site on a surface. In some embodiments, the tactile sensing device with the integrated needle guide subassembly does not block more than about 67% of about a 15-mm diameter circle around an identified target site, when viewed from the proximal side.

The needle guide subassembly 560 may be configured such that a depth restrictor 570 can be slid over and into alignment needle guide 540 or moved away from and out of alignment with needle guide 540. In some embodiments, the coupling of the connector plate 541 and connector 580 allows the depth restrictor to be translated about 12 mm laterally. In some embodiments, the needle guide subassembly is configured such that the depth restrictor can be raised or lowered (i.e. raised to a position proximal to a user and lowered to a position distal to a user). In some embodiments, the needle guide component further comprises a connector plate 541. In some embodiments, the connector plate 541 comprises slots 542. In some embodiments, connector 580 comprises protrusions 582 are received by the slots 542 of connector plate 541 of needle guide 540. In some embodiments, connector plate 541 is inserted into a portion of the connector formed by an overhang 585 extending from the connector. The connector plate 541 may comprise one or more protrusions 543 to stabilize the connector 580.

FIG. 5D depicts a detailed view of the coupling of the connector 580 with the connector plate 541 of the needle guide 540. In some embodiments, the slots 542 of the connector plate comprise tabs 544, which lock the protrusions 582 into place at the ends of the slots. In some embodiments, a sufficient force applied by a user may flex the tabs 544 to allow the connector 580 to be translated along the connector plate 541. In some embodiments, the connector comprises an aperture 583. The aperture may provide a grip point for a user. The aperture may allow a user to see that the connector 580 is properly coupled to the connector plate 541. In some embodiments, connector 580 acts as a removal tab.

In some embodiments, the connector plate 541 acts as a removal tab to provide a surface for a user to grip and remove said needle guide 540 from the carriage 530. In some embodiments, the needle guide 540 is configured to retain and guide a needle and syringe combination. In some embodiments, the needle guide is placed within alignment guide 536. In some embodiments, the needle guide 540 comprises a proximal opening 546 that tapers toward the distal end 547 to support a syringe or hub of a needle or introducer. In some embodiments, the taper forms a relatively conical section. In some embodiments, the taper allows a needle to enter the needle guide channel with any initial path of entry. In some embodiments, a slot 548 provides the user with lateral access to the needle guide, allowing a user to remove the tactile sensing device while a needle is placed in the skin surface of a patient. In some embodiments, the slot 548 is about 1 mm wide (i.e. about 1 mm in diameter). In some embodiments, a block 549 helps guide a needle into and out of the slot 548. In some embodiments, the proximal ends of the needle guide are chamfered to facilitate insertion of a needle into the slot 548.

In some embodiments, the needle guide assembly comprises a depth restrictor 570. In some embodiments, the depth restrictor comprises one or more protrusions 572 configured to be received by slots 586 provided in the connector 580. Depth restrictor 570 may couple with the connector 580 such the depth restrictor may be raised or lowered relative to the skin surface when the device is placed on a patient. In some embodiments, the depth restrictor comprises a locking protrusion 577, which locks into a recess 587 in the connector 580 to lock the restrictor in an upper position. In some embodiments, the depth restrictor comprises an upper position and a lower position. In some embodiments, release tabs 588 are depressed to release the restrictor from a locked position. In some embodiments, the depth restrictor 570 comprises a proximal opening 573 that tapers toward the distal end to support the hub of a needle.

In some embodiments, the depth restrictor 570 limits an insertion depth of a needle to a depth at which it is shallower than the interspinous ligament. In some embodiments, the restrictor element allows for an insertion depth at which the needle will remain secure in the tissue when the device is removed from it. In some embodiments, the restrictor element allows for insertion to a depth of approximately 2 cm. In some embodiments, the restrictor element allows for an insertion depth up to approximately 0.5 cm to 5 cm. In some embodiments, the upper position is utilized for insertion of a 5 inch needle. In some embodiments, the depth restrictor limits the insertion depth of a 5 inch needle from about 2 cm to about 5 cm. In some embodiments, the lower position is utilized for insertion of a 3.5 inch needle. In some embodiments, the depth restrictor limits the insertion depth of a 3.5 inch needle from about 2 cm to about 3.5 cm. In some embodiments, the depth restrictor limits the insertion depth of a needle to about a third of the length of the needle shaft. In some embodiments, the depth restrictor is held in place with frictional force and the height of the depth restrictor can be set various positions between the upper and lower positions. In some embodiments, the restrictor comprises ruled markings such that a user can measure a height of the restrictor from the bottom surface of the tactile sensing device or surface being scanned. Ruled markings may also allow a user to set an insertion depth of a needle. In some embodiments, adjustment of the restrictor height is automated.

In some embodiments, the depth restrictor comprises a proximal opening 573 that tapers toward the distal end 574 to support a hub of a needle. In some embodiments, an introducer is placed directly through the needle guide without use of the depth restrictor. In some embodiments, the needle guide limits the insertion depth of the introducer to about 1 cm. In some embodiments, the depth restrictor comprises a grip tab 575 to provide a user with a point to grip the depth restrictor and adjust the height or position relative to the needle guide. In some embodiments, connector 580 acts as a removal tab.

FIG. 5C-5H also depict a needle release gate 527, according to some embodiments and as further described herein. In some embodiments, release gate 527 is received by a release gate attachment protrusion 547 of the carriage 530.

Figure 5E:
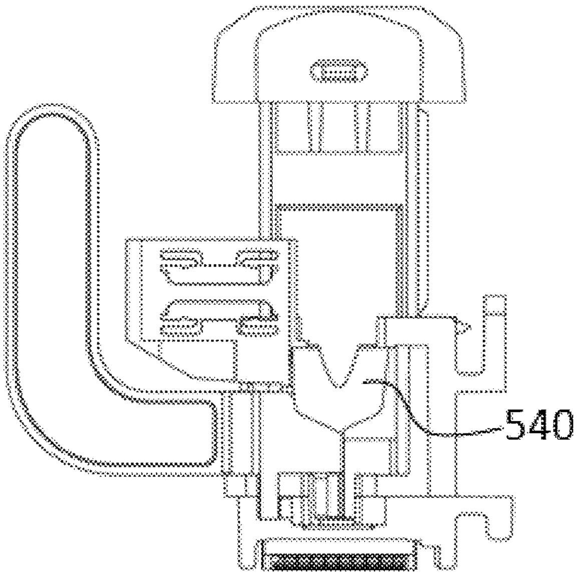
FIG. 5E shows a needle guide component coupled to a carriage component of a tactile sensing and guidance system, according to some embodiments.
Figure 5F:
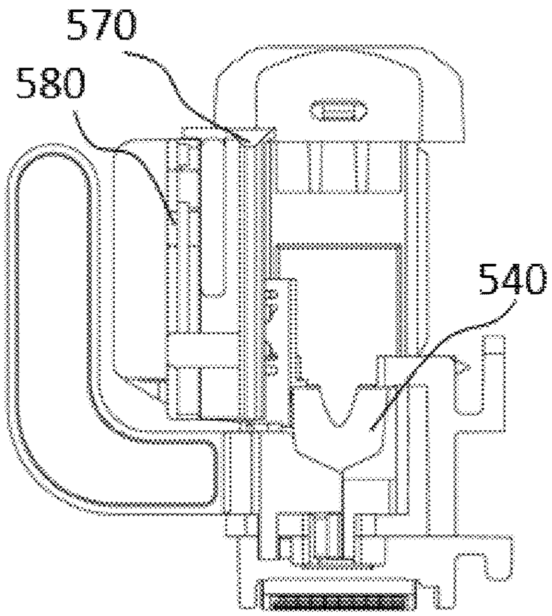
FIG. 5F shows a needle guide subassembly coupled to a carriage component of a tactile sensing and guidance system, according to some embodiments.
Figure 5G:
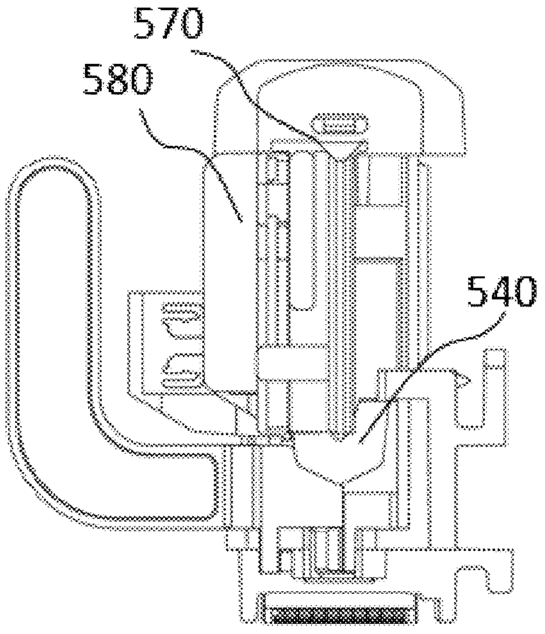
FIG. 5G shows a needle guide subassembly coupled to a carriage component of a tactile sensing and guidance system, according to some embodiments.
Figure 5H:
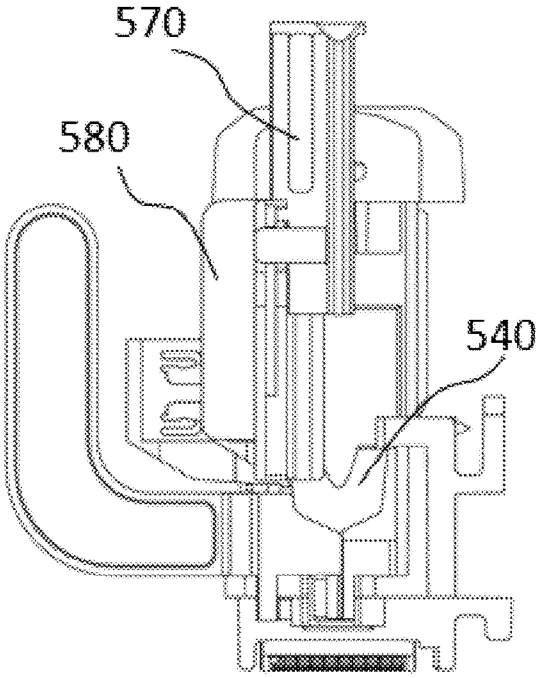
FIG. 5H shows a needle guide subassembly coupled to a carriage component of a tactile sensing and guidance system, according to some embodiments.

FIGS. 5E-5H depict different configurations or positions of the needle guide subassembly, according to some embodiments. As shown in FIG. 5E, the needle guide 540 may be received by the carriage without other components of the needle guide subassembly. As shown in FIG. 5F, the depth restrictor 570 may be provided at a lower positioned and moved out of alignment with the needle guide 540, allowing for access to the needle guide. As shown in FIG. 5G, the coupling between the connector 580 and the needle guide 540 allows for the depth restrictor 570 to be aligned with the needle guide. FIG. 5G depicts the depth restrictor at a lower position, according to some embodiments. In some embodiments, the lower position is utilized to accommodate a 3.5 inch needle. FIG. 5H depicts the depth restrictor 570 aligned with the needle guide 570 and at an upper position, according to some embodiments. In some embodiments, the upper position is utilized to accommodate a 5 inch needle.

In some embodiments, the needle guide has a fixed angle. In some embodiments, the needle guide is oriented perpendicular to the patient (i.e. parallel to z-axis). In some embodiments, the needle guide has an adjustable angle. In some embodiments, the needle guide has one or more tracks appropriate for insertion of one or more types of needles. In some embodiments, the track of the needle guide has a fixed diameter. In some embodiments, the track of the needle guide has a length of approximately 12 mm. In some embodiments, the distal end of the needle guide is located approximately 8 mm from the lowest surface of the base to allow for visualization of the point of insertion.

In some embodiments, the needle guide is located anterior or posterior to the scanhead. In some embodiments, the needle guide is laterally offset from the scanhead during scanning. In some embodiments, the needle guide is fixed to the carriage. In some embodiments, the needle guide is fixed to the scanhead. In some embodiments, the needle guide is attachable. In some embodiments, once a target tissue location is identified, the scanhead and carriage are manually moved along the scanning track until the alignment guide is positioned at the target tissue location. In some embodiments, once a target tissue location is identified, the scanhead and carriage are automatically moved along the sliding track until the needle guide aligns with the target tissue location. In some embodiments, once a target tissue location is identified, the scanhead and carriage are removed, and the needle guide is attached to the device so as to align with the target tissue location. In some embodiments, the release gate and slot in the needle guide enable the device to be pulled away from the needle or introducer after insertion. In some embodiments, the needle is inserted at a location that is anterior to the scanhead 325. In some embodiments, the needle is inserted at a location that is posterior to the scanhead.

FIG. 6A depicts a scanhead subassembly with release gate 627 and needle guide subassembly 660 comprising a needle guide, connector, and a depth restrictor, according to some embodiments. In some embodiments, the scanning knob 620 comprises a cutout 629 (also see 329 as depicted in FIG. 3B) to allow clearance between a syringe and the scanning subassembly.

In FIG. 6A, the depth restrictor is shown as being out of alignment with the needle guide, according to some embodiments. This configuration may allow a needle to be placed directly into the needle guide when the depth restrictor is translated out of alignment with the needle guide. In FIG. 6B, the depth restrictor is shown as being in alignment with the needle guide, according to some embodiments. In some embodiments, when the depth restrictor is in alignment with the needle guide, the needle guide and the depth restrictor will share a common center axis.

FIGS. 6B and 6C depict embodiments comprising a needle release gate 627 removably attached to the carriage. In some embodiments, release gate 627 is received by a release gate attachment protrusion (347 in FIGS. 3A-B). In some embodiments, the release gate attachment 627 is retained by the protrusion using a friction fit. In some embodiments, a force of about 0.2 to 0.25 pound force (lbf) is required to open the release gate.

FIG. 6B depicts some embodiments comprising the needle release gate 627 in a locked position, while FIG. 6C depicts an embodiment of the needle release gate 627 in an unlocked position. In a locked position, the needle release gate may prevent removal of a syringe and needle combination engaged with the needle guide. In some embodiments, the release gate closes off the slot 648, creating a complete circumference formed by the needle guide's track and the release gate to secure the needle into the needle guide. In some embodiments, the release gate 627 is secured in a locked position by an interference fit with an outside surface of a needle guide tab.

E. Scanning Knob

In some embodiments, the scanning knob is designed to facilitate sliding (via force applied along the Y-axis) and pushing (via force applied along the Z-axis) of the scanhead and sensor to support the scanning process. In some embodiments, a force of about 0.5 to 0.8 pounds is required to slide the scanhead. In some embodiments, the spring is installed on the inner surface of the knob, which supports depression of the scanhead relative to the carriage.

In some embodiments, the scanning knob is configured to incorporate one or more restriction features that can restrict the insertion depths achievable with 3.5 and 5" needles, thereby ensuring that the device must be removed from these needles prior to inserting them into critical structures. In some embodiments, the restriction elements comprise a slot to allow a needle to pass beyond the restriction element while stopping the hub of the needle to restrict the insertion depth. In some embodiments, the restriction elements are configured to receive a hub of a needle and syringe combination. In some embodiments, the restriction element allows for insertion up to approximately 0.5 cm to 4 cm. In some embodiments, the allowed depth of insertion is dependent on the length of the needle. In some embodiments, the allowed depth of insertion is adjustable. In some embodiment, the scanning knob is rotatable relative to the scanhead. A user may rotate the scanning knob to select a restriction element to align with the alignment guide (See 336 in FIG. 3A) which may be fixed or attached to the carriage. In some embodiments, the restriction elements are fixed or removably attached to other components of the scanhead subassembly.

In some embodiments, a restrictor element on a lower portion of the scanning knob is provided to restrict needles of shorter lengths compared to a restrictor element on an upper portion of the scanning knob. In some embodiments, a lower restrictor element is configured restrict the insertion depth of a 3.5 inch needle. In some embodiments, an upper restrictor element is configured to restrict the insertion depth of a 5 inch needle. In some embodiments, one side of the scanning knob is provided with cutouts such that a clearance is provided between the scanning knob and the needle and syringe combination as to not restrict the insertion depth of the needle and syringe combination.

In some embodiments, the scanning knob is removable. In some embodiments, the scanning knob is fixed. In some embodiments, the scanning knob is part of the scanhead. In some assemblies, the scanning knob is attached to the top surface of the scanhead. In some embodiments, the scanning knob is a convex scanning knob. In some embodiments, the convex scanning knob is a scanning knob comprising a proximal surface (with respect to the user) that is curved like the exterior of a circle and/or a sphere. In some embodiments, the concave scanning knob comprises ribs. In some embodiments, the concave scanning knob does not comprise ribs. In some embodiments, the scanning knob is used to move the scanhead and carriage along the scanning track. In some embodiments, the scanning knob is used to move the scanhead proximally and distally (i.e. toward and away from the patient, respectively) relative to the carriage. In some embodiments, the travel of the scanhead along the scanning track, and proximal and distal movement are controlled by the same mechanism. In some embodiments, the travel of the scanhead along the track and the travel of the scanhead relative to the carriage are controlled by independent mechanisms. In some embodiments, movement relative to the carriage prevents movement along the track. In some embodiments, a pintle is used to lock the position of the carriage and scanhead during proximal and distal movement of the scanhead. In some embodiments, the scanning knob comprises a button that is configured to release the scanhead from its locked position relative to the carriage. In some embodiments, the scanning knob comprises a button that is configured to release the carriage from its locked position along the track. In some embodiments, an indicator exists to alert to locking of the scanhead in its position along the track or relative to the carriage. In some embodiments, movement of the scanhead is automated. In some embodiments, movement of the scanhead is non-automated and controlled by a user. In some embodiments, movement of the scanhead is controlled by a user via buttons. In some embodiments, movement in the proximal and distal direction is controlled by a mechanism located at the top of the scanning knob. In some embodiments, movement along the scanning track is controlled by a mechanism located on the side of the scanning knob. In some embodiments, movement along the scanning track is controlled by a user via push buttons. In some embodiments, the scanning knob is pushed proximally and distally to allow for travel relative to the carriage. In some embodiments, the scanning knob is pushed anteriorly and posteriorly to allow for travel along the scanning track. In some embodiments, the scanning knob has a rotary dial that is rotated to move the carriage along the scanning track. In some embodiments, the scanning knob has a rotary dial that is rotated to move the scanhead proximally and distally relative to the carriage. In some embodiments, the scanhead is moved relative to the carriage via a mechanical actuator. In some embodiments, the scanhead is automatically moved relative to the carriage to a level dictated by patient characteristics, such as body mass index (BMI). In some embodiments, the tactile sensing device comprises a mechanism that locks movement along the track and relative to the carriage. In some embodiments, partial images of captured areas are displayed while the scanning cycle is being completed. In some embodiments, areas currently being acquired are highlighted for clarity. In some embodiments, the scanning process of the slider workflow is most similar to the manual palpation-landmarking process. In some embodiments, at least one button is included to detach the scanning knob. In some embodiments, the carriage is fixed upon disengagement of the scanning knob.

F. Alternative Needle Guides

Alternative needle guide and depth restriction components may be utilized. In some embodiments, an outer surface of the carriage comprises the needle guide. In some embodiments the outer surface of the carriage comprises an elongated c-shape opening. In some embodiments, the outer surface of the carriage has a height suitable to restrict the depth of insertion for one needle length. In some embodiments, a depth restriction clip is removably attached to the carriage. In some embodiments, the depth restriction clip comprises one or more protrusions which are received by apertures through an outer surface of the carriage to facilitate attachment. In some embodiments, the depth restriction clip is configured to be adjusted to restrict the depth of insertion for needles of different lengths. In some embodiments, the top of the clip may be raised above the upper edge of the carriage to accommodate a needle having of a greater length. In some embodiments, the depth restriction clip may be reversibly attached at an aperture closer to an upper edge of the carriage to restrict a needle having a greater length. In some embodiments, the top of the clip forms a platform that prevents the hub or handle of a needle from being further distal advancement. In some embodiments, the depth restriction clip may comprise a slot that is concentric with the c-shaped slot of the needle guide. In some embodiments, the depth restriction clip may be reversibly attached at an aperture closer to an upper edge of the carriage to restrict a needle having a greater length. In some embodiments, the depth restriction clip may be rotatable about the Z-axis relative to the outer surface of the carriage. In some embodiments the depth restriction clip may be part of a sliding mechanism along the X-axis relative to the outer surface of the carriage.

In some embodiments, a needle release clip is removably attached to the carriage. In some embodiments, the needle release clip is rotatable, such that it may be rotated against the carriage to confine a needle within to outer surface of the carriage.

In some embodiments, the needle release clip is also configured as a needle guide. A syringe and needle combination may then be inserted into said needle guide, and the needle guide may be rotated to secure a needle provided in the depth restriction clip. In some embodiments, the needle release clip is provided with a tab to facilitate rotation by a user. In some embodiments, the needle release clip configured as a needle guide is configured to hold a syringe and needle combination for injecting a local anesthetic to a target tissue location of a patient in need thereof.

In some embodiments, the depth restriction clip and needle release clip are removably attached to a posterior side of the carriage. In some embodiments, the depth restriction clip and needle release clip are removably attached to an anterior side of the carriage. The depth restriction clip and needle release clip may be removably attached to any outer wall of the carriage.

In some embodiments, the depth restriction clip and needle release clip are fixed to a posterior side of the carriage. In some embodiments, the depth restriction clip and needle release clip are fixed to an anterior side of the carriage. The depth restriction clip and needle release clip may be fixed to any outer wall of the carriage.

G. Monitoring Unit

In some embodiments, the tactile sensing device comprises a detachable monitoring device. In some embodiments, the monitoring device is part of the base. In some embodiments the monitoring device is comprised of a two-part housing. In some embodiments the monitoring device has a back plate for access to electronics. In some embodiments, the monitoring device is assembled with the base. In some embodiments, the monitoring device is a non-sterile, non-patient-contacting part, to be made of medical-grade, injection-molded plastic. In some embodiments, the distal surface of the monitoring unit is raised approximately 12.5 mm relative to the patient-contacting surface of the device.

With reference to FIG. 1, in some embodiments, the monitoring device 150 is provided with one or more depressible user-input buttons 155, 157 which are engageable by a user. In some embodiments, the monitoring device comprises a reset button 155, which resets the pressure map to be displayed by the monitoring device. In some embodiments the monitoring device, comprises one or more buttons 157 located on the side of the monitoring device. Buttons 155, 157 may be configured to adjust setting of the monitoring device. In some embodiments, sensitivity is adjusted via a dial or external buttons 157. In some embodiments, the monitor 150 may be placed in a protective sleeve 180. The protective sleeve may prevent the monitor for becoming damaged or contaminated. The protective sleeve may prevent an non-sterile monitor from contaminated a sterile field.

Figure 7A:
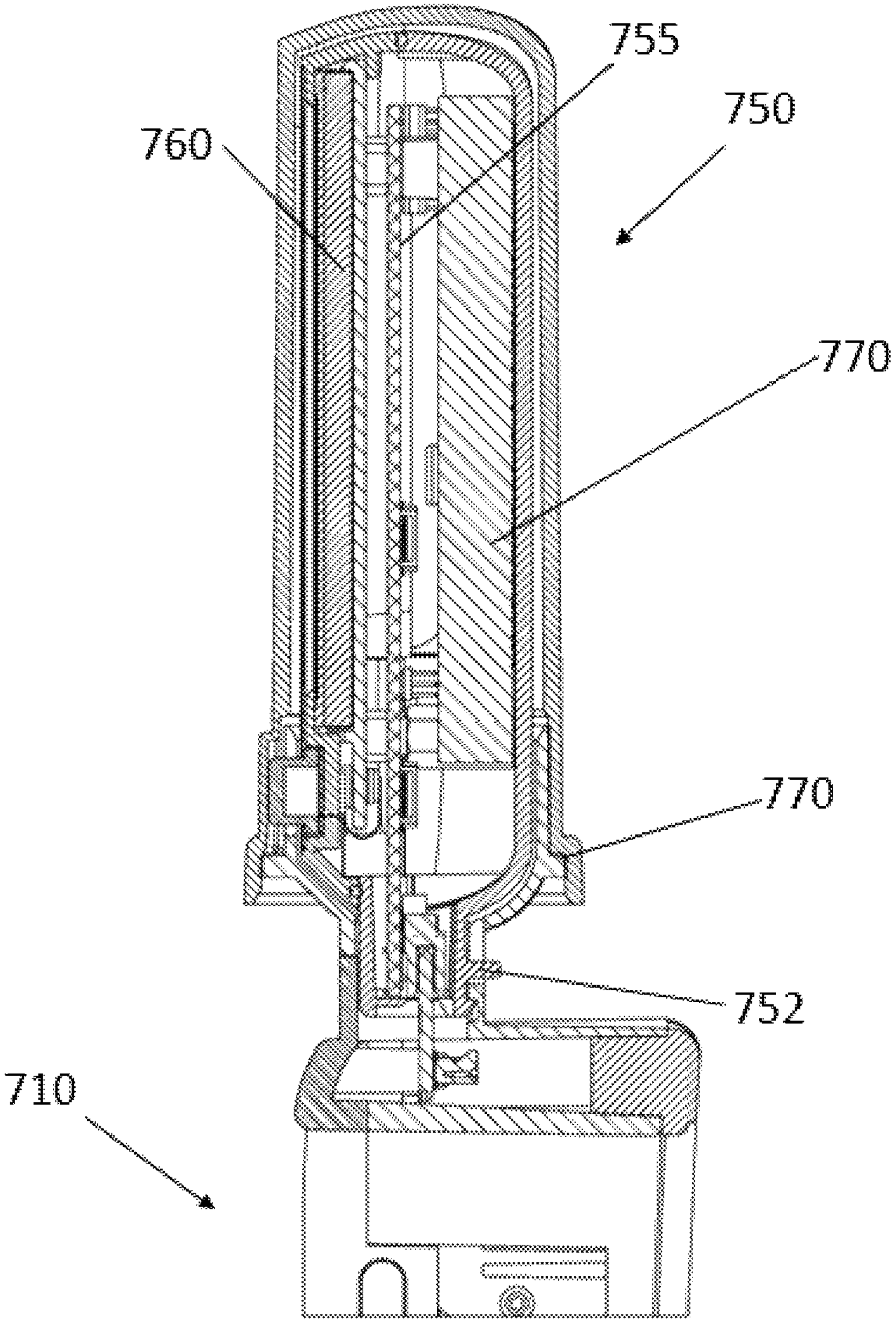
FIG. 7A shows a cross-section view a monitoring device component of a tactile sensing and guidance system, according to some embodiments.

In some embodiments, the base comprises hubs for monitoring device attachment at the top and bottom when the device is viewed from the top to facilitate use in right- and left-handed users. With reference to FIG. 7A, some embodiments of the tactile sensing device comprise a locking mechanism 752 to lock the monitoring device 750 onto the base 110. In some embodiments, the locking mechanism 752 is provided with a tab to facilitate locking of the monitoring device 150 onto the base 710. In some embodiments, the locking mechanism 752 is provided with a tab to facilitate removal of the monitoring device 750 from the base 710. In some embodiments, the monitoring device is placed in a protective sleeve 780, as disclosed herein. In some embodiments, the protective sleeve overlaps a portion of the base 710 and creates a seal around the monitoring device 750.

With reference to FIG. 7A, in some embodiments, the monitoring device 750 comprises a printed circuit board assembly (PCBA) 755. In some embodiments, the PCBA serves as the motherboard of the system of the tactile sensing device. In some embodiments, the PCBA comprises a microprocessor. In some embodiments, the PCBA interfaces to the sensor breakout board, display module, external sensors, and user-input mechanisms. In some embodiments, the PCBA comprises the fusing, charging, and protection circuitry for the rechargeable battery. In some embodiments, the PCBA processes and displays pressure sensor data. In some embodiments, the PCBA processes position sensor data. In some embodiments, the PCBA handles interrupts, such as a physical or touchscreen menu button press and physical or touchscreen refresh button press. In some embodiments, a sample runtime task for live imaging (about 10 milliseconds (ms)) comprises data capture, data analysis, error checks, frame drawing, and frame display. In some embodiments, the PCBA comprises circuitry to support adjustment of maximum sensor pressure between a factor of about 0.14 to a factor of about 3 of the sensor's pressure rating. In some embodiments, sensitivity is adjusted via a dial or external buttons, or a touchscreen display. In some embodiments drive voltage is automatically adjusted based on an equilibration file. In some embodiments, the PCBA comprises sensors and circuitry to track device orientation and trigger alerts to device movement during rocking. In some embodiments, the monitoring device is powered on by a switch. In some embodiments the monitoring device is powered on in response to a connection between the monitoring unit with the base.

In some embodiments, the tactile sensing device comprises a sensor breakout board (not shown in the figures). In some embodiments, the sensor breakout board comprises minimal electronics that are disposable. In some embodiments, the sensor breakout board is configured to connect the sensor driver and acquisition circuitry from the monitoring device to the sensor array. In some embodiments, the sensor breakout board comprises a zero insertion force (ZIF) connector for sensor array connection. In some embodiments, the sensor breakout board comprises an analog multiplexer (MUX) and a bit shifter to support scanning and output. In some embodiments, position sensors to track device movement are comprised in the disposable breakout board. In some embodiments, the monitoring device is powered on upon connection to the breakout board.

In some embodiments, the monitoring device 750 comprises an interface 790 to form an electrical coupling with the interface of the base (e.g. interface 295 of base 210 as depicted in FIG. 2A). In some embodiments, the monitoring device comprises a locking tab 752 which is received by a locking aperture on the base (e.g. aperture 297 of base 210 as depicted in FIG. 2A). The locking tab may facilitate locking of the monitoring device to the base and a secure connection between the interface of the base and the interface of the monitoring device. The locking tab may facilitate removal of the monitoring device from the base by a user. In some embodiments, as depicted in 7A-B, the monitoring device comprises a protrusion 791 which is inserted into the base to facilitate interfacing between the monitoring device and the base.

In some embodiments, the monitoring device comprises a display screen 760. In some embodiments, the display screen is a touchscreen. In some embodiments, the display screen has an adjustable angle. In some embodiments, the display screen is a full-color LCD display. In some embodiments, the display screen is connected to the PCBA and mechanically integrated in the anterior surface of the housing of the module, to allow for output visualization. In some embodiments, the tactile sensing device wirelessly interfaces with an external display, such as a tablet or computer. In some embodiments, the display is collapsed to reduce tactile sensing device footprint.

In some embodiments, the monitoring device comprises a battery 770. In some embodiments, the battery is a rechargeable battery. In some embodiments, the battery is a lithium ion battery. In some embodiments, the rechargeable battery interfaces with the PCBA. In some embodiments, the tactile sensing device comprises a battery indicator. In some embodiments, the battery indicator is a charging indicator. In some embodiments, the charging indicator alerts the user of a low battery. In some embodiments, the charging indicator alerts the user of the amount of battery charged during the charging process. In some embodiments, the battery indicator is on-screen. In some embodiments, the battery indicator is an LED. In some embodiments, the device is powered via USB connection to a computer.

In some embodiments, the monitoring unit stores imaging data. In some embodiments, the monitoring unit stores data from the last imaging cycle before the device powers off. In some embodiments, imaging data are stored if they exceed a certain pressure threshold. In some embodiments, the stored data includes raw sensor data. In some embodiments, the stored data includes aggregate pressure maps. In some embodiments, the stored data included timestamps and position data. In some embodiments, a button on the monitoring unit can be pressed to save the position of the alignment guide at that timestamp. In some embodiments, a graphical user interface feature notifies a user when a position was flagged. In some embodiments, the monitoring unit stores up to five datasets. In some embodiments, the monitoring unit stores a rolling buffer of datasets. In some embodiments, a graphical user interface feature alerts a user to the number of the dataset that is being stored. In some embodiments, the stored data can be transferred to a computer. In some embodiments, the monitoring unit can be operatively connected to a computer. In some embodiments, the monitoring unit is placed in a charging station, and a cable is used to connect to a computer via USB.

In some embodiments, the rechargeable battery located within the tactile sensing device is charged using a reusable charging station (not shown in the figures). In some embodiments, the charging unit comprises standard electronics, including electrical contacts for mating with the computing unit (i.e., with PCBA). In some embodiments, the charging station is housed in a two-part injection molded plastic. In some embodiments, the charging station comprises a charging indicator. In some embodiments, the charging station employs induction charging. In some embodiments, the battery is charged using a power adapter with a cable to be plugged into an inlet of the monitor device.

Figure 7B:
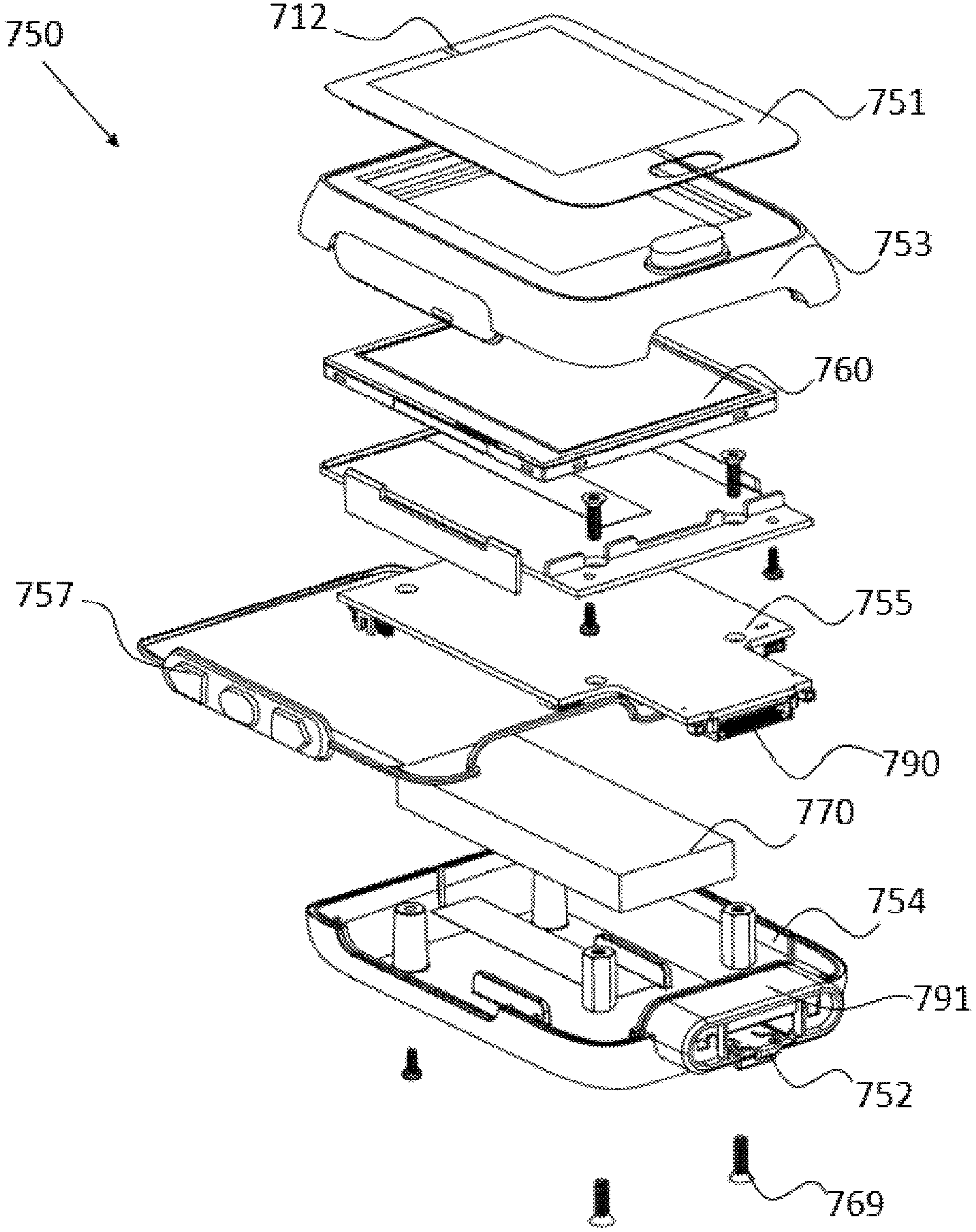
FIG. 7B shows an exploded view of a monitoring device component of a tactile sensing and guidance system, according to some embodiments.

With reference to FIG. 7B, an exploded view depicting the components of monitoring device 750 is shown, according to some embodiments. In some embodiments, the monitoring device 750 comprises a protective screen or overlay 751. In some embodiments, the protective screen comprises a midline indicator 712. In some embodiment, the midline indicator is printed on an interior of the protective screen to prevent wear. In some embodiments, the monitoring device 750 comprises a protective case comprising a front portion 753 and a rear portion 754. In some embodiments, the monitoring device 750 comprises a monitor or screen 760. In some embodiments, the monitoring device 750 comprises a battery 770. In some embodiments, the monitoring device 750 comprises a printed circuit board assembly (PCBA) 755. In some embodiments, the monitoring device 750 comprises a button gasket 757. The button gasket may form a moisture barrier for the monitoring device. In some embodiments, the button gasket provides surfaces for the button on the side of the monitoring device. In some embodiments, one or more components of the monitoring device are fastened together with screws 769, or other similar fastening devices.

Figure 8A:
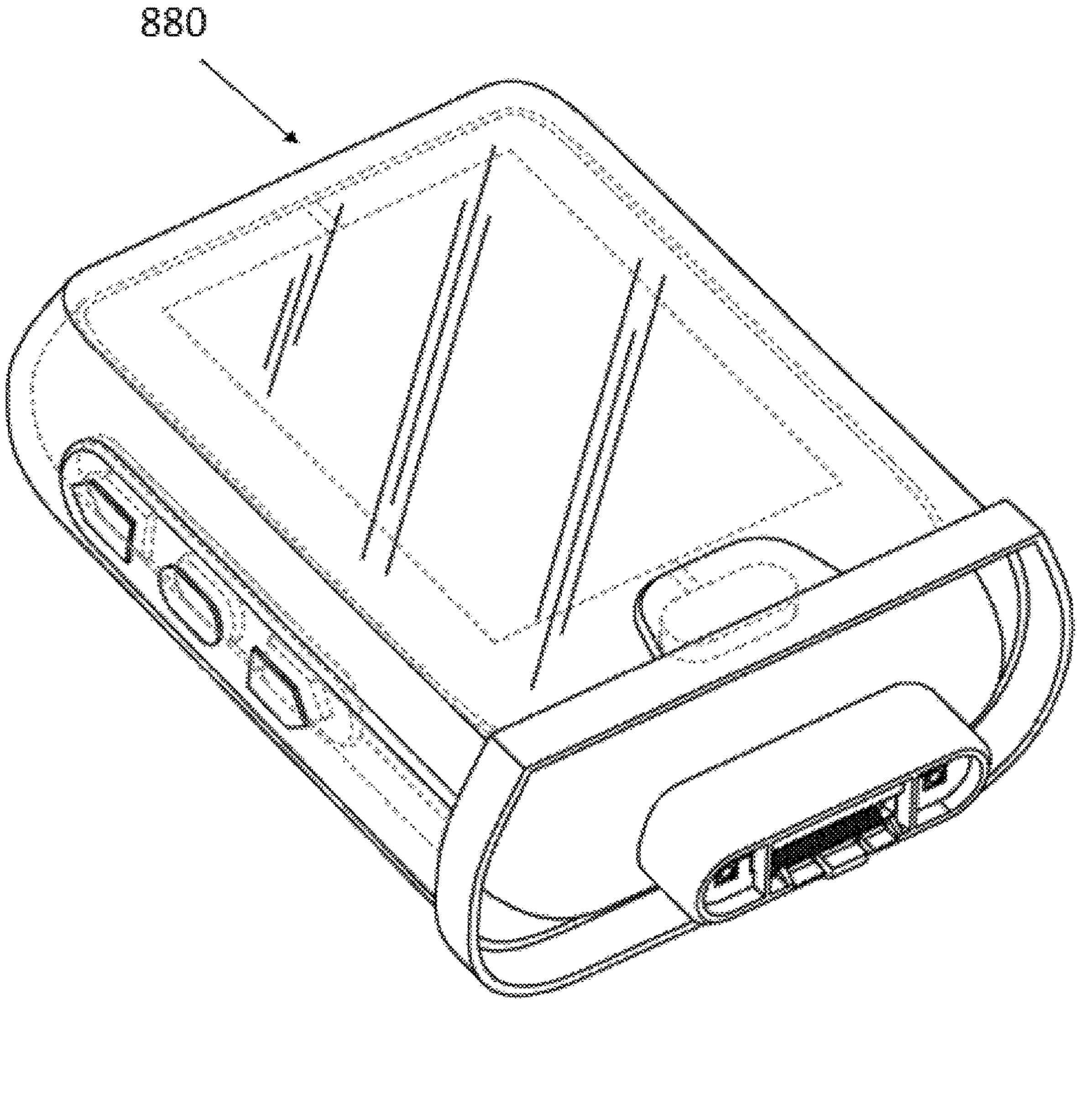
FIG. 8A shows a monitoring device component coupled with a sleeve component of a tactile sensing and guidance system, according to some embodiments.

In some embodiments, the tactile sensing device comprises a sleeve 880 to receive the monitoring device. An embodiment of the sleeve 880 is depicted in FIG. 8A. In some embodiments, the sleeve is a single-component part that is sterile. In some embodiments, the sleeve is a two-component part that is sterile. In some embodiments, wherein the sleeve is a two-component part, a bottom component of the sleeve is configured as part of the base. In some embodiments, the sleeve shrouds the reusable monitoring device during use to provide a sterile outer surface for the reusable monitor device, which is nonsterile, thereby allowing the reusable monitor device to be introduced into a sterile field. In some embodiments, the sleeve is made of medical-grade polyethylene terephthalate glycol-modified (PETG). In some embodiments, the sleeve is comprised of medical-grade thermoplastic polyurethane (TPU) In some embodiments, the sleeve is vacuum-formed to a mold of the reusable monitoring device. In some embodiments, the sleeve comprises a low-reflectivity, transparent component over the display area. In some embodiments, the sleeve has openings and/or depressible covers for user-input buttons. In some embodiments, the sleeve comprises a midline indicator.

Figure 8B:
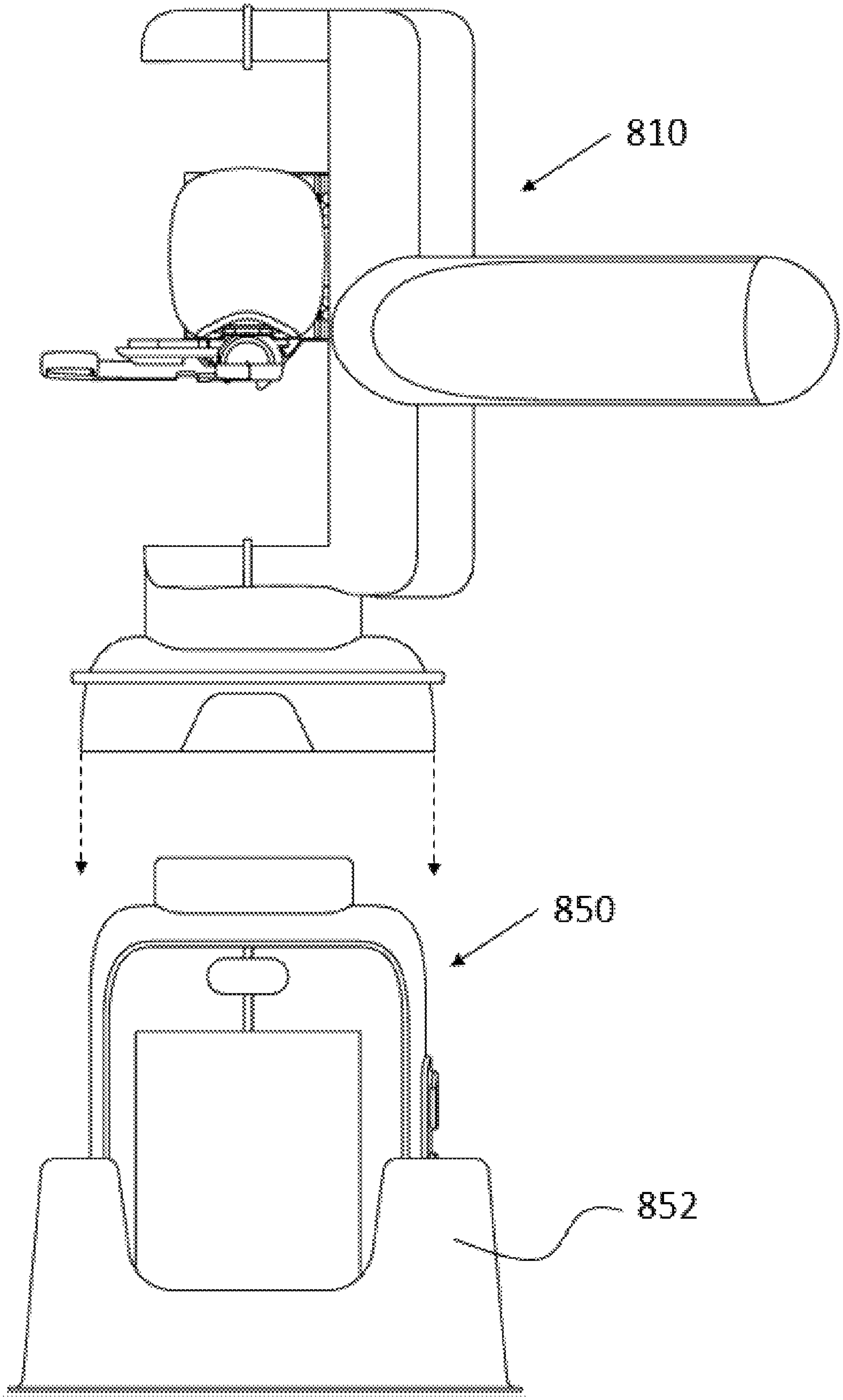
FIG. 8B shows a monitoring device component received by a dock in preparation to be coupled to a base component of a tactile sensing and guidance system, according to some embodiments.

In some embodiments, as depicted in FIG. 8B, the monitoring device 850 may be loaded into a dock 852. The dock may provide the monitoring device in a position ready to be received by a base 810. Use of the dock 852 may help maintain a sterile field of use.

II. METHODS OF USE

A. Historical and Real Time Image Visualization

In some embodiments, the tactile sensing device comprises a computing device. In some embodiments, the computing device comprises a computer program. In some embodiments, the computer program is, for example, software, including computer algorithms, computer codes, and/or programs, which manages the device's hardware and provides services for execution of instructions such as real-time imaging. In some embodiments, the tactile sensing device comprises a computer algorithm to build up an image from at least two images. In some embodiments, the position of the images on the pressure map is determined from data obtained by the position sensor. In some embodiments, the algorithm takes as an input the type of tactile sensing device being used. In some embodiments, the algorithm automatically determines the type of tactile sensing device being used. In some embodiments, the algorithm automatically selects image-display steps depending on the type of tactile sensing device being used. In some embodiments, the algorithm adjusts drive voltage based on a header in an equilibration file. In some embodiments, imaging is initiated by pressing a touchscreen or physical button. In some embodiments, imaging is automatically initiated when the device is pressed against a skin surface. In some embodiments, the imaging sequence is automatically initiated when the monitor device is powered on. In some embodiments, the drive voltage is approximately between 0 and 3.3 V. In some embodiments, the pressure sensor changes resistance in response to pressure. In some embodiments, the algorithm captures pressure sensor data for the current time. In some embodiments, the algorithm converts current to voltage using a gain resistor. In some embodiments, the algorithm reads the voltage as an analog-to-digital count based on a reference voltage. In some embodiments, the reference voltage is 2.5 V. In some embodiments, the algorithm applies a Gaussian filter to the current data. In some embodiments, the algorithm determines the active area of the current data. In some embodiments, the active area of the current data is determined by obtaining an ordered list of data rows, ignoring rows below a cutoff, and determining the indices of the largest contiguous region of rows above a cutoff. In some embodiments, the active area of the current data is automatically determined based on known scanhead size and current scanhead position. In some embodiments, current scanhead position is determined from a position sensor, such as a potentiometer. In some embodiments, a polynomial approximation of the current data is used in order to apply a flat-field correction to remove artifacts. In some embodiments, the current data are scaled between 0 and 1 by dividing by the sum of the current data and mapping to the scale of displayed data for the previous time. In some embodiments, current displayed data is determined by finding the maximum for each pixel when comparing the current data to the previous displayed data. In some embodiments, the current displayed data is the cumulative sum of previously displayed data. In some embodiments, the current displayed data is then saved as the previous displayed data. In some embodiments, the current displayed data is displayed to the screen of the tactile sensing device. In some embodiments, an imaging cycle is completed when a scanhead has been translated along the full length of a scanning track.

In some embodiments, the active area is highlighted on the display using rectangular or circular patches. In some embodiments, the active area is highlighted with an outline that has the same width and height of the active area of the pressure sensor. In some embodiments, the algorithm displays a line corresponding to the midline. In some embodiments, the algorithm displays a crosshair corresponding to the location of the alignment guide relative to the current display data. In some embodiments, the location of the alignment guide is determined by position sensor data and a known distance between the alignment guide and the center of the pressure sensor. In some embodiments, the crosshair represents a real-time position of the alignment guide. In some embodiments, a circular feature of the crosshair represents the functional tolerance of insertion allowed by the track of the guide. In some embodiments, the display screen displays an arrow indicating the direction in which the tactile sensing device should be moved to localize the target tissue location. In some embodiments, the graphical user interface includes tick marks for the horizontal and vertical axes of the pressure map. In some embodiments, the algorithm takes as inputs a patient identifier, patient weight, and patient height. In some embodiments, the algorithm can change screen brightness based on brightness input from a touchscreen or physical button. In some embodiments, the algorithm can change the colormap based on input from a touchscreen or physical button. In some embodiments, the algorithm takes as an input a sensitivity factor. In some embodiments, the sensitivity factor is selected using a touchscreen or physical button, or a dial. In some embodiments, the sensitivity defaults to 70% of the total sensitivity range. In some embodiments, the sensitivity can be adjusted between 30% and 100% of the total sensitivity range. In some embodiments, the sensitivity can be adjusted to approximately 15% above and approximately 25% below a normal sensitivity. In some embodiments, the sensitivity factor is used to rescale the colormap of currently displayed data. In some embodiments the sensitivity factor is used to adjust the drive voltage. In some embodiments, the drive voltage can be adjusted between 0 and 3.3V. In some embodiments, the reference voltage is 2.5 V. In some embodiments the sensitivity is a ratio of drive to reference voltage. In some embodiments the default ratio of drive to reference voltage is 2. In some embodiments, the sensitivity factor is used as the cutoff in determining the active area of current data. In some embodiments, sensitivity is automatically adjusted based on patient BMI, as inputted or calculated from height and weight. In some embodiments, the algorithm displays a splash screen before imaging is initiated. In some embodiments the user can press a touchscreen or physical button to access a menu of input items. In some embodiments, the user can scroll through menu items using touchscreen or physical buttons or a dial. In some embodiments, the algorithm contains steps to threshold pressure sensor data. In some embodiments, the algorithm contains steps for equilibration and calibration of the sensor array. In some embodiments, the user can remove high points that show up in current displayed data during application of no force by pressing a touchscreen or physical tare button. In some embodiments, the algorithm automatically removes high points during zero-force application. In some embodiments, the user can refresh the current displayed data by pressing a touchscreen or physical refresh button. In some embodiments, the algorithm can detect if the device is aligned with the midline. In some embodiments the algorithm uses position sensors, such as an accelerometer, to detect if the device is aligned with the midline. In some embodiments, the algorithm can alert the user to off-midline imaging. In some embodiments, the algorithm can automatically refresh the currently displayed data if it corresponds to off-midline imaging. In some embodiments, the algorithm can detect if the tactile sensing device has changed orientation or been moved laterally during an imaging cycle. In some embodiments the algorithm can detect device movement using a position sensor, such as a potentiometer, or a magnetic or optical sensor. In some embodiments, the algorithm can alert the user to device movement during an imaging cycle. In some embodiments, the algorithm can automatically refresh currently displayed data if it detects incorrect device reorientation or movement.

In some embodiments the algorithm pulls calibration into a runtime memory. In some embodiments, the algorithm captures sensor data using a nested loop. In some embodiments, the sensor data is raw sensor data based on changes in resistance due to pressure applied during a push of the scanhead. In some embodiments, pressure applied to a sensor causes a drop in resistance value for said sensor. In some embodiments, each reading of a sensing element is an average of at least 5 analog reads of that sensing element. In some embodiments, the algorithm reads voltage as an ADC count based on reference voltage. In some embodiments the sensor data is converted into 8 bit data. In some embodiments, the algorithm stores current sensor data in the form of an array of approximately 12×8. In some embodiments, the algorithm stores an aggregate heatmap. In some embodiments, the algorithm stores an aggregate heatmap that is approximately 34×8. In some embodiments, the algorithm captures an ADC value of the linear position sensor. In some embodiments, the algorithm maps the array of current sensor data to an aggregate heatmap using data from the position sensor. In some embodiments, the algorithm blends the array of current sensor data into an aggregate heatmap. In some embodiments, the algorithm determines the maximum value between the aggregate heatmap and the overlapping pixels in the current sensor data in order to blend the current sensor data into the aggregate heatmap. In some embodiments, the algorithm performs a normalization of blended sensor data. In some embodiments the blending process is repeated more than one time in each imaging cycle for each push of the scanhead. In some embodiments, the blending process is repeated as many times as required to fill the imaging range. In some embodiments, the algorithm determines a noise level and eliminates current sensor data before or after blending below a threshold noise level. In some embodiments, a noise level is determined from an average of current sensor data obtained from the sensor array. In some embodiments, the algorithm performs an error check for dead pixels in current sensor data before or after blending. In some embodiments, the algorithm performs an error check for saturated or dead rows or columns in current sensor data before or after blending. In some embodiments, the algorithm triggers a warning to errors identified during an error check. In some embodiments, the algorithm tares individual erroneous pixels in current sensor data before or after blending during imaging. In some embodiments, the algorithm performs calibration correction on current sensor data before or after blending. In some embodiments, the algorithm adjusts values in current sensor data before or after blending that are bigger than 5 calibration points. In some embodiments, the algorithm applies a Gaussian blur to the current sensor data before or after blending. In some embodiments, the Gaussian blur may have a standard deviation of 0.55 pixels. In some embodiments, the algorithm uses bicubic interpolation to interpolate current sensor data to a size appropriate for display. In some embodiments the algorithm interpolates the region corresponding to current sensor data before or after blending. In some embodiments, the algorithm interpolates the aggregate heatmap. In some embodiments, the algorithm interpolates the aggregate heatmap to approximately 296×70. In some embodiments, the algorithm maps aggregate heatmap values to the color of the display screen in the monitoring device. In some embodiments, the heatmap is a full 5-color heatmap, comprising a color scale of black, blue green, yellow, and red. In some embodiments, the heatmap is a blue to red colormap that passes through the colors cyan, yellow, and orange. In some embodiments, the lowest RGB value in the colormap is replaced with black. In some embodiments, blue and red outputs correspond to areas of low and high pressure, respectively. In some embodiments, the algorithm crops the heatmap to a size appropriate for the screen of the monitoring device. In some embodiments, the algorithm sends the data to be displayed on the screen of the monitor device. In some embodiments, the algorithm displays the heatmap with a ratio of approximately 1:1 relative to the scanned anatomy based on the size of the imaging range. In some embodiments, the imaging range is approximately 64.7 mm in height and 15.2 mm in width. In some embodiments, the algorithm refreshes the display at least every 100 ms. In some embodiments, the algorithm will display a black color for regions that have not been scanned.

In some embodiments, the algorithm calculates gradients relative to the previous timestamp. In some embodiments, the algorithm uses Gaussian blur to eliminate noisy data via full-image convolution. In some embodiments, the algorithm applies a Laplacian filter to the data. In some embodiments, the algorithm applies a gaussian filter prior to applying a Gaussian filter (Laplacian of Gaussian operation). In some embodiments, the algorithm applies a least square fit and calculates bias in the image. In some embodiments, the algorithm enhances the pressure map image by using a histogram and resulting cumulative distribution function to spread a color scale over the dynamic range and increase a contrast of colors displayed by the pressure map image. In some embodiments, the algorithm produces a histogram of oriented gradients using nearest neighbor interpolation.

In some embodiments, FIGS. 9A-E depict the workflow of how a user utilizes the tactile sensing system to image a target tissue location of a patient with respect to the graphical interface of the monitoring device. In some embodiments, the graphic interface comprises a pressure map 905, a scanhead location 915, a force indicator 910, an alignment guide indicator 920, a midline indicator 925, a battery level indicator 930, and a sensitivity level indicator 935. In some embodiments, the pressure map further comprises coordinates of the X and Y axes.

Figures 9A, 9B, 9C, 9D, 9E, 9F:
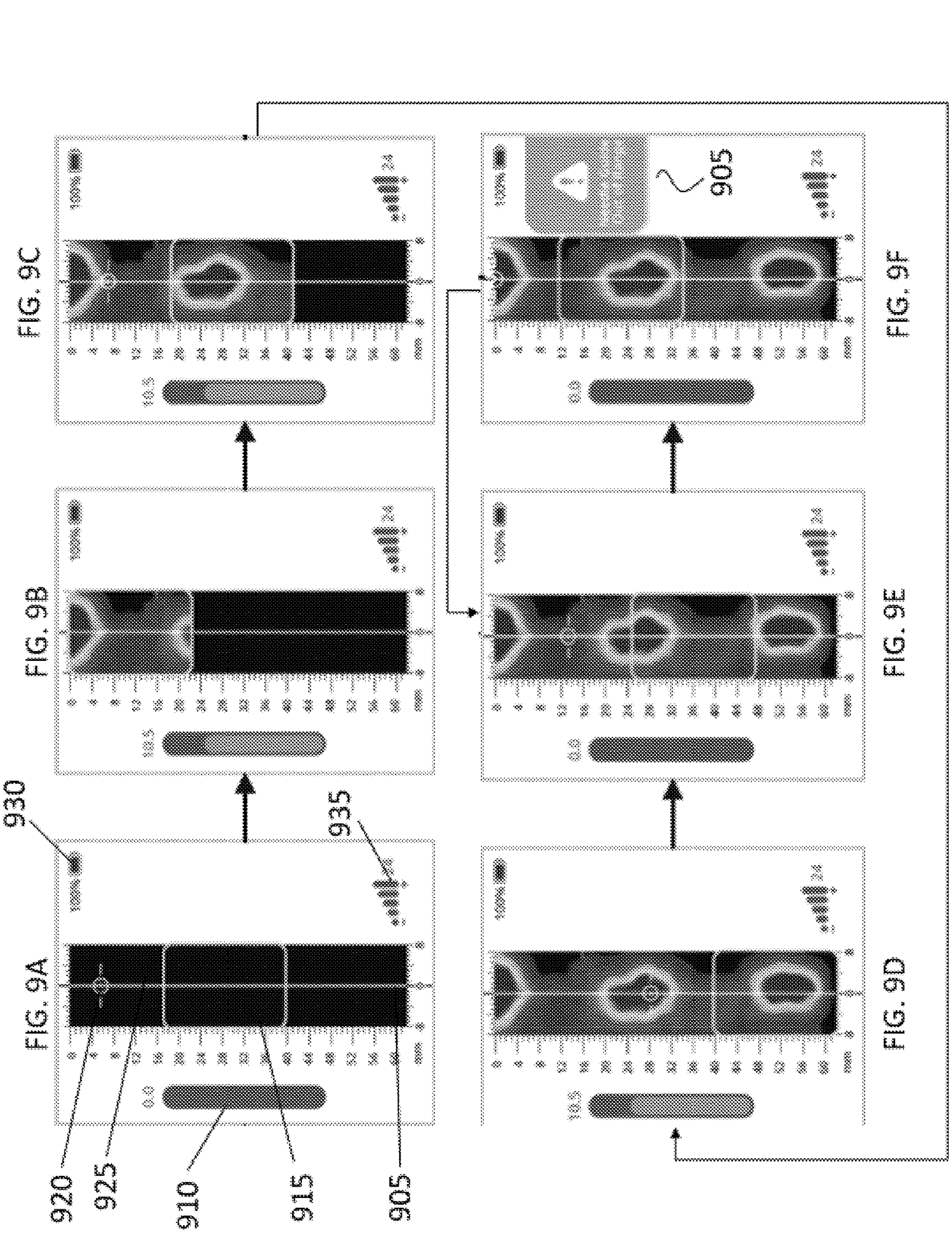
FIG. 9A depicts a graphical user interface of a monitoring device of a tactile sensing and guidance system, according to some embodiments.
FIG. 9B depicts a graphical user interface of a monitoring device of a tactile sensing and guidance system, according to some embodiments.
FIG. 9C depicts a graphical user interface of a monitoring device of a tactile sensing and guidance system, according to some embodiments.
FIG. 9D depicts a graphical user interface of a monitoring device of a tactile sensing and guidance system, according to some embodiments.
FIG. 9E depicts a graphical user interface of a monitoring device of a tactile sensing and guidance system, according to some embodiments.
FIG. 9F depicts a graphical user interface of a monitoring device of a tactile sensing and guidance system, according to some embodiments.

According to some embodiments, FIG. 9A depicts a graphical interface of the monitoring device before imaging of the target tissue location begins, wherein no image has been formed on the pressure map.

In some embodiments, FIG. 9B depicts a pressure map recorded at a first position. At said first position, a user has depressed the sensor array onto the target tissue area of a patient with a force as indicated by the force indicator 910. The image at said first position has been captured and is displayed on to the pressure map 905.

In some embodiments, FIG. 9C depicts a pressure map recorded at a second position. At said second position, a user has depressed the sensor array onto the target tissue area of a patient with a force as indicated by the force indicator 910. The image at said second position has been captured and is displayed on to the pressure map 905.

In some embodiments, FIG. 9D depicts a pressure map recorded at a third position. At said third position, a user has depressed the sensor array onto the target tissue area of a patient with a force as indicated by the force indicator 910. The image at said third position has been captured and is displayed on to the pressure map 905.

In some embodiments, FIG. 9E depicts a fully imaged pressure map 905, wherein the user has aligned the alignment guide indicator 920 at a target location. In some embodiments, the user places a marker through the alignment guide of the tactile sensing system to mark the location as indicated by the alignment guide indicator 920. The marked location may signify an insertion site for a needle. In some embodiments, the user places a needle into a needle guide of the tactile sensing system to proceed at the location as indicated by the alignment guide indicator.

In some embodiments, FIG. 9F depicts a graphical interface wherein the user has positioned the alignment guide out of the range of the pressure map. In some embodiments, the user will be notified by an alert 950 on the graphical interface and will be prompted to position the alignment guide to a proper position, as depicted in FIG. 9E.

In the embodiment depicted by FIGS. 9A-F, pressure images are generated at three positions along the pressure map. However, one may recognize that more or fewer pressure images may be required depending on the size of the sensor array and/or the target tissue location being imaged. In some embodiments, a user can overlap the positions of the pushes of the scanhead along the track resulting in more than three positions.

In some embodiments, the force indicator provides a guide for the user to determine how much force should be applied to the scanhead during depression of the sensor array onto the target tissue location of a patient to allow for consistent pressures to be applied across the entire pressure map 905. In some embodiments, the force applied is solely at the discretion of the user, and the user must try to match the force applied at the first position. In some embodiments, the system captures a pressure image when a predetermined force is reached. In some embodiments, a mechanism is provided to limit the force which may be applied by the user to allow for uniform pressure measurements across the pressure map.

In some embodiments, the force indicator depicts a calibrated measurement and displays the applied force measured from the sensor. According to some embodiments, the displayed measurement for the force indicator is obtained by averaging the analog-to-digital converter (ADC) value for the array (e.g. 12×8 sensor array) and dividing by 10 to obtain an approximate range of pounds. The approximated range is then scaled by the sensitivity, which is the drive voltage divided by double the reference voltage (e.g. 2). For example, given v_drive=255 ADC counts, v_ref=127 ADC counts, and v_avg=95 ADC counts, the force measurement would be calculated as 95/[10*(255/2*127)]=9.5 lbs.

In some embodiments, the force measurement is divided by the maximum force value (e.g. 14 pounds) and the fraction of the calculated force and maximum force value is displayed on the force indication bar. In some embodiments, the resolution of the force indicator is 0.1 lbs. In some embodiments, the force indication bar further comprises a color changing scheme to further indicate and display the force being applied. In some embodiments, the force indicator bar comprises a single color.

B. Device Configuration and Procedures

Figure 10A:
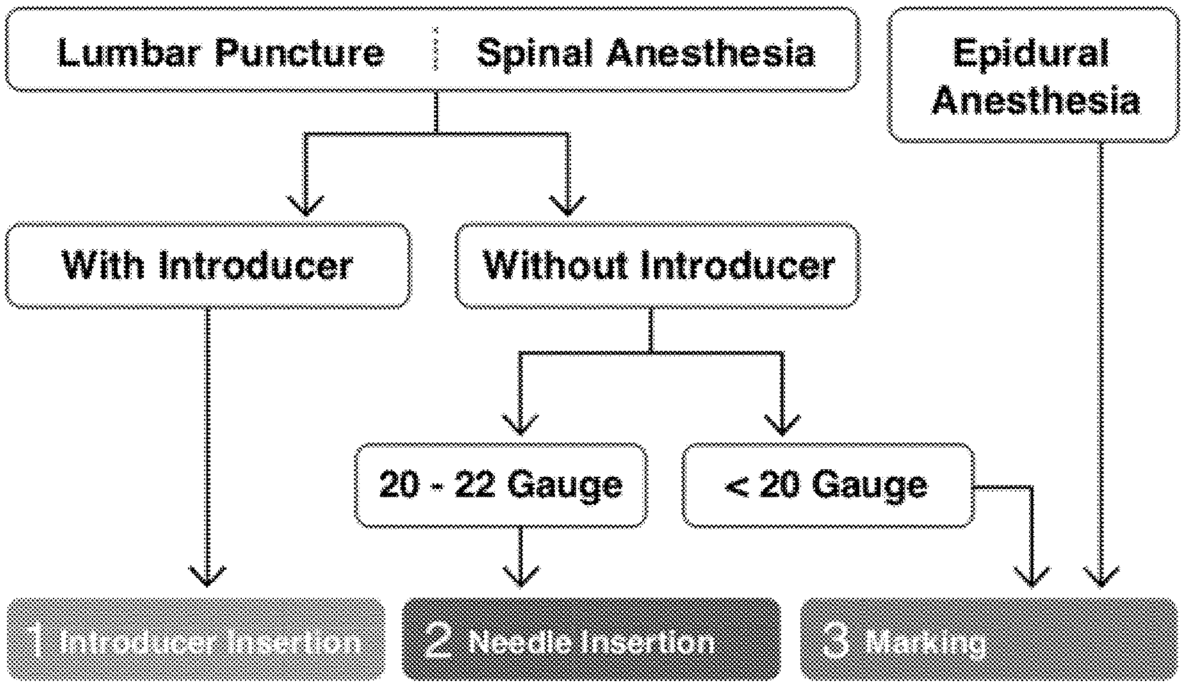
FIG. 10A shows a flowchart depicting a method of use of a tactile sensing and guidance system, according to some embodiments.

With reference to FIG. 10A, a flowchart is depicted which details how the tactile sensing device should be configured based on various applications. At a first step, a determination is made as to what procedure is to be done.

In some embodiments, if the procedure is a spinal anesthesia procedure with an introducer to be utilized, then an introducer insertion configuration and procedure should be followed. In some embodiments, an introducer configuration comprises using the fully assembled tactile sensing and needle guidance system with the depth restrictor at a neutral position (i.e. no depth restriction mechanism utilized).

Figure 10B:
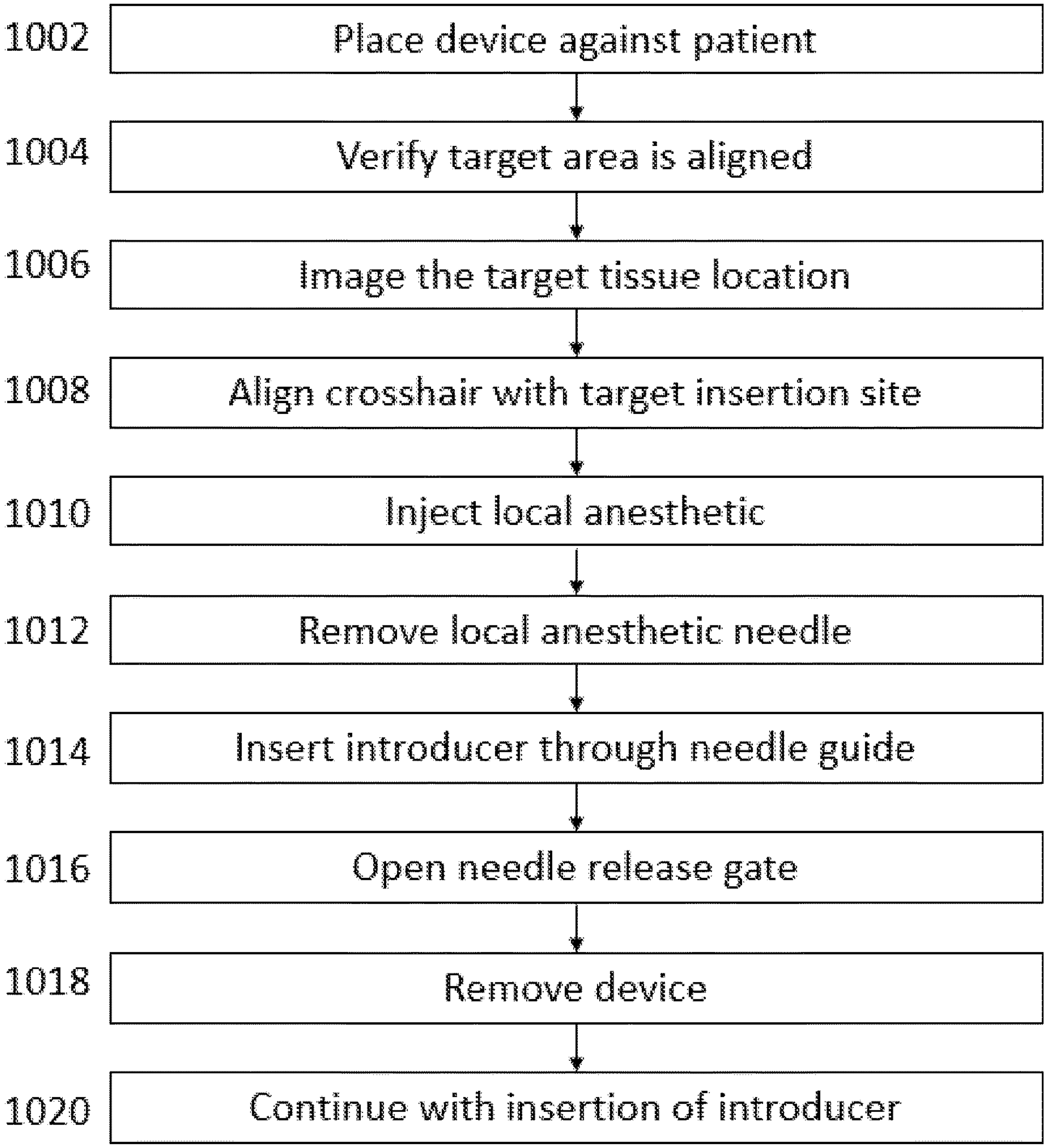
FIG. 10B depicts a method of use of a tactile sensing and guidance system, according to some embodiments.

In some embodiments, and with reference to FIG. 10B, the introducer placement procedure comprises gripping the handle and placing the device against the patient's back at a first step 1002. In some embodiments, the procedure comprises checking and verifying that the target area and crosshair provided on the display of the monitoring device are properly aligned at step 1004. In some embodiments, the procedure comprises imaging the target tissue location using the tactile sensing device at step 1006. In some embodiments, the procedure comprises sliding the carriage until the crosshair is aligned with the target insertion site at step 1008. In some embodiments, the procedure comprises injecting local anesthetic (LA) through the needle guide at step 1010. In some embodiments, the procedure comprises removing the local anesthetic syringe at step 1012. In some embodiments, the procedure comprises, inserting the introducer through the needle guide at step 1014. In some embodiments, the procedure comprises ensuring the introducer is securely in place and opening the needle release gate at step 1016. In some embodiments, the procedure comprises removing the tactile sensing device away from the target tissue site and placing the device back into a sterile field while keeping the introducer inserted into the patient at step 1018. In some embodiments, the procedure comprises proceeding to insert the introducer needle without use of the device at step 1020.

With further reference to FIG. 10A, in some embodiments, if the procedure is a lumbar puncture that utilizes a needle with a gauge of 20-22 and a length that has an associated restrictor height configuration, then a needle insertion configuration and procedure should be followed. In some embodiments, the length of the needle has an associated restrictor configuration. In some embodiments, a needle insertion configuration comprises using the fully assembled tactile sensing and needle guidance system with the depth restrictor at a neutral position for injection of a local anesthetic, then adjusting the depth restrictor according to the size of the needle being used in the procedure.

Figure 10C:
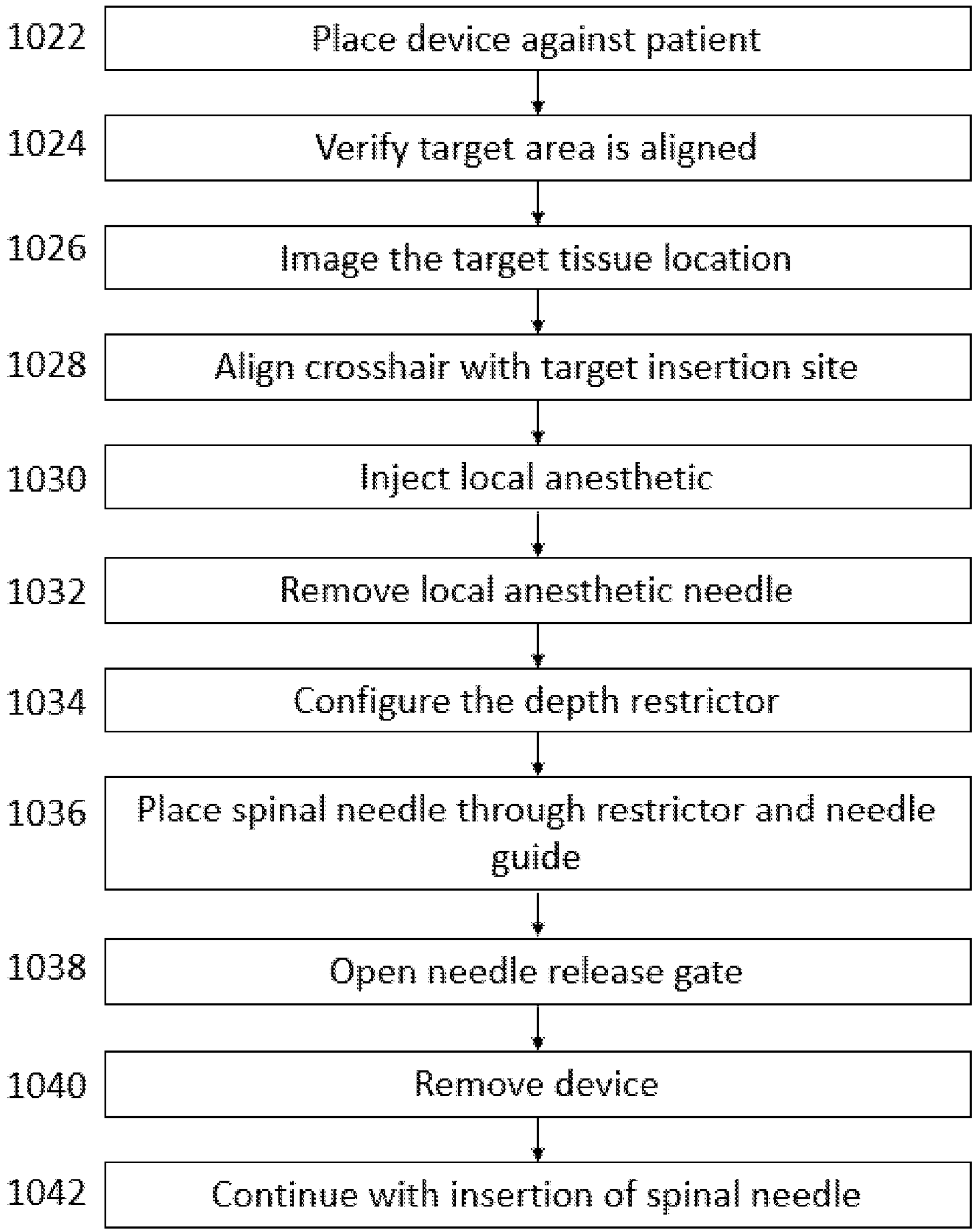
FIG. 10C depicts a method of use of a tactile sensing and guidance system, according to some embodiments.

In some embodiments, and with reference to FIG. 10C, the needle insertion procedure comprises gripping the handle and placing the device against the patient's back at step 1022. In some embodiments, the procedure comprises checking and verifying that the target area and cross-hair provided on the display of the monitoring device are properly aligned at step 1024. In some embodiments, the procedure comprises imaging the target tissue location using the tactile sensing device at step 1026. In some embodiments, the procedure comprises sliding the carriage until the crosshair is aligned with the target insertion site at step 1028. In some embodiments, the procedure comprises injecting local anesthetic (LA) through the needle guide at step 1030. In some embodiments, the procedure comprises removing the local anesthetic syringe at step 1032. In some embodiments, the procedure comprises, adjusting the depth restrictor to configure to the size of the spinal needle at step 1034. In some embodiments, the restrictor at a lower position of will be used if the spinal needle is about 3.5 inches. In some embodiments, the restrictor at an upper position will be used if the spinal needle is about 5 inches. In some embodiments, the procedure comprises placing the spinal needle into the target tissue location to a depth permitted by the restrictor at step 1036. In some embodiments, the procedure comprises opening the needle release gate at step 1038. In some embodiments, the procedure comprises removing the tactile sensing device away from the target tissue site and placing the device back into a sterile field while keeping the introducer inserted into the patient at step 1040. In some embodiments, the procedure comprises proceeding without use of the device at step 1042.

With further reference to FIG. 10A, in some embodiments, if the procedure is a neuraxial procedure that does not utilize an introducer and utilizes a needle having a gauge less than 20 (i.e. a needle with a larger diameter than a 20 gauge needle), then a marking configuration and procedure should be followed. In some embodiments, if the procedure is an epidural anesthesia, then a marking configuration and procedure should be followed. In some embodiments, a marking configuration comprises removing the needle guide and release gate to expose the alignment guide.

Figure 10D:
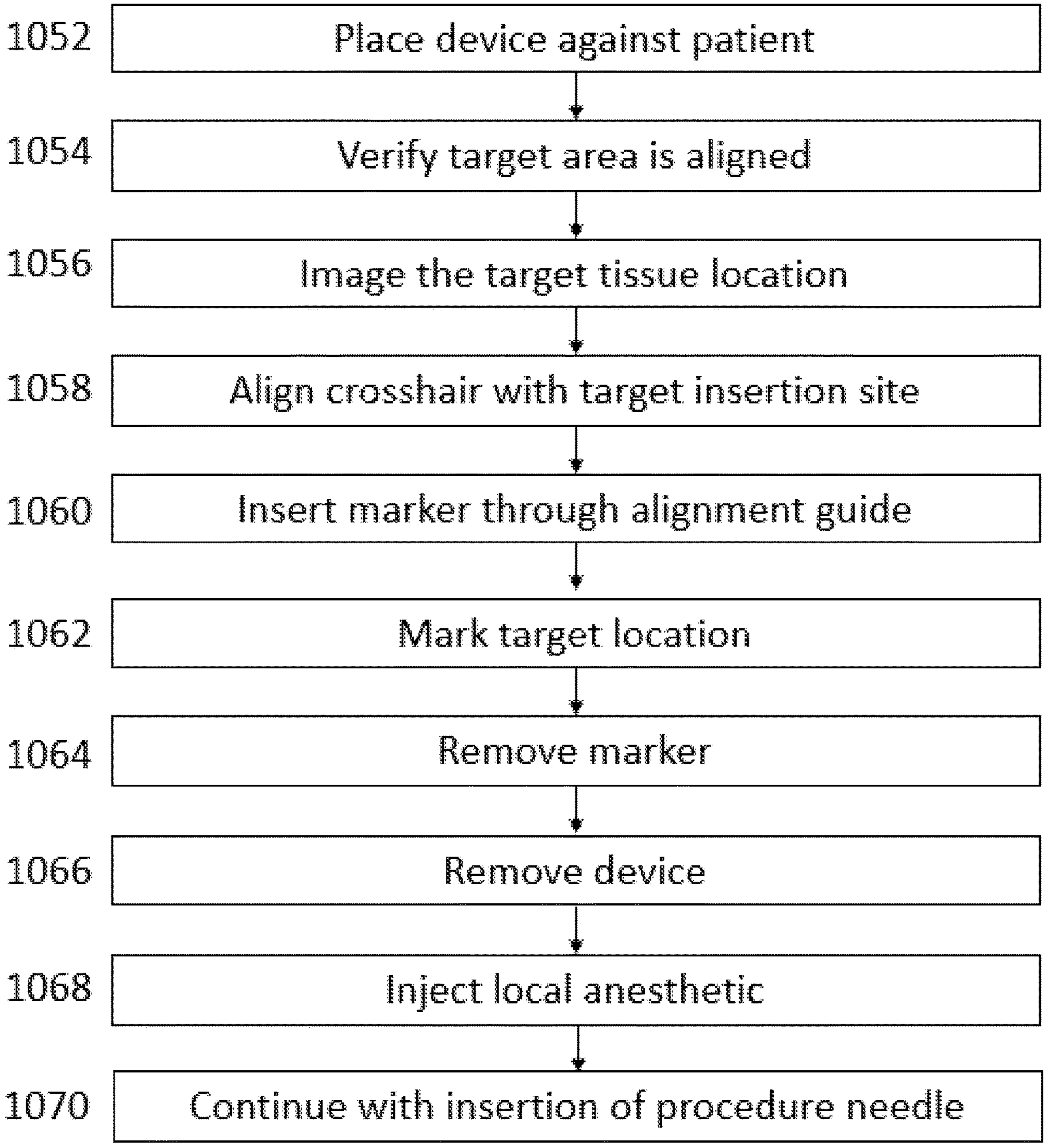
FIG. 10D depicts a method of use of a tactile sensing and guidance system, according to some embodiments.

With reference to FIG. 10D, according to some embodiments, the procedure for marking a target location comprises verifying that the device is properly set up with the needle guide removed and the alignment guide exposed. In some embodiments, the procedure comprises gripping the handle and placing the device against the patient's back at step 1054. In some embodiments, the procedure comprises checking and verifying that the target area and crosshair provided on the display of the monitoring device are properly aligned at step 1054. In some embodiments, the procedure comprises imaging the target tissue location using the tactile sensing device at step 1056. In some embodiments, the procedure comprises sliding the carriage until the crosshair is aligned with the target insertion site at step 1058. In some embodiments, the procedure comprises inserting a sterile surgical marker through the guide at step 1060 and pressing the marker against the patients back at step 1062. In some embodiments, the procedure comprises removing the marker from the guide at step 1064. In some embodiments, the procedure comprises removing the tactile sensing device away from the target tissue site and placing the device back into a sterile field at step 1066. In some embodiments, the procedure comprises injecting a local anesthetic at step 1068. In some embodiments, the procedure comprises proceeding without use of the device at step 1070. In some embodiments, the procedure comprises a lumbar puncture or insertion of a spinal needle.

III. CURRENTLY PREFERRED EMBODIMENT

1. In one currently preferred embodiment, the invention provides tactile sensing device, comprising: a base comprising: a scanning track; a carriage configured to slide along the scanning track; a scanhead mounted to the carriage; and a sensor array attached to the scanhead, the sensor array comprising one or more pressure sensors, each pressure sensor configured to output a voltage signal in response to a change in pressure.

2. The tactile sensing device of paragraph 1, wherein in the carriage comprises an alignment guide.

3. The tactile sensing device of any one of paragraphs 1 to 2, further comprising a needle guide configured to reversibly attach to the carriage.

4. The tactile sensing device of paragraph 3, wherein the needle guide further comprises a removal tab.

5. The tactile sensing device of any one of paragraphs 1 to 4, further comprising a needle release gate configured to reversibly attach to the carriage.

6. The tactile sensing device of paragraph 5, wherein the needle release gate is configured to reversibly secure a needle to the carriage in a position concentric with the needle guide.

7. The tactile sensing device of paragraph 3, wherein the needle guide further comprises a connector plate.

8. The tactile sensing device of paragraph 7, further comprising a connector coupled to a depth restrictor, wherein the connector removably attaches to the connector plate of the needle guide, thereby allowing the depth restrictor to be placed in a first position in alignment with the needle guide and a second position out of alignment with the needle guide.

9. The tactile sensing device of paragraph 8, wherein the connector is coupled to the depth restrictor to allow the depth restrictor to be positioned at an upper position away from the needle guide or at a lower position proximal to the needle guide.

10. The tactile sensing device of paragraph 9, wherein the upper position is configured for placement of a 5 inch needle.

11. The system of paragraph 10, wherein the upper position limits the depth of a 5 inch needle from about 0.5 centimeters to about 5 centimeters.

12. The tactile sensing device of paragraph 9, wherein the lower position is configured for placement of a 3.5 inch needle.

13. The tactile sensing device of paragraph 12, wherein the upper position limits the depth of a 3.5 inch needle from about 1 centimeter to about 3.5 centimeters.

14. The tactile sensing device of any one of paragraphs 7 to 12, further comprising a needle release gate configured to reversibly attach to the carriage.

15. The tactile sensing device of paragraph 14, wherein the needle release gate is configured to reversibly secure a needle to the carriage in a position concentric with the needle guide.

16. The tactile sensing device of any one of paragraphs 1 to 15, further comprising a bottom pad forming a distal surface of the tactile sensing device.

17. The tactile sensing device of paragraph 16, wherein the bottom pad is configured to rest on a skin surface of a patient.

18. The tactile sensing device of any one of paragraphs 16 to 17, wherein the bottom pad is provided with a concave curvature having radius of approximately 1 meter.

19. The tactile sensing device of any one of paragraphs 16 to 18, wherein the bottom pad comprises a hardness of approximately 20 Shore A to 35 Shore A.

20. The tactile sensing device of any one of paragraphs 1 to 19, wherein the scanhead is moveable relative to the carriage.

21. The tactile sensing device of paragraph 20, wherein the scanhead is biased toward a proximal side of the device.

22. The tactile sensing device of paragraph 21, wherein the scanhead is biased by a spring.

23. The tactile sensing device of paragraph 22, wherein the carriage comprises a spring guide.

24. The tactile sensing device of paragraph 23, wherein the scanhead comprises a spring protrusion, and wherein the spring guide and the spring protrusion are configured to center the spring relative to the scanhead and the carriage.

25. The tactile sensing device of any one of paragraphs 1 to 24, wherein the sensor array is a matrix array.

26. The tactile sensing device of any one of paragraphs 1 to 25, wherein the sensor array is a flexible sensor array.

27. The tactile sensing device of any one of paragraphs 1 to 26, wherein the sensor array is attached to a sensor array attachment area.

28. The tactile sensing device of any one of paragraphs 1 to 27, wherein the sensor array is adhered to a distal surface of the scanhead.

29. The tactile sensing device of any one of paragraph 28, wherein the distal surface of the scanhead is curved.

30. The tactile sensing device of any one of paragraph 29, wherein the radius of curvature of the scan head is about 37.5 millimeters.

31. The tactile sensing device any of one of paragraphs 1 to 30, wherein the base further comprises a handle.

32. The tactile sensing device of paragraph 30, wherein the handle comprises a grip feature.

33. The tactile sensing device of any one of paragraphs 1 to 32, further comprising a locking mechanism which prevents the carriage from sliding along the scanning track when the scanhead is depressed.

34. The tactile sensing device of paragraph 33, wherein the locking mechanism comprises one or more locking tabs having a pointed protrusion which engage with an elastomeric strip when the scanhead is depressed.

35. The tactile sensing device of any one of paragraph 1 to 34, further comprising a depth lock to lock a position of the scanhead at a depth relative to the carriage.

36. The tactile sensing device of paragraph 35, further comprising a button to release the scan head from a locked position relative to the carriage.

37. The tactile sensing device of any one of paragraphs 1 to 36, wherein the base further comprises a position sensor.

38. The tactile sensing device of any one of paragraphs 1 to 37, further comprising a monitor device, comprising: a display screen operatively coupled to the sensor array, the display screen configured to display: a pressure map representing a target tissue location in an individual based upon the voltage signals output by the one or more pressure sensors; and a computing device comprising a processor operatively coupled to the sensor array and the monitor device, and a non-transitory computer readable storage medium with a computer program including instructions executable by the processor causing the processor to: i) convert the voltage signals from the sensor array into the pressure map and display the pressure map on the display screen and ii) output an alignment guide location on the display screen.

39. The tactile sensing device of paragraph 38, wherein the base further comprises an interface configured to receive the monitor device.

40. The tactile sensing device of paragraph 39, wherein in the interface comprises an electrical coupling such that the sensor array is in electrical communication with the monitor device when the monitor device is received by the interface.

41. The sensing device of paragraph 39 or 40, wherein the sensor array is electrically coupled to the interface by a flexible printed circuit board.

42. The tactile sensing device of any one of paragraphs 38 to 41, wherein the monitor device is coupled to the sensor array via a flexible printed circuit board.

43. The tactile sensing device of paragraph 42, wherein the flexible printed circuit board electrically connects a position sensor to the monitor device.

44. The system of paragraph 43; wherein the position sensor is operatively coupled to the processor of the computing device, and wherein the computing device receives a position of the sensor array from the position sensor, and wherein the position of the sensor array is utilized to generate the pressure map.

45. The tactile sensing device of any one of paragraphs 38 to 43, wherein the monitor device comprises a printed circuit board.

46. The tactile sensing device of any one of paragraphs 38 to 45, further comprising a sleeve configured for receiving the monitor device.

47. The tactile sensing device of any one of paragraphs 38 to 46, comprising a power source.

48. The tactile sensing device of paragraph 47, wherein the power source is a battery located within the monitor device.

49. The tactile sensing device of any one of paragraphs 38 to 48, wherein the sensor array and the monitor device are reversibly connected.

50. The tactile sensing device of any one of paragraphs 38 to 49, comprising a wireless transmitter, the wireless transmitter operatively connected to the sensor array, for remotely transmitting the voltage signals output by the plurality of sensors.

51. The tactile sensing device of any one of paragraphs 38 to 50, wherein the processor is configured with instructions to display the target tissue location and the alignment guide location on the display screen in real time.

52. The tactile sensing device of any one of paragraphs 38 to 51, wherein the processor is configured with instructions to display a force being applied to the target tissue location in real time.

53. The tactile sensing device of any one of paragraphs 1 to 52, wherein the base further comprises a midline indicator.

54. The tactile sensing device of any one of paragraphs 1 to 53, wherein a distance between a distal surface of the base and a distal surface of the scanhead is approximately 0.1 cm to 5 cm.

55. The tactile sensing device of any one of paragraphs 1 to 54, wherein a distance between a distal surface of the base and a distal surface of the scanhead is approximately 1.8 cm.

56. The tactile sensing device of any one of paragraphs 1 to 55, wherein an active area of the sensor array is approximately 350 $mm^2$.

57. The tactile sensing device of any one of paragraphs 1 to 6, wherein the scanhead further comprises a scanning knob on its proximal side.

58. The tactile sensing device of paragraph 57, wherein the base comprises at least one restrictor guide configured to restrict an insertion depth of a needle.

59. The tactile sensing device of paragraph 58, wherein the scanning knob comprises at least one restrictor guide.

60. The tactile sensing device of paragraph 57, wherein the scanning knob comprises two or more restrictor guides configured to restrict the insertion depth of a needle, and wherein the scanning knob rotates to align one of said two or more restrictor guides with the alignment guide.

61. In one currently preferred embodiment, the invention provides a tactile sensing system, comprising: a base comprising: a scanning track; a carriage configured to slide along the scanning track; a scanhead mounted to the carriage; and a sensor array attached to the scanhead, the sensor array comprising one or more pressure sensors, each pressure sensor configured to output a voltage signal in response to a change in pressure; and a monitor device, comprising: a display screen operatively coupled to the sensor array, the display screen configured to display: a pressure map representing a target tissue location in an individual based upon the voltage signals output by the one or more pressure sensors; and a computing device comprising a processor operatively coupled to the sensor unit and the monitor device, and a non-transitory computer readable storage medium with a computer program including instructions executable by the processor causing the processor to: i) convert the voltage signals from the sensor array into the pressure map and display the pressure map on the display screen and ii) output an alignment guide location on the display screen.

62. The tactile sensing system of paragraph 61, wherein the base further comprises an interface configured to receive the monitor device.

63. The tactile sensing system of paragraph 62, wherein in the interface comprises an electrical coupling such that the sensor array is in electrical communication with the monitor device when the monitor device is received by the interface.

64. The sensing system of any one of paragraphs 62 to 63, wherein the sensor array is electrically coupled to the interface by a flexible printed circuit board.

65. The tactile sensing system of any one of paragraphs 61 to 64, wherein the base further comprises a position sensor.

66. The system of paragraph 65, wherein the position sensor is operatively coupled to the processor of the computing device, and wherein the computing device receives a position of the sensor array from the position sensor, and wherein the position of the sensor array is utilized to generate the pressure map.

67. The system of paragraph 66, wherein the position sensor is electrically coupled to the interface via a flexible printed circuit board.

68. The tactile sensing system of any one of paragraphs 61 to 65, wherein in the carriage comprises an alignment guide.

69. The tactile sensing system of any one of paragraphs 61 to 68, further comprising a needle guide configured to reversibly attach to the carriage.

70. The tactile sensing system of paragraph 69, wherein the needle guide further comprises a removal tab.

71. The tactile sensing system of any one of paragraphs 61 to 70, further comprising a needle release gate configured to reversibly attach to the carriage.

72. The tactile sensing system of paragraph 71, wherein the needle release gate is configured to reversibly secure a needle to the carriage in a position concentric with the needle guide.

73. The tactile sensing system of any one of paragraphs 61 to 72, wherein the scanhead further comprises a scanning knob on its proximal side.

74. The tactile sensing system of paragraph 73, wherein the scanning knob comprises at least one restrictor guide configured to restrict an insertion depth of a needle.

75. The tactile sensing system of any one of paragraphs 73 to 74, wherein the scanning knob comprises two or more restrictor guides configured to restrict the insertion depth of a needle, and wherein the scanning knob rotates to align one of said two or more restrictor guides with the alignment guide.

76. The tactile sensing system of any one of paragraphs 61 to 75, further comprising a bottom pad forming a distal surface of the tactile sensing system.

77. The tactile sensing system of paragraphs 76, wherein the bottom pad is configured to rest on a skin surface of a patient.

78. The tactile sensing system of any one of paragraphs 76 to 77, wherein the bottom pad is provided with a concave curvature having radius of approximately 1 meter.

79. The tactile sensing system of any one of paragraphs 76 to 78, wherein the bottom pad comprises a hardness of approximately 20 Shore A to 30 Shore A.

80. The tactile sensing system any one of paragraphs 61 to 79, wherein the scanhead is moveable relative to the carriage.

81. The tactile sensing system any one of paragraphs 61 to 80, wherein the scanhead is biased toward a proximal side of the system.

82. The tactile sensing system of paragraph 81, wherein the scanhead is biased by a spring.

83. The tactile sensing system of paragraph 82, wherein the scanhead comprises a spring protrusion, and wherein the spring guide and the spring protrusion are configured to center the spring relative to the scanhead and the carriage.

84. The tactile sensing system of any one of paragraphs 61 to 83, wherein the sensor array is a matrix array.

85. The tactile sensing system of any one of paragraphs 61 to 84, wherein the sensor array is a flexible sensor array.

86. The tactile sensing system of any one of paragraphs 61 to 85, wherein the sensor array is attached to a sensor array attachment area.

87. The tactile sensing system of any one of paragraphs 61 to 86, wherein the sensor array is adhered to a distal surface of the scanhead.

88. The tactile sensing system of any one of paragraphs 61 to 87, wherein the base further comprises a handle.

89. The tactile sensing system of paragraph 88, wherein the handle comprises a grip feature.

90. The tactile sensing device of any one of paragraphs 61 to 89, wherein the base further comprises a midline indicator.

91. The tactile sensing system of any one of paragraphs 61 to 90, wherein a distance between a distal surface of the base and a distal surface of the scanhead is approximately 0.1 cm to 5 cm.

92. The tactile sensing system of any one of paragraphs 61 to 91, wherein a distance between a distal surface of the base and a distal surface of the scanhead is approximately 1.8 cm.

93. The tactile sensing device of any one of paragraphs 61 to 92, wherein an active area of the sensor array is approximately 350 $mm^2$.

94. The tactile sensing system of any one of paragraphs 61 to 93, further comprising a locking mechanism which prevents the carriage from sliding along the scanning track when the scanhead is depressed.

95. The tactile sensing system of paragraph 94, wherein locking mechanism comprises one or more locking tabs having a pointed protrusion which engage with an elastomeric strip when the scanhead is depressed.

96. The tactile sensing system of any one of paragraphs 61 to 95, wherein the monitor device is coupled to the sensor array via a flexible printed circuit board.

97. The tactile sensing system of any one of paragraphs 61 to 96, wherein the monitor device comprises a printed circuit board.

98. The tactile sensing system of any one of paragraphs 61 to 97, further comprising a sleeve configured for receiving the monitor device.

99. The tactile sensing system of any one of paragraphs 61 to 98, comprising a power source.

100. The tactile sensing system of paragraph 99, wherein the power source is a battery located within the monitor device.

101. The tactile sensing system of any one of paragraphs 61 to 100, wherein the sensor array and the monitor device are reversibly connected.

102. The tactile sensing system of any one of paragraphs 61 to 101, comprising a wireless transmitter, the wireless transmitter operatively connected to the sensor array, for remotely transmitting the voltage signals output by the plurality of sensors.

103. The tactile sensing system of any one of paragraphs 61 to 102, wherein the processor is configured with instructions to display the target tissue location and the alignment guide location on the display screen in real time.

104. The tactile sensing system of any one of paragraphs 61 to 103, wherein the processor is configured with instructions to display a force being applied to the target tissue location in real time.

105. In one currently preferred embodiment, the invention provides a method of locating an insertion site using the system of any one of paragraphs 61 to 104, comprising: (a) sliding the carriage over a target tissue location; (b) depressing the scanhead into the target tissue location to capture a pressure map image on the display screen; (c) releasing the scanhead; (d) sliding the carriage toward an unmapped area of the target tissue location; and (e) repeating steps (b) to (d) until a pressure map is displayed across the target tissue location.

106. The method of paragraph 105, further comprising reading an applied force measurement from a force indicator.

107. In one currently preferred embodiment, the invention provides a method of marking an insertion site using the system of any one of paragraphs 68 to 104, comprising:

(a) sliding the carriage over a target tissue location;

(b) depressing the scanhead into the target tissue location to capture a pressure map image on the display screen; (c) releasing the scanhead; (d) sliding the carriage toward an unmapped area of the target tissue location; (e) repeating steps (b) to (d) until a pressure map is displayed across the target tissue location; (f) identifying an insertion site on the pressure map; (g) placing the alignment guide location at the insertion site on the pressure map; (h) placing a marking utensil through the alignment guide; and (g) marking the insertion site on a skin surface of a patient.

108. In one currently preferred embodiment, the invention provides method of guiding a needle into an insertion site using the system of any one of paragraphs 69 to 104, comprising:

(a) sliding the carriage over a target tissue location;

(b) depressing the scanhead into the target tissue location to capture a pressure map image on the display screen; (c) releasing the scanhead; (d) sliding the carriage toward an unmapped area of the target tissue location; (e) repeating steps (b) to (d) until a pressure map is displayed across the target tissue location; (f) identifying an insertion site on the pressure map; (g) placing the alignment guide location at the insertion site on the pressure map; (h) placing a needle through the needle guide; and (i) inserting the needle into the insertion site.

109. The method of paragraph 108, wherein further comprising a step of removing the system while retaining the needle in the insertion site.

110. The method of paragraph 108, further comprising reading an applied force measurement from a force indicator.

111. The method of paragraph 109, further comprising a step of unlocking a release gate prior to the step of removing the system.

112. The method of paragraph 108, wherein the needle is a local anesthetic needle and the method further comprises a step of injecting a local anesthesia into the insertion site.

113. The method of paragraph 112, further comprising a step of removing the local anesthetic needle; placing a spinal anesthesia needle through the needle guide; and inserting the spinal anesthesia needle into the insertion site.

114. The method of paragraph 112, further comprising a step of removing the local anesthetic needle; placing an introducer needle through the needle guide; and inserting the introducer needle into the insertion site.

115. The method of any one of paragraphs 112 to 114, further comprising a step of removing the system.

116. The method of paragraph 115, wherein the step of removing the system comprises opening the release gate.

117. The method of paragraph 115 or 116, further comprising a step of proceeding with a method of treatment after the step of removing the system.

118. The method of paragraph 108, wherein the needle is an introducer.

119. The method of paragraph 108, further comprising a step of configuring a depth restrictor prior to the step of placing the needle through the needle guide.

120. The method of paragraph 119, wherein the step of configured the depth restrictor comprises setting a height of the depth restrictor.

121. The method of paragraph 120, wherein setting the height of the depth restrictor comprises setting the depth restrictor to a lower position.

122. The method of paragraph 121, further comprising locking the depth restrictor in the lower position.

123. The method of paragraph 120, wherein setting the height of the depth restrictor comprises setting the depth restrictor to an upper position.

124. The method of paragraph 123, further comprising locking the depth restrictor in the upper position.

125. In one currently preferred embodiment, the invention provides a method of locating an insertion site using a tactile sensing device, the tactile sensing device comprising: a base comprising: a scanning track; a carriage configured to slide along the scanning track, the carriage comprising an alignment guide; a scanhead mounted to the carriage; a sensor array attached to the scanhead, the sensor array comprising one or more pressure sensors, each pressure sensor configured to output a voltage signal in response to a change in pressure; and a monitor device, comprising: a display screen operatively coupled to the sensor array, the display screen configured to display: a pressure map representing a target tissue location in an individual based upon the voltage signals output by the one or more pressure sensors; and a computing device comprising a processor operatively coupled to the sensor unit and the monitor device, and a non-transitory computer readable storage medium with a computer program including instructions executable by the processor causing the processor to: i) convert the voltage signals from the sensor array into the pressure map and display the pressure map on the display screen and ii) output an alignment guide location on the display screen; and the method comprising: (a) sliding the carriage over a target tissue location; (b) depressing the scanhead into the target tissue location to capture a pressure map image on the display screen; (c) releasing the scanhead; (d) sliding the carriage toward an unmapped area of the target tissue location; and (e) repeating steps (b) to (d) until a pressure map is displayed across the target tissue location.

126. The method of paragraph 125, further comprising identifying an insertion site; and placing the alignment guide at the location of the insertion site 127. The method of paragraph 126, further comprising placing a marking utensil through the alignment guide; and marking the insertion site on a skin surface of a patient.

128. The method of paragraph 126, further comprising placing a needle through a needle guide; and inserting the needle into the insertion site.

129. The method of paragraph 126, wherein further comprising a step of removing the system while retaining the needle in the insertion site.

130. The method of paragraph 129, further comprising a step of unlocking a release gate prior to the step of removing the system.

131. The method of paragraph 126, wherein the needle is a local anesthetic needle and the method further comprises a step of injecting a local anesthesia into the insertion site.

132. The method of paragraph 1321, further comprising a step of removing the local anesthetic needle; placing a spinal anesthesia needle through the needle guide; and inserting the spinal anesthesia needle into the insertion site.

133. The method of paragraph 132, further comprising a step of removing the local anesthetic needle; placing an introducer needle through the needle guide; and inserting the introducer needle into the insertion site.

134. The method of any one of paragraphs 131 to 133, further comprising a step of removing the system.

135. The method of paragraph 135, wherein the step of removing the system comprises opening the release gate.

136. The method of paragraph 1354 or 1365, further comprising a step of proceeding with a method of treatment after the step of removing the system.

137. The method of paragraph 126, wherein the needle is an introducer.

138. The method of paragraph 126, further comprising a step of configuring a depth restrictor prior to the step of placing the needle through the needle guide.

139. The method of paragraph 1398, wherein the step of configured the depth restrictor comprises setting a height of the depth restrictor.

140. The method of paragraph 139, wherein setting the height of the depth restrictor comprises setting the depth restrictor to a lower position.

141. The method of paragraph 1410, further comprising locking the depth restrictor in the lower position.

142. The method of paragraph 139, wherein setting the height of the depth restrictor comprises setting the depth restrictor to an upper position.

143. The method of paragraph 1434, further comprising locking the depth restrictor in the upper position.

144. A tactile sensing system comprising any feature described herein.

145. A method of using a tactile sensing system comprising using any of the methods disclosed herein.

IV. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. None of the terms require or are limited to situation characterized by the supervision (e.g. constant or intermittent) of a health care worker (e.g. a doctor, a registered nurse, a nurse practitioner, a physician's assistant, an orderly, or a hospice worker). A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "about" or "approximately" means within an acceptable error range for the particular value as determined by one of ordinary skill in the art, which will depend in part on how the value is measured or determined, e.g., the limitations of the measurement system. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees. 0.08 degrees, 0.07 degrees, 0.06 degrees, 0.05 degrees, 0.04 degrees, 0.03 degrees, 0.02 degrees or 0.01 degrees of a given value or range.

The term "proximal," as used herein, is defined as being closest or nearer to the user holding and/or operating the tactile sensing device, unless otherwise indicated. For example, a user pressing the tactile sensing device onto a patient.

The term "distal," as used herein, is defined as being farthest to the user holding and/or operating the tactile sensing device, unless otherwise indicated. For example, pressing the tactile sensing device onto a patient.

As used herein, the term "needle" may refer to an "injection needle," "introducer needle," "syringe," or "syringe and needle combination" and may be used interchangeably herein. Further, the terms are meant to encompass a syringe and needle combination and an introducer needle having a hub and/or handle including any additional components thereof known in the art.

Reference numerals used herein and in the corresponding drawings may refer to similar components or features using similar numerical reference. For example, a reference numeral #30 may be used to call out similar components in multiple figures, i.e. component #30 may be labeled as 130 in FIG. 1 and a similar component may be labeled 530 in FIG. 5. E.g. in the present application 130 refers to some embodiments of a carriage component depicted in FIGS. 1 and 330 refers to some embodiments if the carriage component in FIGS. 3A-3E.

The section headings used herein are for organizational purposes only and are not to be construed as limiting the subject matter described.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of locating an insertion site using a tactile sensing device, the tactile sensing device comprising:

a base comprising:

a scanning track;

a carriage configured to slide along the scanning track, the carriage comprising an alignment guide;

a scanhead mounted to the carriage;

a sensor array attached to the scanhead, the sensor array comprising one or more pressure sensors, each pressure sensor configured to output a voltage signal in response to a change in pressure; and a monitor device, comprising:

a display screen operatively coupled to the sensor array, the display screen configured to display: a pressure map representing a target tissue location in an individual based upon the voltage signals output by the one or more pressure sensors; and a computing device comprising a processor operatively coupled to the sensor array and the monitor device, and a non-transitory computer readable storage medium with a computer program including instructions executable by the processor causing the processor to: i) convert the voltage signals from the sensor array into the pressure map and display the pressure map on the display screen and ii) output an alignment guide location on the display screen; and the method comprising:

a. sliding the carriage over a target tissue location;

b. depressing the scanhead into the target tissue location to capture a pressure map image on the display screen;

c. releasing the scanhead;

d. sliding the carriage toward an unmapped area of the target tissue location; and e. repeating steps (b) to (d) until a pressure map is displayed across the target tissue location.

2. The method of claim 1, further comprising placing a marking utensil through the alignment guide; and marking the insertion site on a skin surface of a patient.

3. The method of claim 1, further comprising placing a needle through a needle guide; and inserting the needle into the insertion site.

4. The method of claim 3, further comprising removing the system while retaining the needle in the insertion site.

* * * * *